US008093021B2

(12) United States Patent
Hurtado et al.

(10) Patent No.: US 8,093,021 B2
(45) Date of Patent: Jan. 10, 2012

(54) DEFECTIVE SINDBIS VIRAL VECTORS

(75) Inventors: Alicia Hurtado, New York, NY (US); Daniel Meruelo, Scarborough, NY (US)

(73) Assignee: New York University, New York, NY (US)

( * ) Notice: Subject to any disclaimer, the term of this patent is extended or adjusted under 35 U.S.C. 154(b) by 32 days.

(21) Appl. No.: 12/484,818

(22) Filed: Jun. 15, 2009

(65) Prior Publication Data
US 2010/0120897 A1    May 13, 2010

Related U.S. Application Data

(60) Provisional application No. 61/061,493, filed on Jun. 13, 2008, provisional application No. 61/092,343, filed on Aug. 27, 2008.

(51) Int. Cl.
*C12N 15/64* (2006.01)
*C12N 15/00* (2006.01)
*C07H 21/02* (2006.01)
*C07H 21/04* (2006.01)

(52) U.S. Cl. .................. 435/91.4; 435/320.1; 536/23.1
(58) Field of Classification Search ................ 435/91.4, 435/320.1; 536/23.1
See application file for complete search history.

(56) References Cited

U.S. PATENT DOCUMENTS

| | | | |
|---|---|---|---|
| 7,303,898 B2 | 12/2007 | Hurtado et al. |
| 7,306,792 B2 | 12/2007 | Meruelo |
| 7,378,272 B2 | 5/2008 | Meruelo et al. |

FOREIGN PATENT DOCUMENTS

WO    02076468 A1    10/2002

OTHER PUBLICATIONS

Waehler et al Nature Genetics, 8: 573-587, 2007.*
Strauss et al., Complete nucleotide sequence of the genomic RNA of Sindbis virus, Virology 133(1) 92-110., (1984).
Theilmann et al., "Host-Dependent Evolution of the Sindbis Virus Promoter for Subgenomic mRNA Synthesis", J Virology, 1995, 69(12): 7775-7781.
Bhaumik S, Gambhir SS et al., "Optical imaging of Renilla luciferase reporter gene expression in living mice", PNAS USA 2002; 99: 377-382.
Burge BW et al., "Complementation between temperature-sensitive mutants of Sindbis virus", Virology 1966; 30 (2) :214-23.
Dubuisson J, Rice CM et al., "Sindbis virus attachment: isolation and characterization of mutants with impaired binding to vertebrate cells", J Virol. Jun. 1993; 67(6):3363-74.
Frolova E, Frolov I, Schlesinger S et al., "Packaging signals in alphaviruses", J. Virol. Jan. 1997 ; 71(1): 248-58.
Frothingham et al., (1955) "Tissue culture applied to the study of Sindbis virus", Am J Trop Med Hyg., 4: 863-871.
Geigenmuller-Gnirke U et al., "Deletion Analysis of the capsid protein of Sindbis virus: identification of the RNA binding region", J Virol., 1993; 67(3): 1620-6.

Lee H, Brown DT et al., "Mutations in an exposed domain of Sindbis virus capsid protein result in the production of noninfectious virions and morphological variants", Virology (1994) 202(1): 390-400.
Levy-Mintz P, Kielian M et al., "Mutagenesis of the putative fusion domain of the Semliki Forest virus spike protein", J Virol 1991; 65(8): 4292-300.
Li ML, Liao HJ, Simon LD, Stollar V et al., "An amino acid change in the exodomain of the E2 protein of Sindbis virus, which impairs the release of virus from chicken cells but not from mosquito cells", Virology 1999; 264(1):187-94.
McKnight KL, Simpson DA, Lin SC, Knott TA, Polo JM, Pence DF, Johannsen DB, Heidner HW, Davis NL, Johnston RE et al., "Deduced consensus sequence of Sindbis virus strain AR339: mutations contained in laboratory strains which affect cell culture and in vivo phenotypes", J. Virol. 1996; 70(3): 1981-9.
Myles KM et al., "Deletions in the putative cell receptor-binding domain of Sindbis virus strain MRE16 E2 glycoprotein reduce midgut infectivity in Aedes aegypto", J Virol 2003; 77(16):8872-81.
Ohno K, et al., "C (Min:30, Max:1000)

Vector A #13,15,16,17

Vector B #18,20,22

Vector C #24,26,27

15

22

27

Open

Organ array

Organ photo

P value (two-tailed) P<0.0001

DEFECTIVE SINDBIS VIRAL VECTORS

CROSS REFERENCE TO RELATED APPLICATIONS

The present application claims the benefit of U.S. Provisional Patent Application Ser. No. 61/061,493, filed on Jun. 13, 2008, and U.S. Provisional Patent Application Ser. No. 61/092,343, filed on Aug. 27, 2008, both of which are hereby incorporated by reference in their entireties.

STATEMENT REGARDING FEDERALLY SPONSORED RESEARCH OR DEVELOPMENT

The United States Government has certain rights to this invention by virtue of funding received from Group CA 100681 from the National Institutes of Health, Department of Health and Human Services.

FIELD OF THE INVENTION

The present invention is directed to defective Sindbis viral vectors, plasmids used to produce such vectors, pharmaceutical formulations containing the vectors, and methods for their production and use to treat mammals suffering from tumors.

BACKGROUND OF THE INVENTION

Sindbis virus, a member of the alphavirus genus in the Togaviridae family, is a single-stranded, enveloped, positive-sense RNA virus (Strauss & Strauss, 1994). In nature, it is transmitted via mosquito bites to mammals. Thus, as Sindbis virus has evolved as a blood-borne vector, this hematogenous delivery property enables Sindbis vectors to reach tumor cells throughout the circulation (Tseng et al 2004a,b).

U.S. Pat. No. 7,306,792, which is the National Stage of PCT/US02/09432 published as WO 02/076468 entitled TUMOR THERAPY WITH ALPHAVIRUS-BASED AND HIGH AFFINITY LAMININ RECEPTOR-TARGETED VECTORS discloses methods for treating solid tumors in mammals using Sindbis vectors. The method comprises systemically administering to a mammal harboring a tumor an amount of an Alphavirus vector effective to treat the tumor. The vector was said to have a preferential affinity for high affinity laminin receptors (HALR). Tumor cells which express greater levels of HALR compared to normal cells of the same lineage were preferentially killed by the vector. The anti-tumor effect was said to be due to the fact that Sindbis virus infection induced apoptosis in infected cells.

PCT/US 2004/026671 for A METHOD FOR DETECTING CANCER CELLS AND MONITORING CANCER THERAPY discloses the use of Sindbis viral vectors to identify cancer cells in the body of a mammal and monitor anti-cancer therapy.

U.S. Pat. No. 7,303,898 discloses defective Sindbis virus vectors, novel Helper and Replicon plasmids used to produce the vectors and methods for treating mammals harboring solid tumors which express higher levels of HALR than normal cells of the same lineage.

U.S. Pat. No. 7,378,272 discloses packaging cell lines for the continuous production of defective Sindbis virus vectors.

With the aim of broadening the knowledge of the way Sindbis vectors work for cancer gene therapy, two different kinds of Sindbis vectors, SP6-H/SP6-R, derived from wild type Ar-339, and JT-BB/JT-Rep derived from an Ar-339 laboratory adapted strain, Toto 1101 have been studied. Sindbis virus Ar-339 was first isolated in August 1952, from a pool of mosquitoes (*Culex pipiens* and *C. univittatus*) trapped in the Sindbis health district in Egypt (Hurlbut 1953; Taylor and Hurlbut 1953; Frothingham 1955; Taylor et al. 1955). Toto 1101 was made out of the heat resistant (HR) strain initially derived from AR-339 (Burge and Pfefferkorn, 1966). The first studies done with JT vectors in animal models showed good targeting of tumor cells and significant reduction of metastatic implant size (Tseng et al. 2002). Further studies of these vectors in tumor-induced SCID mice were done using the new imaging technique of IVIS®, that allows in vivo detection of viral vector and tumor cells in the same animal. In tumor-induced SCID mice there was a good correlation between vectors and tumor cells (Tseng et al. 2004b). Although these positive results in vector targeting and in vivo growth reduction of tumors and mouse survival, which are very promising for gene therapy, survival of all mice in these tumor models has not yet been achieved.

Therefore, what is need in the art are improved Sindbis viral vectors for use as anti-tumor agents.

BRIEF SUMMARY OF THE INVENTION

Disclosed herein are new vectors made from wild type Ar-339 Sindbis virus, with differences in replicase and envelope proteins between JT vectors and consensus Sindbis virus sequences, and also between JT and Ar-339 vectors. The chimeras combining both strains were produced and studied in tumor-induced SCID mice by the IVIS® imaging technique. Surprisingly JT envelope proteins targeted tumors more effectively than Ar-339 while Ar-339 replicase showed increased efficiency in tumor reduction. To analyze which residues would be responsible for tumor targeting, mutants of Ar-339 E2 envelope protein were made and tested by IVIS® imaging in ES-2 induced and tumor free mouse models. The change of only one amino acid from Glu to Lys at position 70 of Ar-339 E2, suppressed the ability to target metastatic tumor implants in mice. Double E2 mutant Mut-2, with K70 and V251 did not revert the targeting. Only when the whole sequence of JT E2 was substituted in the Ar-339 helper was the ability of targeting metastatic tumor implants recovered, though with less intensity. Thus, residue 70 in the outer leaf of the E2 protein is essential for tumor specific targeting of Sindbis vectors.

In one aspect, the present invention provides a purified, isolated nucleic acid sequence comprising the nucleotide sequence consisting of the sequence as set forth in SEQ ID NO:60, DM-H101.

In yet a further aspect the present invention provides a defective Sindbis virus vector produced by a method comprising the steps of (a) providing a linearized Replicon plasmid T7-StuI-RLacZ#202 comprising a nucleotide sequence consisting of the sequence as set forth in SEQ ID NO:65 and a linearized Helper plasmid DM-H101 comprising the nucleotide sequence consisting of the sequence as set forth in SEQ ID NO:60;

(b) transcribing said Replicon plasmid and said helper plasmid to produce RNA;

(c) collecting the RNA transcribed in step (b) and transfecting cells with said RNA;

(d) incubating said transfected cells for a time and at a temperature effective for producing defective Sindbis virus vectors; and (e) collecting said defective Sindbis virus vectors from the medium of said transfected cells.

In a still further aspect, the present invention provides an isolated nucleic acid comprising the nucleotide sequence encoding plasmid T7 DM-H101.

In a still further aspect the present invention provides an isolated nucleic acid comprising the nucleotide sequence consisting of the sequence set forth in SEQ ID NO:65 T7-StuI-RLacZ#202.

These and other aspects of the present invention will be apparent to those of ordinary skill in the art in light of the present specification, claims and figures.

Ar-339 11703 nt genomic RNA, is illustrated schematically in grey line, viral subgenomic promoter ($P_{SG}$) nt 7334 to 7646, is represented as grey solid box. The viral genome was cloned in 6 PCR overlapping fragments. The viral replicase (grey dotted line) and the subgenomic promoter were cloned in 4 PCR fragments: CDNA-1, CDNA-2, CDNA-3A and CDNA-3B. The Sindbis subgenomic promoter and structural proteins sequence (gray dashed line) were cloned in 2 PCR overlapping fragments CDNA-4 and CDNA-5. The position of restriction enzyme sites in the PCR fragments that were used for further cloning strategy are indicated.

Figure 2:
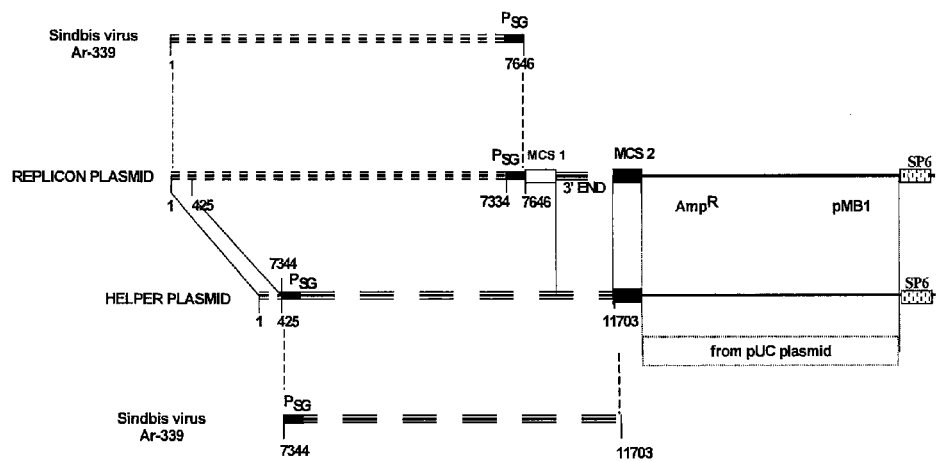

FIG. 2. Sindbis replicon and helper plasmids.

The Sindbis virus Ar-339 genome was split in two to generate both replicon and helper plasmids. Viral sequences are represented in grey. Virus nucleotide numbers are indicated and follow the Strauss et al. 1984 sequence.

Figure 3:
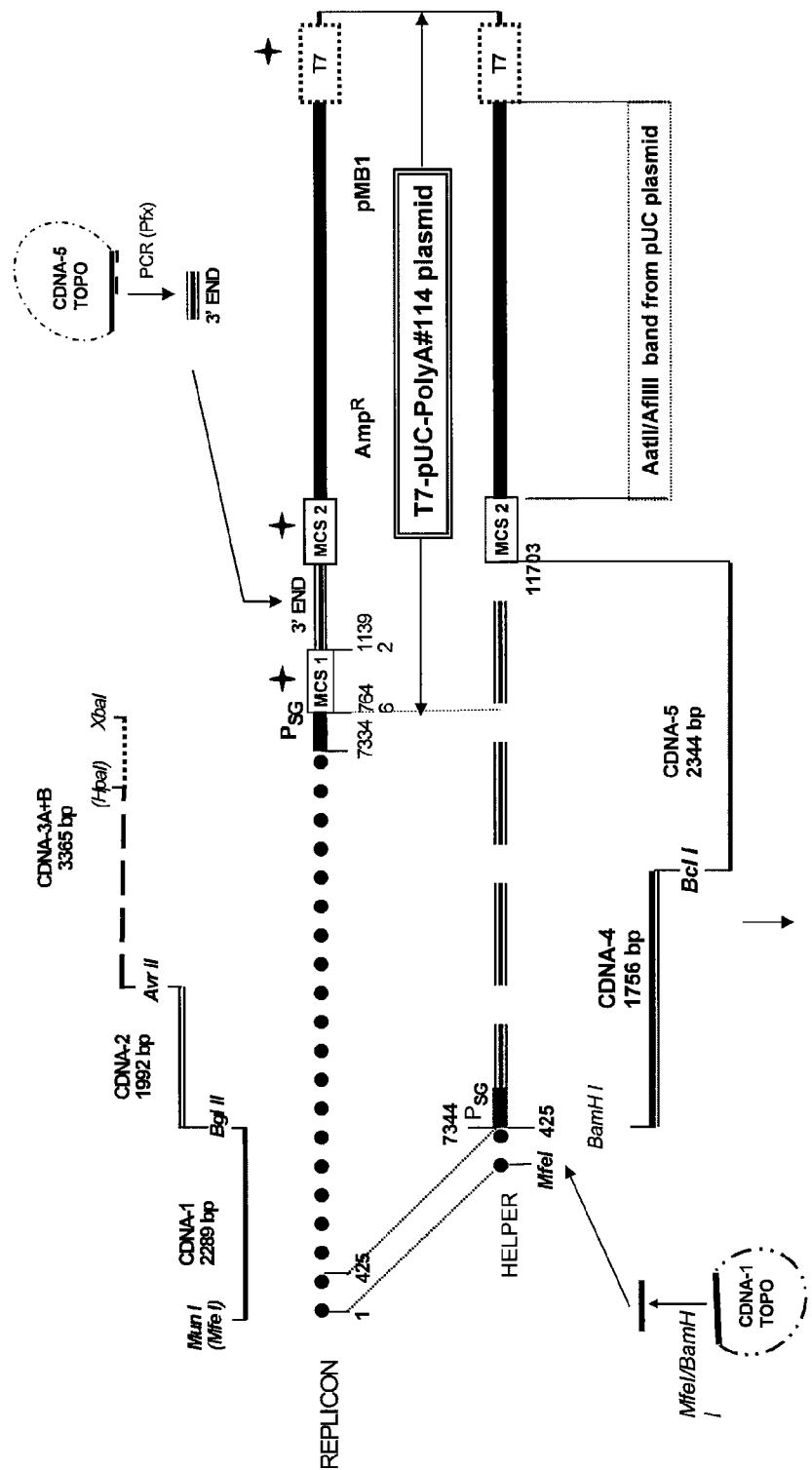

FIG. 3. Summary of vector constructions.

The first step generated the plasmid T7-pUC-PolyA#114 that contains the bacterial segment (ampicillin resistance, pMB1 replication origin), bacteriophage promoter T7, the two multicloning sites (MCS1 and MCS2) and the 3' end of the virus sequence (grey dashed line). To generate the replicon, restriction enzyme (RE) digested and gel purified DNA fragments from CDNA-1, CDNA-2 and CDNA-3 were cloned sequentially into T7-pUC-PolyA#114. To generate the helper, first the MfeI/BamHI fragment from the CDNA-1 plasmid was cloned into T7-pUC-PolyA#114, and bands from CDNA-4 and CDNA-5 were cloned into this plasmid. The sequences of the primers used to clone the Ar-339 cDNA fragments are shown in Table I (Appendix A).

Figure 4A:
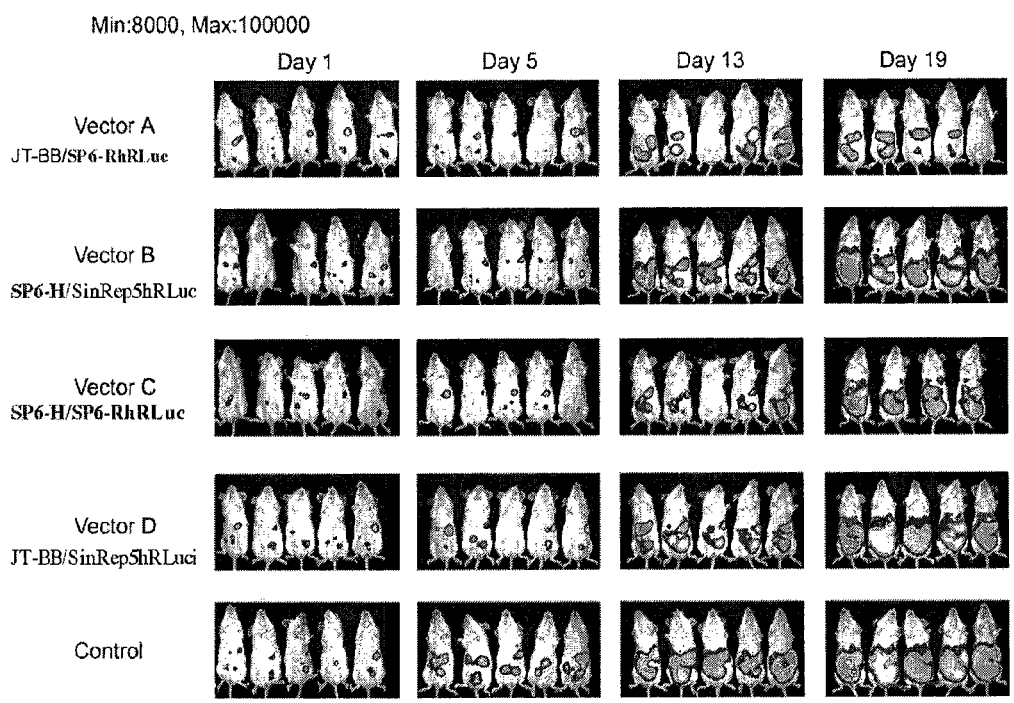
Figure 4B:
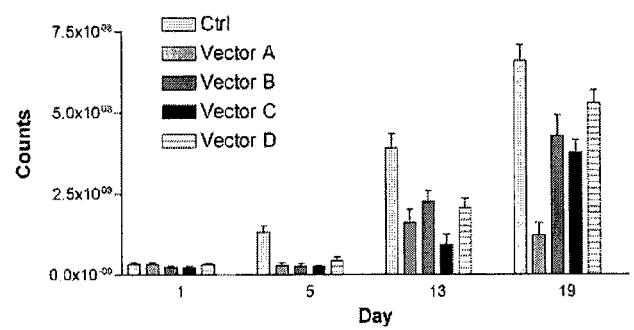

FIGS. 4(A and B). Suppression of disease progression by Ar-339 and JT chimeric vectors. A) ES-2/Fluc cells ($1.5 \times 10^6$) were i.p. inoculated into SCID mice on day 0. The next day (day 1), mice were imaged using the IVIS® Imaging System using D-luciferin as the substrate and were split into five groups of five mice each: control, which received no vector treatment, vector A (JT-BB/SP6-RhRLuc), vector B (SP6-H/JT-RephRluc), vector C (SP6-H/SP6-RhRluc) and vector D (JT-BB/JT-RephRluc). On day 5 the groups received daily i.p. treatments of corresponding Sindbis vectors and were IVIS® imaged on days 1, 5, 13 and 19. All vector treatments suppressed the tumor growth on the mesentery and diaphragm and reduced the signals on the omentum compared with control mice. B) Quantitative analysis of the whole-body total photon counts of control and Sindbis-treated mice. Error bars represent the SEM.

Figure 5:
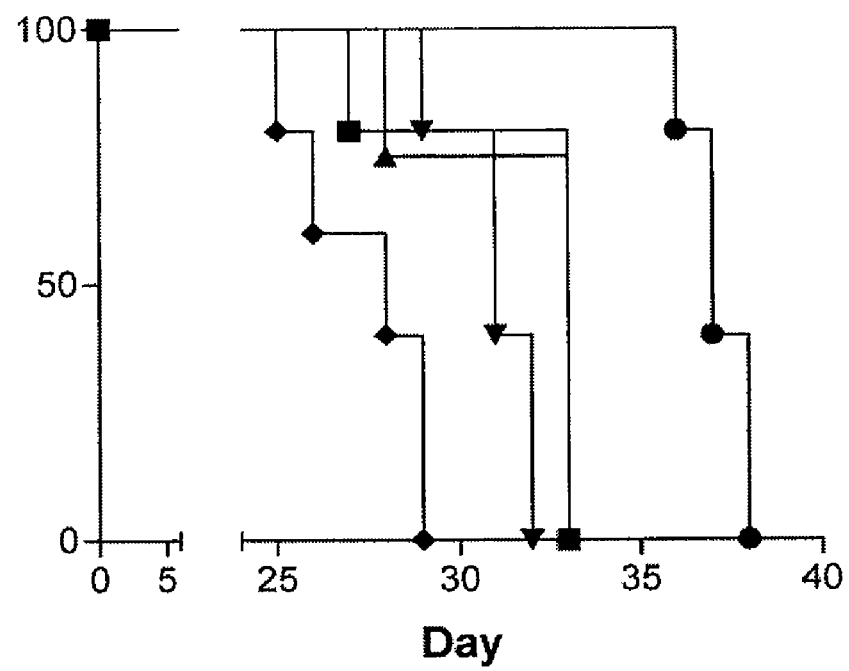

FIG. 5. Survival curves of mice treated with Ar-339 and JT vectors. Survival curve of mice described in FIG. 4. Vector A was the most efficient in prolonging the survival of mice bearing ES-2/Fluc tumors.

FIGS. 6 (A and B). Colocalization in peritoneal cavity of vector C. A) Vector C (SP6-H/SP6-RhRluc) infection colocalized with the metastasized ES-2/Fluc tumors in the peritoneal cavity as determined by the IVIS® system. SCID mice were i.p. inoculated with $1.5 \times 10^6$ ES-2/Fluc cells. Five days later, while the disease was still microscopic, inoculated mice received a single i.p. treatment of Vector C and were imaged the next day. The first IVIS® imaging was done by i.p. injection of Rluc substrate, coelenterazine, followed by a 5-minute acquiring interval (left panel). Thirty minutes after the coelenterazine injection, when the short-lived Rluc signals faded away, Fluc substrate, D-luciferin, was i.p. injected to determine the ES-2/Fluc tumor locations (right panel). B) Correlation analysis of vector C shows a high correspondence between tumor cells and vector infection in the peritoneal cavity.

FIGS. 7(A and B). Background infection of Ar-339 and JT chimeric vectors. A) Five tumor-free mice per group were i.p. injected on day 0 with one dose of vector A (JT-BB/SP6-RFluc), vector B (SP6-H/JT-RepFluc) or vector C (SP6-H/SP6-RFluc) and next day (day 1) IVIS® imaged for vector luciferase signal). The peritoneum was removed for imaging of the peritoneal cavity and the organs were harvested and imaged for the representative mice (rows 3 to 5). All vectors showed infection in fat tissue, and in vector B and C groups some mice showed a low background signal on ribs but not in organs B) Some mice per group received a second i.p. injection of the vectors of day 2, and were IVIS® imaged in: the peritoneal cavities (second row) and organs (bottom rows) on day 3. Very low signals were observed in fat tissue for vectors B and C.

FIGS. (8A and B). Tumor targeting of Ar-339 and JT chimeric vectors. A) SCID female mice were injected i.p. on day 0 with $2 \times 10^6$ ES-2 cells/mouse. On day 4 five mice per group were i.p. injected with one doses of vector A (JT-BB/SP6-RFluc), vector B (SP6-H/JT-RepFluc) or vector C (SP6-H/SP6-RFluc) and next day (day 5) IVIS® imaged for vector luciferase signals. The peritoneum was removed for imaging of the peritoneal cavity and the organs were harvested and imaged. All vectors targeted tumor implants. Tumors on the peritoneum, pancreas-omentum and bowel are circled. B) Some mice per group received a second i.p. injection of the vectors of day 6, and the peritoneal cavities (second row) and organs (bottom rows) were IVIS® imaged on day 7. One mouse per group (#28, 33, 38) was not injected to serve as a luciferase background control. Vectors B and C showed decreased bioluminescence signals in tumors compared with the first injection (A).

FIG. 9A-9E. SP6-H Ar-339 E2 mutants. Amino acids changed in Ar-339 E2 mutants Mut-1 (9C), Mut-2 (9D) and Mut-4 (9E). Sequences and residues from the JT-BB plasmid are shown in 9A, those corresponding to Ar-339 are represented in 9B.

Figure 10A:
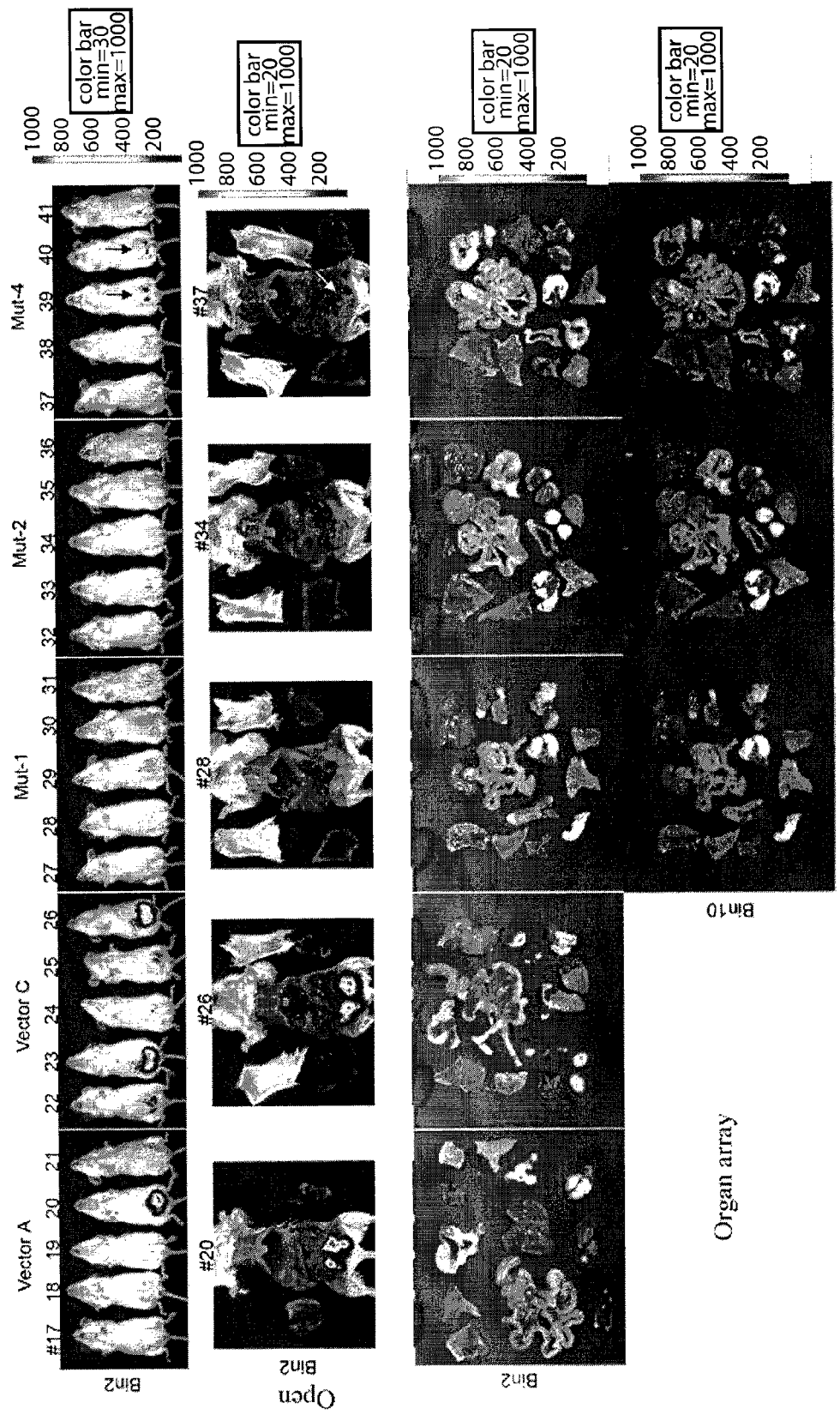
Figure 10B:
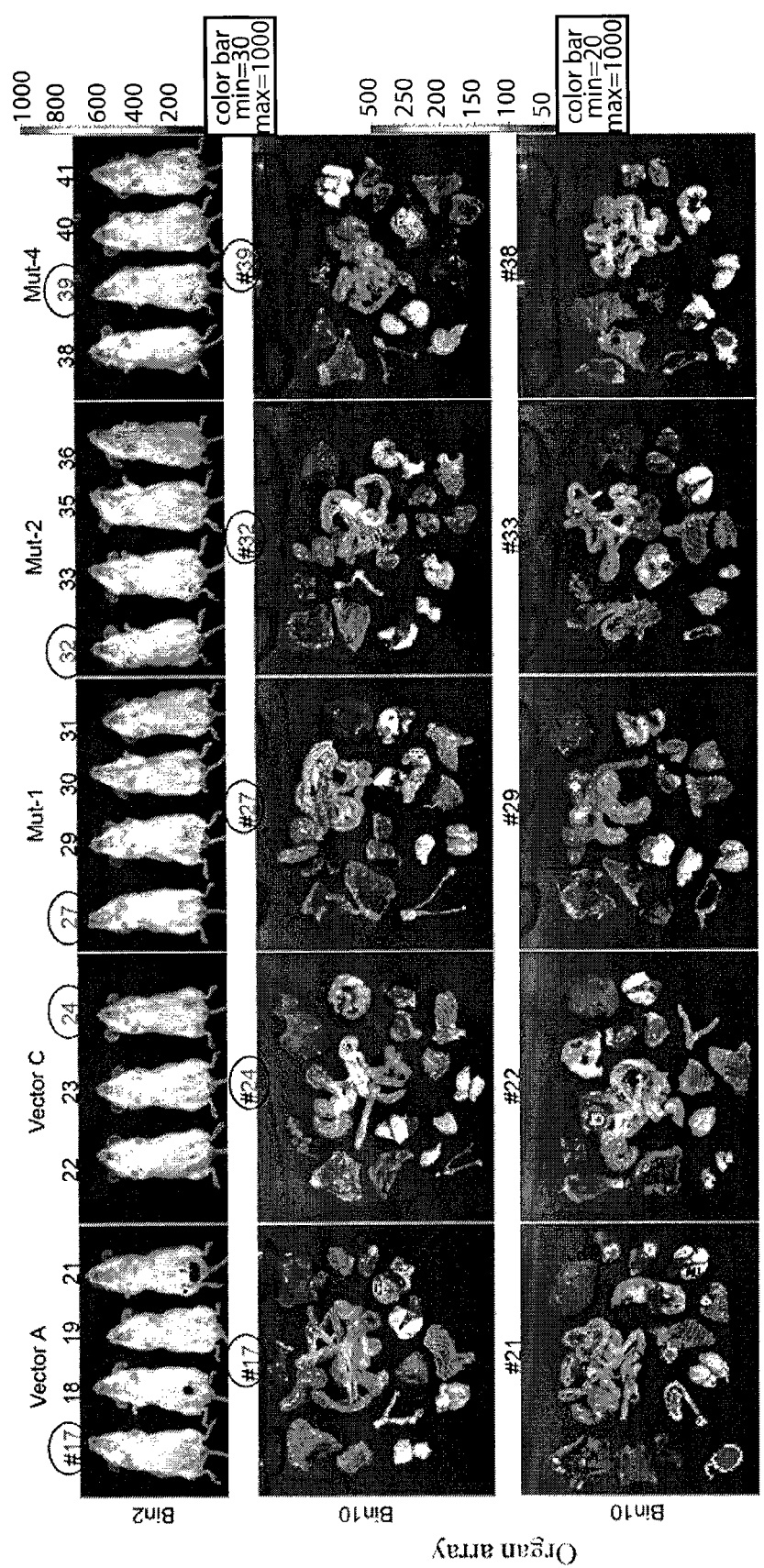

FIGS. 10(A and B). Background infection of Ar-339 E2 mutants. A) Five tumor-free mice per group were i.p. injected on day 0 with one dose of vector A (JT-BB/SP6-RFluc), vector C (SP6-H/SP6-RFluc), Mut-1 (SP6-H-K70/SP6-RFluc), Mut-2 (SP6-H-K70-V251/SP6-RFluc) and Mut-4 (SP6-H-I3-K70-E181-V251/SP6-RFluc). The next day, mice were IVIS® imaged for vector luciferase signals. The peritoneum was removed for imaging of the peritoneal cavity of representative mice and the organs were harvested and also imaged. The E2 mutant vectors did not show background infection of fat tissue as observed with vectors A and C. E2 mutant organ arrays were also IVIS® imaged at Bin 10 resolution to increase the detection limit (bottom row), arrows point to regions with signals. B) Some mice per group received a second i.p. injection of the vectors of day 2, organs were harvested and IVIS® imaged. Mice circled (#17, 24, 27, 32, and 39) were not injected to serve as luciferase background controls. Only using high sensitivity Bin 10 resolution, low bioluminescence signals (indicated with arrows) were detected in mice 21, 22 and 38 of vector groups A, C and Mut-4 respectively.

Figure 11A:
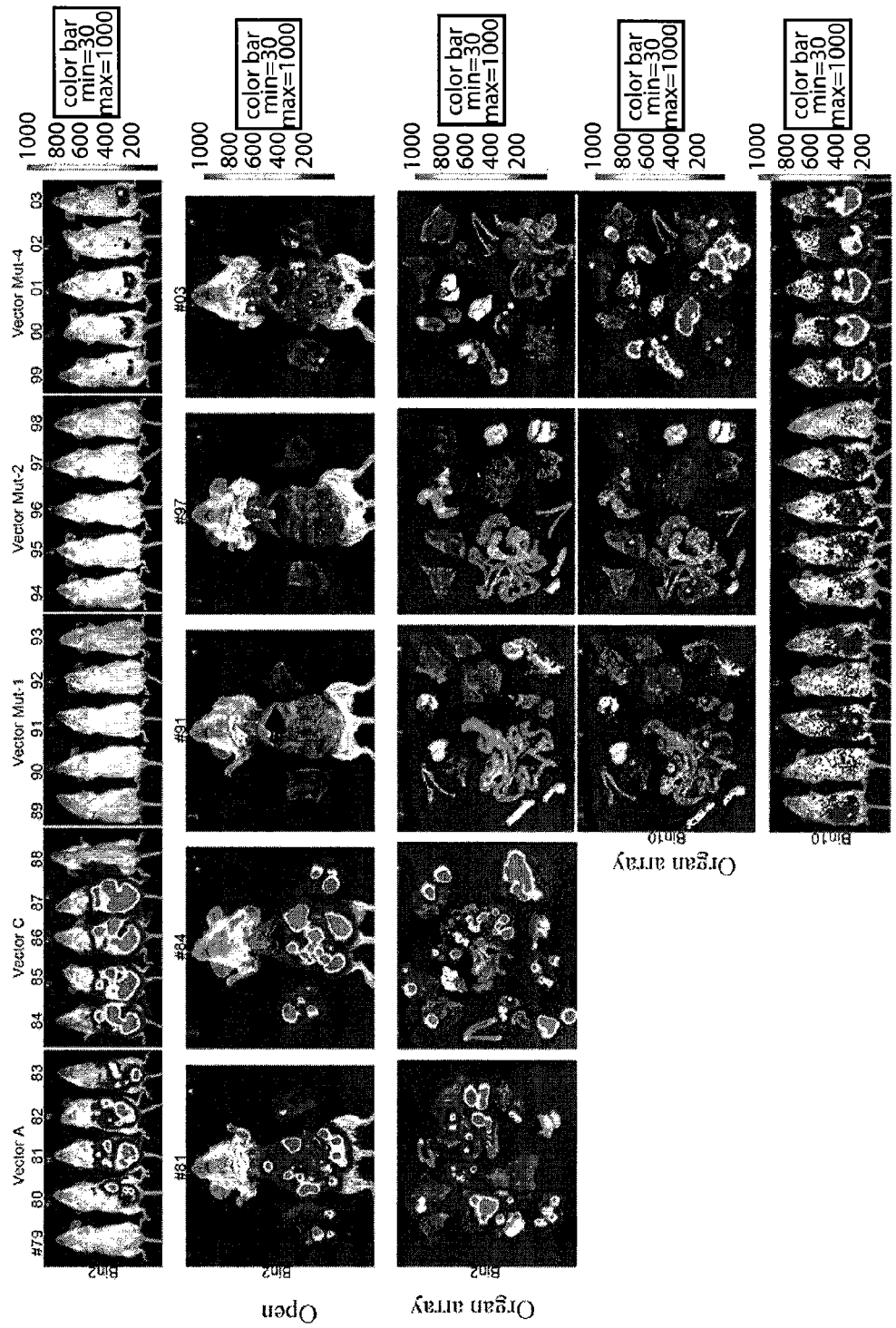
Figure 11B:
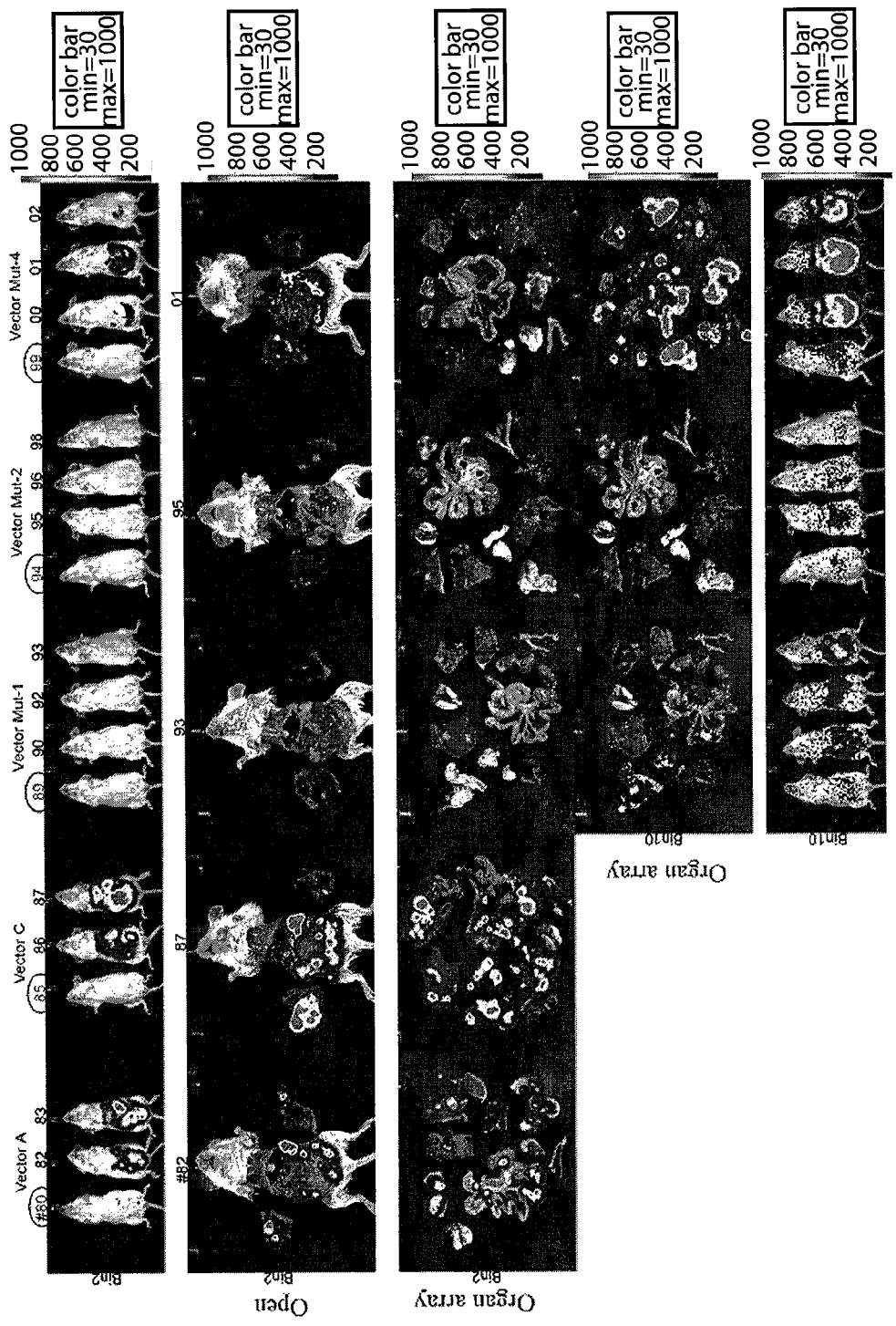

FIGS. 11(A and B). Tumor targeting of Ar-339 E2 mutants. A) SCID female mice were i.p. injected on day 0 with 2×10$^6$ ES-2 cells/mouse. On day 4, five mice per group were i.p. injected with one dose of vector A (JT-BB/SP6-RFluc), vector C (SP6-H/SP6-RFluc), Mut-1 (SP6-H-K70/SP6-RFluc), Mut-2 (SP6-H-K70-V251/SP6-RFluc) or Mut-4 (SP6-H-I3-K70-E181-V251/SP6-RFluc), and the next day (day 5) IVIS® imaged for vector luciferase signals. The peritoneum was removed for imaging of the peritoneal cavity and the organs were harvested and imaged. Vectors A and C efficiently targeted tumors, Mut-4 showed low bioluminescence signals, Mut-1 and Mut-2 did not show luminescence. For the three mutants, IVIS® images at Bin 10 resolution were taken of full mice and organ arrays. Only at this high sensitivity did some mice of Mut-1 and Mut-2 groups show very low residual signals in metastatic implants (lower panels), arrows point to regions with signals. B) Some mice per group received a second i.p. injection of the vectors on day 6, and peritoneal cavities and organs were IVIS® imaged on day 7. One mouse per group (#80, 85, 89, 94 and 99) was not injected to serve as luciferase background controls. For the three E2 mutants, high sensitivity Bin 10 images were also taken. Vectors showed equivalent infection pattern as for first injection.

Figure 12A:
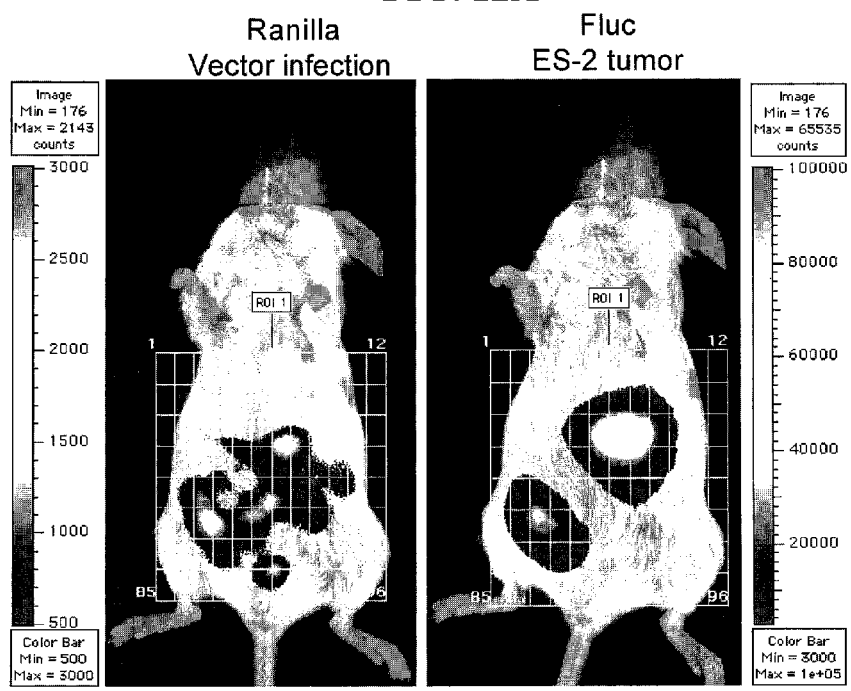
Figure 12B:
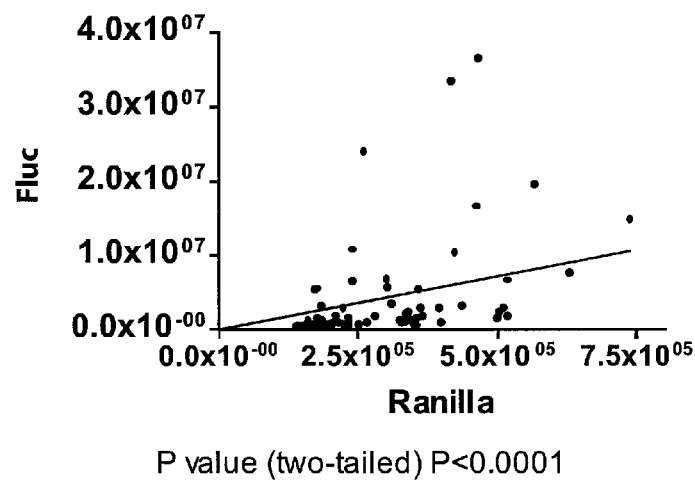

FIGS. 12 (A and B) Colocalization in peritoneal cavity of vector Mut-4. A) Vector Mut-4 infection colocalized with the metastasized ES-2/Fluc tumors in the peritoneal cavity as determined by the IVIS® Imaging System. SCID mice were i.p. inoculated with 1.5×10$^6$ ES-2/Fluc cells. Five days later, while the disease was still microscopic, inoculated mice received a single i.p. treatment of vector Mut-4 and were imaged the next day. The first IVIS® imaging was done by i.p. injection of Rluc substrate, coelenterazine, followed by a 5-minute acquiring interval (left panel). Thirty minutes after the coelenterazine injection, when the short-lived Rluc signals faded away, Fluc substrate, D-luciferin, was i.p. injected to determine the ES-2/Fluc tumor locations (right panel). B) Correlation analysis of vector Mut-4 shows a high correspondence between tumor cells and vector infection in the peritoneal cavity.

Figure 13A:
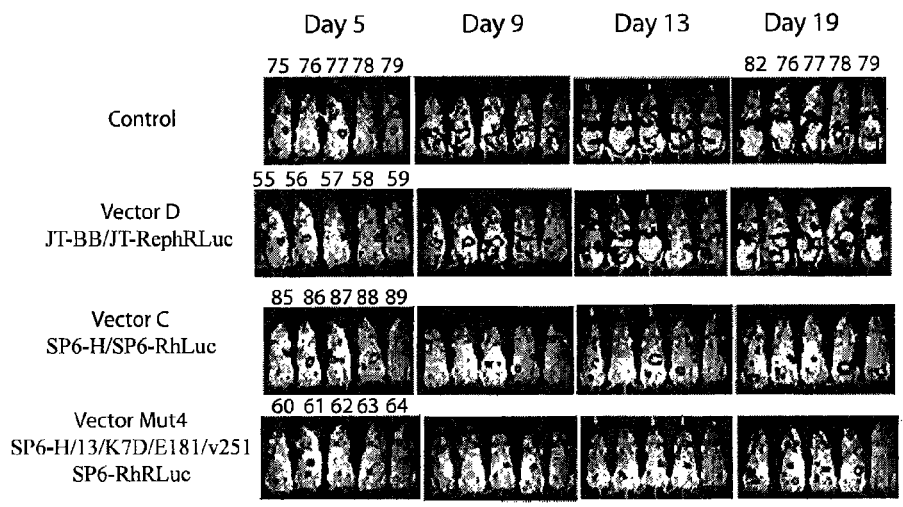
Figure 13B:
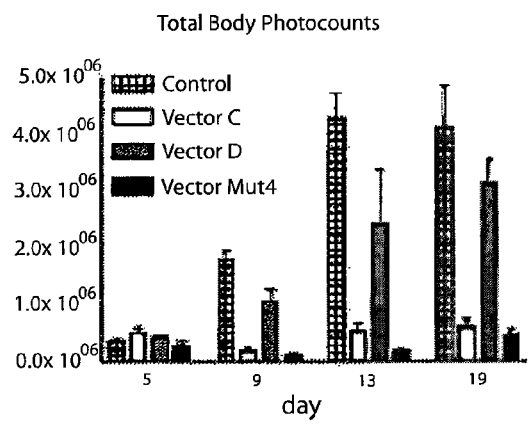
Figure 13C:
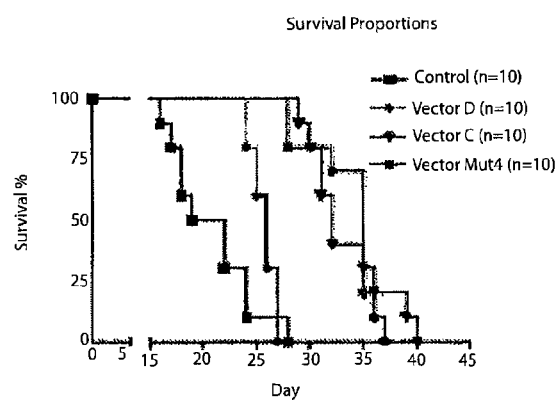

FIG. 13. (A-C) Suppression of disease progression by Ar-339 and Mut-4 chimeric vectors. A) ES-2/Fluc cells (1.5×10$^6$) were i.p. inoculated into SCID mice on day 0. The next day (day 1), mice were imaged using the IVIS® Imaging System with D-luciferin as substrate and were split into four groups of five mice each: control which received no vector treatment, vector D, vector C and vector Mut-4. The groups received daily i.p. treatments of corresponding Sindbis vectors (10$^6$ TU) and were IVIS® imaged on days 1, 5, 13 and 19 after the start of treatment. All vector treatments suppressed the tumor growth on the mesentery and diaphragm and reduced the signals on the omentum compared with control mice. Image scale Min 8×10$^3$ Max 10$^5$ counts/pixel. B) Quantitative analysis of the whole-body total photon counts of control and Sindbis-treated mice. Error bars represent the SEM. C) Survival curve of mice.

Figure 14:
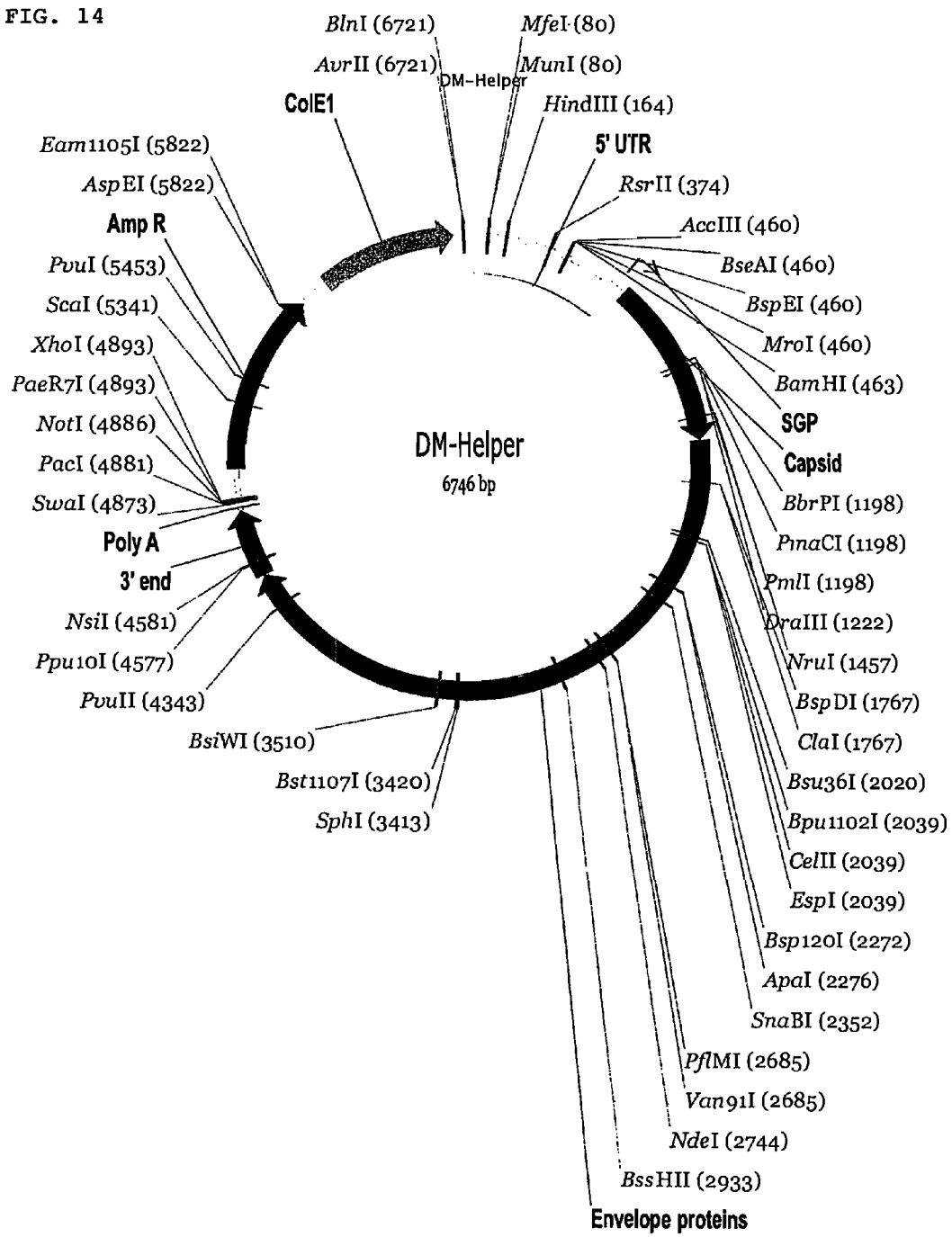

FIG. 14 is a Restriction endonuclease map of the DM-Helper plasmid.

DETAILED DESCRIPTION OF THE INVENTION

The term Aabout@ or Aapproximately@ means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, Aabout@ can mean within 1 or more than 1 standard deviations, per the practice in the art. Alternatively, Aabout@ can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition. Cold Spring Harbor, N.Y.: Cold Spring Harbor Laboratory Press, 1989 (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); Ausubel, F. M. et al. (eds.). *Current Protocols in Molecular Biology*. John Wiley & Sons, Inc., 1994.

Amino acid residues in proteins are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Trytophan is Trp or W; Arginine is Arg or R; and Glycine is Gly or G.

As used herein, the term Atumor@ refers to a malignant tissue comprising transformed cells that grow uncontrollably. Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, neuroglioma, and retinoblastoma.

The phrase Apharmaceutically acceptable@, as used in connection with compositions of the invention, refers to molecular entities and other ingredients of such compositions that are physiologically tolerable and do not typically produce untoward reactions when administered to a human. Preferably, as used herein, the term Apharmaceutically acceptable@ means approved by a regulatory agency of the Federal or a state government or listed in the U.S. Pharmacopeia or other generally recognized pharmacopeia for use in mammals, and more particularly in humans.

The term Atherapeutically effective@ applied to dose or amount refers to that quantity of a compound or pharmaceutical composition that is sufficient to result in a desired activity upon administration to a mammal in need thereof. As used herein with respect to viral vectors of the invention, the term Atherapeutically effective amount/dose@ refers to the amount/dose of a vector or pharmaceutical composition containing the vector that is sufficient to produce an effective anti-tumor response upon administration to a mammal.

Described below are preferred replication defective Sindbis viral vectors for use in the present invention termed vector C, Mut-1, Mut-2 and Mut-4 and the plasmids used to produce them. Mut-1, Mut-2 and Mut-4 contain mutations in the E2 envelope protein and are alternatively referred to herein as "E2 Mutants".

The E2 mutants of the present invention were produced using unique helper and replicase plasmids. The present invention provides four novel helper plasmids (SP6-H (SEQ ID NO:37) SP6-H-K70 (SEQ ID NO:38), SP6-H-K70-V251 (SEQ ID NO:40) and SP6-H-I3-K70-E181-V251 (SEQ ID NO:39)) and one replicon plasmid (SP6-R (SEQ ID NO:36)). Helper plasmid SP6-H, which does not contain any amino acid changes but has a different nucleotide sequence, is set forth in SEQ ID NO:37. The 4 helper plasmids are used to produce Vector C, Mut-1, -2 and -4 vectors, respectively, when produced using the novel replicon plasmid.

In order to produce viral vectors in this system, two plasmids are used, the replicon and the helper. The replicon contains the viral replicase, the viral packaging signal, nt 945 to nt 1075, (Weiss B et al. 1994; Frolova et al 1997); the viral subgenomic promoter, multicloning site I (MCS1) to allow for the insertion and expression of the gene of interest, and the 3' end of the virus (nt 11394 to 11703) to allow viral (−) strand RNA synthesis. A second multicloning site (MCS2) allows for the linearization of the plasmid for in vitro transcription.

The helper plasmid contains the first 425 nt of the virus, followed by the 3' end of the virus from nt 7334 to nt 11703 which includes the subgenomic promoter, the capsid and the viral envelope proteins (E3, E2, 6K and E1) and the 3' end (nt 11394 to 11703).

Both plasmids share the following viral sequences: the first 425 nt and the 309 nt of the 3' end and the sub genomic promoter.

Both plasmids have several non-viral elements in common, the replication origin (rep pMB1) and the Ampicillin resistance gene from the pUC cloning plasmid; the promoter for in vitro transcription (T7 or SP6) and the MCS2. In the construction process a plasmid containing the pUC sequences, SP6 or T7 promoter, the multicloning sites, and the 3' viral end, which are common to both vectors, was first generated. The specific viral sequences were then cloned into this plasmid (FIG. 3).

In order to produce the viral vectors of the present invention, one pair of plasmids are linearized using restriction enzymes such as PacI, NotI, or XhoI, transcribed in vitro, the RNAs collected and electroporated into cells. For in vitro transcription, a promoter is inserted before the Sindbis viral sequences. Preferably, the promoter is a bacteriophage promoter, for us with its respective RNA polymerase such as SP6 or T7 (Ambion Austin, Tex.).

Cells for use in the present invention include BHK-21 cells (available from the American Type Culture Collection, ATCC, Manassas, Va. as CRL 6281), ES-2 cells, (ATTC, CRL 1978), ES-2/Fluc cells that were derived from the ES-2 line by transfection of a plasmid, pIRES2-Luc/EGFP and the MOSEC cell line (clone ID8). The transcribed RNAs (i.e., one helper and one replicon plasmid) are electroporated into the cells at a concentration ranging between about 0.75 mg/mL and about 1.25 mg/mL. The ratio of viral RNA to cell concentration ranges between about 30-50 μg RNA per $6 \times 10^6$ cells. Electroporation is performed using equipment commercially available from e.g., Bio Rad (Hercules, Calif.)

The transfected cells are fed medium containing 5% fetal bovine serum (FBS) and incubated at 37° C. for about 12 hours. The medium is then discarded, replaced with 9 ml of Opti-MEM I medium (GIBCO-BRL Invitrogen, San Diego Calif.) and incubated at about 37° C. for about 24 hours. Then, supernatants are collected and centrifugated at 2,400 rpm (≈1,500 g) for 15 min to eliminate cell debris. Clear supernatants, containing the viral vector, were collected, aliquoted and stored at −80° C.

The viral vectors can be used as anti-tumor agents as described in International Application No. PCT/US02/09432 published as WO 02/076468. Although the Mut-1 vectors do not bind to the high affinity laminin receptors (HALR), they are useful as controls and to monitor non-viral effects of the vectors. Since Mut-1 vectors do not enter cells, the contribution of host factors in the anti-cancer response can be studied.

The plasmids of the present invention can be used to transfer of cells and create packaging cell lines for the continuous production of defective Sindbis viral vectors as described in copending Ser. No. 10/983,432 and in Paper Example 1 below.

The amount of viral vectors produced may be determined as described below in the Examples. Briefly, clear supernatants are serial diluted in Opti-MEM I medium and 300 μL of each vector dilution are added to a 35 mm well in 12-well plates, containing $2 \times 10^5$ cells. After incubation for 1 hour at room temperature, the cells are washed with PBS (Phosphate buffered saline) and incubated with 2 mL of αMEM at 37° C. for about 24 hours. Media is removed, cells are washed with PBS and cell lysates are prepared and assayed for the different reporter activity: β-galactosidase, firefly luciferase or *Renilla luciferase*. Vector titers were estimated as the highest dilution having detectable reporter activity. Detection of reporter activities is described in Example 2.

Viral vectors can be produced by linearizing helper and replicon plasmids after the polyA sequence, followed by separately performed in vitro transcription reactions. Usually, 1.6 μg of plasmid yields 15-25 μg of mRNA/reaction. Then 30-50 μg of both RNAs are co-electroporated into $6 \times 10^6$ BHK-21 cells, which are then incubated in 10 ml of αMEM containing 5% FBS at 37° C. for about 12 h. Then, the medium is replaced with 9 ml of Opti-MEM I medium (GIBCO-BRL Invitrogen, San Diego Calif.) supplemented with 0.7 μM $CaCl_2$, cells are incubated at 37° C. for about 24 h, supernatants collected and centrifuged at ≈1,500 g for 15 min to eliminate cell debris. The procedure can be scaled up using the following electroporation ratios: 5-8 μg helper and replicon mRNA's per $10^6$ BHK-21 and 9 mL Ca-Opti-MEM media per reaction.

The viral vectors of the present inventions have the following properties which are summarized in Strauss and Strauss 1994. Briefly, as Alphaviruses replicate exclusively in the cytoplasm, there is no possibility of adventitious splicing. Because they are replication incompetent and packaging defective, the vectors are incapable of spread by reinfection. The vector replicates to high copy number inside the cell, and large quantities of mRNA are produced, leading to production of large amounts of the protein of interest Viral vectors obtained as described herein can be formulated in a pharmaceutical composition for administration to a patient. As used herein, a Apharmaceutical composition@ includes the active agent, i.e., the viral vector, and a pharmaceutically acceptable carrier, excipient, or diluent. The phrase Apharmaceutically acceptable@ refers to molecular entities and compositions that are physiologically tolerable and do not typically produce an allergic or similar untoward reaction, such as gastric upset, dizziness and the like, when administered to a human. Preferably, as used herein, the term Apharmaceutically acceptable@ means approved by a regulatory agency of the Federal or a state government or listed in the U.S. Pharmacopeia or other generally recognized pharmacopeia for use in animals, and more particularly in humans. The term Acarrier@ refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

For human therapy, the viral vectors of the present invention may be prepared in accordance with good manufacturing process (GMP) standards, as set by the Food & Drug Administration (FDA). Quality assurance (QA) and quality control (QC) standards will include testing for replication competent virus (if the virus vector is replication defective), activity (colony forming units [CFU] per number of viral particles, tested by induction of apoptosis or cytopathic effect (CPE), or by expression of a marker gene such as β-galactosidase), toxicity, and other standard measures.

In order to treat the tumors, the pharmaceutical composition is administered by any route that will permit homing of the vector to the tumor cells. Preferably, administration is parenteral, including, but not limited to, intravenous, intraarteriole, intramuscular, intradermal, subcutaneous, intraperitoneal, intraventricular, and intracranial administration. As disclosed herein, viral vectors can be also administered to the tumor-bearing animal via intranasal or oral route (see Hardy, In: *The Arbiviruses: Epidemiology and Ecology*, Ch. 4, pp. 87-126). Importantly, however, in contrast to other viral vectors in gene therapy, administration of the Sindbis vectors of the invention need not be locally to the tumor. Indeed, one of the advantages of this invention is the high specificity and affinity of the vector for cancer cells, even micrometastases that cannot be resected or located by standard techniques (e.g., CAT scanning, MRI scanning, etc.).

In the therapeutic treatments of the invention, a therapeutically effective amount of the vector is administered to a patient. As used herein, the term Atherapeutically effective amount@ means an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. Specifically, a therapeutically effective amount will cause one or more of the following: apoptosis of tumor cells; necrosis of tumor cells; elimination or prevention of tumor metastases; reduction in the rate of tumor growth; reduction in tumor size or tumor shrinkage; scab formation over cutaneous tumor; elimination of the tumor; remission of the cancer; an increase in the time for reappearance of the cancer; and increased time of survival of the patient. The frequency and dosage of the vector therapy can be titrated by the ordinary physician using standard dose-to-response techniques, but generally will be in the range of from about $10^6$ to about $10^{12}$ viral vector particles per dose administered daily, weekly, biweekly, or monthly at least twice and preferably at least three times.

In order to explore if wild type Sindbis would improve the vector systems, four vectors were generated combining the helper and replicase segments of both strains (JT-BB/SP6-R; SP6-H/JT-Rep; SP6-H/SP6-R; JT-BB/JT-Rep) and tumor size reduction and survival in tumor-induced SCID mice was studied. Unexpectedly, it was found that those vectors carrying Ar-339 helper (SP6-H) were less efficient in targeting tumors than the JT vectors and that those carrying Ar-339 replicase (JT-BB/SP6-R and SP6-H/SP6-R) were more efficient in tumor reduction. To study the surprising phenotype of the helper, both viral sequences were analyzed and compared. One amino acid difference was found in the capsid protein ($Pro_{67}$ (JT-BB) to Gln (Ar-339)); three amino acid changes in envelope protein E1 ($Ala_{72}$ (JT-BB) to Val (Ar-339), $Gly_{75}$ (JT-BB) to Asp (Ar-339) and $Ser_{237}$ (JT-BB) to Ala (Ar-339)) and four changes in envelope protein E2 ($Ile_3$ (JT-BB) to Thr(AR-339); $Lys_{70}$ (JT-BB) to Glu(Ar-339); $Glu_{181}$ (JT-BB) to Lys(Ar-339) and $Val_{251}$ (JT-BB) to Ala(Ar-339)). To determine which amino acids were critical for the vector properties, different chimeras from both vectors were generated containing mixed sequences from both strains. The analysis in animal models showed that the Ar-339 E2 envelope protein sequence was primarily responsible for tumor metastases targeting although the optimum amino acid pattern was not defined. To address this question, vectors were generated containing sequences with mixed combinations of the four amino acids in E2, for JT and Ar-339, and tested by IVIS® imaging in ES-2 induced and tumor-free mouse models. Surprisingly, the change of only one amino acid from Glu to Lys at position 70 of Ar-339 E2, suppressed the ability to target metastatic tumor implants in mice and also showed no fat tissue background. This result was unexpected, considering that this mutant (Mut-1) repeatedly showed titers equivalent to the Ar-339 vector when measured in ES-2 cultured cells. Double mutant Mut-2, with K70 and V251 did not revert the targeting. Only when the whole sequence of JT E2 was substituted in the Ar-339 helper was the ability to target metastatic tumor implants recovered, a though with less intensity. Thus, residue 70 in the outer leaf of the E2 protein is essential for tumor specific targeting of vectors.

Described herein are amino acids of Sindbis viral vectors involved in specific infection of metastatic tumor implants in the mouse peritoneal cavity. Sequence analysis of cloned Ar-339 and JT viral vectors has been an important tool for the discovery of these amino acids.

The sequence analysis comparison with the published Strauss sequence, revealed 2 or 3 amino acid changes in viral replicase for JT and Ar-339 respectively. The Ar-339 nsP1 Ile 441 is a reverse mutation to an alphavirus conserved residue; this amino acid may also be related to viral adaptation to BHK-21 tissue culture. Ar-339 replicase is more efficient in suppression of disease progression than JT, the change from polar Cys in JT to aliphatic residue, Ile 441, may play a role in enhancing replicase activity. Interestingly, both JT and Ar-339 vectors have the same 2 amino acid changes in nsP2 protein versus the Strauss sequence. JT and Ar-339 nsP2 residues are more conserved among the Sindbis-like Alphavirus group.

Comparing the Strauss sequence with the region coding for the structural part of the JT and Ar-339 vectors, the changed amino acids were found mainly in the viral spike, although in different residues, suggesting a different evolutionary lineage of both strains. E1 D75 and A237 of Ar-339 are highly conserved in Sindbis-like alphaviruses; all viruses in this group carry D75. There is no virus in the group that has serine at 237, which only occurs in the JT vector. These data suggest that E1 G75 and S237 of JT vector may more likely be point mutations that arose in this laboratory strain. Further studies with E1 mutants should reveal the implication of these E1 residues in the specific tumor targeting of the viral vector. Most of the sequence variabilities have been found at the E2 envelope protein in the leaf-like domain at the viral spike; these residues are also poorly conserved in the Sindbis-like alphavirus group. The role of these E2 spike mutations in mouse tumor models in vivo was examined.

The fact that the Mut-1 vector shows the same titer as the Ar-339 vector in ES-2 cells, but does not efficiently infect ES-2 metastatic tumor implants in mice, represents a powerful tool for the study and the improvement of Sindbis vectors for gene therapy. One cause of the loss of tumor targeting in vivo could be a reduced stability of the vector in mice. Alignment of protein sequences among 17 different viruses of the Sindbis-like alphavirus group showed that ten out of the 17 members have a gap in Sindbis E2 residues 68-71, including Semliki Forest virus (SFV) which has a comparable structure to Sindbis virus. The viral spike is composed of three E1-E2 heterodimers that lean against each other. There is a gap between the base of neighboring E1-E2 heterodimers which would allow E2 to move out of the center of the spike during fusion (Zhang et al. 2002). In addition, previous studies with stable deletion mutants in the E2 receptor binding domain, also show equivalent in vitro titers but drastic reduction of infectivity in live *Aedes aegypti* mosquitoes (Myles et al. 2003). Without wishing to be bound by theory, it is believed that these data suggest that there is structural flexibility in this area of the spike, therefore, alterations in residue 70 shouldn't be critical for Mut-1 vector stability in vivo. The loss of vector infectivity would be more likely to occur via a decrease in cell binding affinity, especially in vivo, where the environmental conditions for vector infection are more restrictive.

In Sindbis and Semliki Forest virus (SFV), the residues involved in host cell fusion and binding to cellular receptors are located in the viral spike. It has been described that only one change from the small non-polar Valine, at position 75, to the acidic Aspartic acid in E1 SFV spike subunit, modifies the cell-cell fusion properties of the virus (Levy-Mintz and Kielian, 1991). Amino acids in these E1 and E2 spike domains are, thus, important in spike configuration and virus infectivity.

The vector Ar-339, having hydrophobic (V72), and acidic (D75) residues in E1 and a glutamic acid (E70) in E2 protein, is able to efficiently target tumor cells in vivo. In Mut-1, in which E2 residue 70 is changed to lysine, there is a change in polarity and charge of the amino acid that would change the conformation of the spike and so the cell binding properties of the vector. This hypothesis is supported by the difference in cell tropism observed in vitro between Mut-1 and Ar-339. Only the recovery of the full sequence of JT-BB E2 in Mut-4 results in higher titers in BHK-21 cells. If these differences were observed in vitro, where the conditions for cell binding are optimized, it is possible that in vivo factors involved in cell-vector interactions might be able to prevent vector adherence to the viral receptor. Ar-339 and Mut-1 vectors have the same titer in ES-2 cells in vitro, but in mouse metastatic implants, where ES-2 cells are in a different environments and could have receptor variations, small affinity differences between both vectors are revealed.

The present invention is described further below in examples which are intended to describe the invention without limiting the scope thereof.

In the examples below, the following materials and methods were used.

Example 1

Sindbis cDNA Cloning

Common Techniques
Virus Provocation

Sindbis virus strain Ar-339 (Original) was obtained from ATCC (Manassas, Va., Item #VR-68) and propagated on a secondary chicken embryo fibroblast cell line, CEF. Cells were cultured in EMEM media (BioWhittaker, cat#12-684) supplemented with 10% Fetal bovine sera, $NaHCO_3$ 1.5 g/l; 1-Glutamine, 292 mg/l and Penicillin/Streptomycin, 100 U/ml. Two T-75 flasks with 80% confluent CEF cell monolayers, were infected with $2.5 \times 10^7$ pfu and $5 \times 10^7$ pfu, respectively, of Sindbis virus Ar-339, diluted in 1 ml of Opti-Mem I media (GIBCO-BRL Invitrogen, San Diego Calif.; cat#31985-070) supplemented with 0.7 µM $CaCl_2$. Virus-infected cells were incubated at 37° C. for 1 h, 10 ml of EMEM media/flask added, and cells were incubated overnight at 37° C. Supernatants containing the Sindbis "innocula" were harvested and stored at −80° C. until used in further infections. CEF cells were collected for total RNA extraction.

RNA Extraction

5 T-75 flasks with 90% confluent CEF monolayers were incubated 1 h at 37° C. with 1:100; 1:20; 1:10; and 1:5 dilutions (in Ca-OPTI-MEM media) of previously obtained "Sindbis innocula". Ten ml of EMEM media/flask was then added and incubated overnight at 37° C. After collecting the supernatant, 2 ml of Trizol (Invitrogen, San Diego, Calif.; cat #15596-018) per flask was added to the infected cells, the extract collected and stored at −80° C. Total RNA from infected cells was prepared following the manufacturer's (Trizol) protocol. Briefly, 1 ml of Trizol cell extract was vortexed for 15 seconds, 200 µL of chloroform added, vortexed, spun at 15,000 g for 10 min at room temperature (rt), the aqueous upper phase transferred to a clean tube, 750 µL of isopropanol added, incubated at rt for 15 min, spun again, the supernatant removed and the pellet washed with ethanol (70% in DEPC water). The pellet was air dried at rt for 5-10 min, and resuspended in 50 µL of DEPC water.

Figure 1:
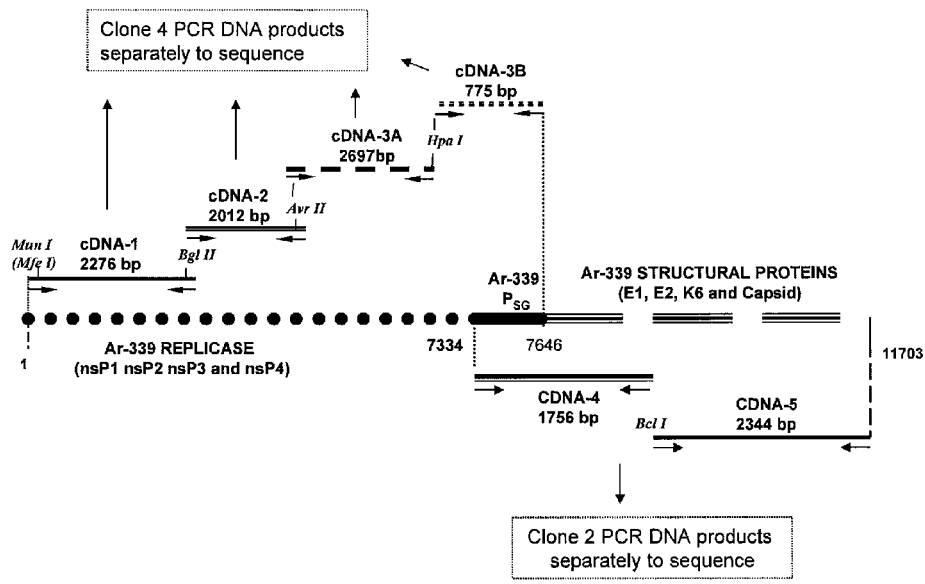
FIG. 1 Sindbis virus Ar-339 cDNA cloning.

Sindbis c-DNA Cloning. Sindbis virus RNA was cloned in 6 overlapping fragments (CDNA-1, CDNA-2, CDNA-3A, CDNA-3-B, CDNA-4 and CDNA-5) into sequencing plasmid pCR4Blunt-TOPO (Invitrogen, San Diego Calif.; cat#45-0245). The position of the fragments is shown in FIG. 1 and the sequences of the primers used are shown in Table I (Appendix A). The primers were designed to take advantage of the unique restriction sites of the virus. In primer SV-C3R RE XbaI was introduced to allow CDNA-3 cloning. For each fragment the RT and the PCR reactions were performed with the same pair of primers. The cloning procedure was the same for all of the fragments except for the conditions of the PCR cycles.

Reverse transcriptase (RT) reactions were performed with: 5 µg from total RNA from infected cells, reaction buffer (1×);

forward and reverse specific primers (2.5 µM/each); dNTPs (1 mM): DTT (5 mM) and 15 u of ThermoScript™ RNase H-Reverse Transcriptase (Invitrogen, cat#12236-014), in a final volume of 20 µL. RT was diluted 1:1 in distilled water prior to use in PCR.

The Pfx-PCR reactions were performed with 1 µL of RT reaction, reaction buffer (1×), $MgSO_4$ (1 mM), dNTPs (0.3 mM/each), forward and reverse primers (0.3 µM/each) and 1 U Platinum Pfx DNA Polymerase (Invitrogen, cat#11708-013) in final volume of 25 µl. RT and PCR reactions were performed in an Eppendorf "Mastercycler Gradient" Thermal Cycler. Taq-PCR reactions contained reaction buffer (1×); dNTP's (200 µM), forward and reverse primers (0.5 µM/each) and 1 u Taq-DNA-polymerase (Fisher Scientific, Pittsburgh, Pa., cat#FB 600025) in a final volume of 20 µl. In both cases PCR products were analyzed by electrophoresis in 1% agarose gels and DNA bands cut out and purified with a QIAEXII gel extraction kit (Qiagen, Valencia Calif.; cat#20021)

All enzymes were purchased from New England Biolabs (NEB, Beverly, Mass.). After digestions with restriction enzymes (RE), extracted DNAs were CIP dephosphorylated (1 h at 37° C.) and/or phosphorylated with T4-Polynucle-otide-Kinase (1 h, 37° C.), enzymes were inactivated (70° C., 10 min or 65° C. 20 min) and reactions were run in 1% agarose gels. Bands were cut out, extracted, and quantified by gel electrophoresis by comparison with bands of known DNA concentration. Ligations were carried out with T4-DNA-Ligase (NEB) (16° C. 14 h) or with the Quick ligation kit (NEB) (5 min at room temperature (rt)). Transformations were performed using RapidTrans™ TAM1 extra competent E. coli (Active Motif, Carlsbad, Calif.; cat#11099). After transforming E. coli with the ligations, the first screening of positive bacteria was done by Taq-PCR of E. coli colonies. Positive plasmids were checked by restriction enzymes. Sequencing was done at the Skirball Institute of Biomolecular Medicine, NYU.

CDNA-1 plasmid. RT reaction was performed with primers CDNA-1F/CDNA1-R at 55° C. 1 h. Two Pfx-PCR were performed: 94° C. 5 min; 35 cycles [94° C. 30 s; 66° C., 30 s (band D) or [67° C., 30 s; 72° C., 2.5 min and 72° C., 2.5 min] (band E). PCR products were run in 1% agarose gels and both 2.2 Kb bands, D and E, were isolated and cloned separately into the pCR4Blunt-TOPO plasmid. Positive colonies were screened using the same PCR conditions with 65° C. as the annealing temperature and Taq-DNA-Polymerase. Two plasmids were selected (one from each PCR band) and the PCR band D in plasmid CDNA-1_Topo#64 was completely sequenced. The sequence was compared to the Ar-339 sequence published by Strauss et al., *Virology* 133, 1984. The differences found were compared with the sequences of PCR band E. Identical differences were found in bands D and E to confirm that they came from the virus and not from PCR mutations.

CDNA-2 plasmid. The Reverse transcriptase reaction was performed with primers CDNA-2F/CDNA-2R for 1 h at 55° C. Three PCR in gradient 94° C., 5 min; 35 cycles of [94° C., 30 s; 64.7° C., 30 s (band 1); or 66° C., 30 s (band 2); or 67° C., 30 s (band 3); 72° C., 2.5 min] and 72° C., 2.5 min. After cloning the 2 kb bands separately in pCR4Blunt-TOPO, PCR screening of colonies was done at an annealing temperature of 64.5° C. Band 2 in plasmid CDNA-2#213 was fully sequenced, and any mutations found were checked by comparison with the sequences of PCR bands 1 and 3.

CDNA-3A plasmid. Three RT reactions were performed in gradient with primers CDNA-3F/SV-6932R at 53.2° C., 55.5° C. and 60.8° C. respectively for 1 h 30 min. Three Pfx PCR were performed with 1 µL of each RT, respectively: 94° C., 5 min; 35 cycles of [94° C., 30 s; 53° C., 30 s; 72° C., 3 min] and 72° C. 3 min. The 2.68 kbp bands T, U and V were cloned separately and band V in plasmid C3A_Topo#735 was fully sequenced. No changes were found compared with the published Ar-339 sequences (Strauss et al. 1984).

CDNA-3B plasmid. RT reaction was performed with primers SV-6882F/SV-C3R at 60.8° C. for 1 h 30 min. Three Pfx-PCR in gradient were performed with 94° C., 5 min; 35 cycles of [94° C., 30 s; 55.3° C., 30 s (band J); or 56° C., 30 s (band K); or 58.3° C. 30 s (band L); 72° C., 1 min] and 72° C., 2 min. The three 774 bp bands were cloned separately and band L, in plasmid C3B-Topo#334, was fully sequenced. The mutations found were confirmed by sequencing bands J and K.

CDNA-3 (CDNA-3A+3B) plasmid. HpaI RE is not unique in the Sindbis sequence, so in order to clone CDNA3A and CDNA3B fragments into the new reporter vector, it was necessary to generate first a Topo plasmid containing both sequences, and then clone fragment CDNA-3 (CDNA-3A+3B) in the AvrII/XbaI site. Plasmid C3B-Topo#334 was HpaI and SacI digested and the 774 bp viral band was isolated from the agarose gel and ligated (T4-DNA-Ligase 16° C. 14 h) to HpaI/SacI digested C3A_Topo#735 plasmid. Transformants were screened by PCR with Taq-Polymerase, and primers CDNA-3F, SV-C3R at: 94° C., 10 min; 35 cycles of [94° C. 30 s; 55° C., 30 s; 72° C., 3 min] and 72° C. 2 min. The positive plasmid was named C3A+B_Topo#810, and the junctions were sequenced.

CDNA-4 plasmid. The RT reaction was performed with primers CDNA-4F/CDNA4-R at 52° C. for 1 h 30 min. Three PCRs were performed in gradient with 94° C., 5 min; 35 cycles of [94° C., 45 s; 49.7° C., 30 s (band M); or 55° C., 30 s (band N); or 57.2° C., 30 s (band O); 72° C. 2.5 min] and 72° C. 2.5 min. The 2 kbp bands were isolated and cloned separately, band N in plasmid CDNA-4_Topo#422 was fully sequenced. The mutations found were confirmed by sequencing bands M and O.

CDNA-5 plasmid. RT reactions performed with primers CDNA-5F/CDNA5-R at 49.7° C. for 1 h 30 min. Three PCR were made in gradient with 94° C., 5 min; 35 cycles of [94° C., 30 s; 46.8° C., 30 s (band Q); or 48.6° C., 30 s (band R); or 50.5° C., 30 s (band S); 72° C. 2 min] and 72° C., 2 min. The 2.35 kbp bands were cloned separately and band S in plasmid CDNA-5_Topo#525 was fully sequenced. The mutations found were confirmed by sequencing bands Q and R. Vectors construction.

Polylinker cloning in pUC plasmid. In summary, the SP6 and T7 Polylinker bands were constructed out of primers in two fragments, a 5' end containing the SP6 promoter (primer pairs Poly1-SP6(+)/Poly-2(−)) or T7 promoter (primers Poly1-T7(+)/Poly-2(−)) and a common 3'end (primers Poly-3(+)/Poly-4(−)) the sequences of the primers are given in Table II (Appendix A). 5' and 3' bands were digested and ligated to generate the polylinker and then were ligated to the AflIII/AatII pUC band containing the E. coli replication origin and Ampicillin resistance gene to generate T7-pUC or SP6-pUC plasmids.

T7-pUC plasmid. Two separate reactions were performed with primers pairs Poly1-T7(+)/Poly-2(−) or Poly-3(+)/Poly-4(−). For both reactions, conditions were: primers (5 µg each), buffer (1×), dNTPs (1.5 mM), BSA (50 µg/ml). Mixes were boiled for 5 min and cooled down to room temperature for primer annealing, 3 units/reaction of T4-DNA-Polymerase was then added to a final volume of 20 µl, and incubated at 37° C., for 30 min for chain extension. 0.5 µL of each reaction was used as a template in two PCR reactions: one with template Poly1-T7(+)/Poly-2(−) and primers PCR-Poly1-F/PCR-Poly2-R and other with template Poly-3(+)/Poly-4(−) and primers PCR-Poly-3F/PCR-Poly-4R. For both PCRs, the conditions were: reaction buffer (1×), dNTP's (200 µM), forward and reverse primers (0.5 µM/each) and 1 unit of Taq-DNA-polymerase in a final volume of 20 µl. For each primary reaction, 3 secondary tubes were prepared and PCR reactions were performed in gradient for annealing temperature: 94° C., 5 min; 35 cycles of [94° C., 30 s; 40° C., 30 s (tube 1); or 45.4° C., 30 s (tube 2); or 50.7° C., 30 s (tube 3); 72° C., 30 s] and 72° C. 1 min. Bands were stronger for the 40° C. annealing temperature. The 145 bp bands were then isolated and digested with enzymes: AflIII and XbaI for PolyT7/Poly2-R and, AatII and XbaI for Poly3(+)/Poly 4(−). After inactivating the enzymes at 65° C. 20 min, the ligation of equimolar amounts of both bands was carried out at 25° C. for 1 h with $T_4$-DNA-ligase. The 1811 nt AatII/AflIII band of the pUC plasmid was added, and incubated at 16° C. overnight. *E. coli* Tam1 competent cells were transformed with the ligations and positively selected colonies screened by double digestion with AatII and AflIII. The positive plasmid was named T7-pUC#32 and was checked by sequencing.

SP6-pUC plasmid. The reaction mix: Poly1-SP6(+) and Poly-2(−) primers (5 µg each), buffer (1×), dNTPs (1.5 mM), BSA (50 µg/ml), was boiled for 5 min and cooled down to rt for primer annealing. Then 3 units/reaction of T4-DNA-Polymerase was added to a final volume of 20 µl, and incubated at 37° C., 30 min. 0.5 µl/Rxn was used as a template in a gradient PCR reaction with PCR-Poly1-F/PCR-Poly2-R primers (0.5 µM/each) reaction buffer (1×), dNTP's (200 µM), and 1 unit of Taq-DNA-polymerase in a final volume of 20 µl. PCR conditions: 94° C., 5 min; 35 cycles of [94° C., 30 s; 40° C., 30 s (tube 4); or 45.4° C., 30 s (tube 5); or 50.7° C., 30 s (tube 6); 72° C., 30 s] and 72° C. 1 min. Bands were isolated in agarose gels, pooled together and purified. The DNA obtained was digested with enzymes AflIII and XbaI for 2 h at 37° C. After inactivating the enzymes at 65° C., 20 min, the digested DNA band was ligated to the AatII and XbaI digested Poly-3(+)/Poly-4(−) band at 25° C. for 1 h with T4-DNA-ligase. Five µL of the ligation was used as the template for a second gradient PCR reaction carried out with primers PCR-Poly1-F and PCR-Poly4-R, (same concentrations as previous PCR) and cycles: 94° C. 2 min, 18 cycles of [94° C., 30 s; 40° C., 30 s (tube 4); or 43.1° C., 30 s (tube 5); or 45.4° C., 30 s (tube 6); 72° C. 30 s] and 72° C. 1 min. Bands were isolated in an agarose gel, pooled together, purified and AflIII/AatII digested at 37° C. for 16 h. After enzyme inactivation (65° C., 20 min), the AflIII/AatII SP6 band was ligated to the 1811 nt AatII/AflIII band of the pUC plasmid with Quick T4-DNA-ligase (New England Biolabs) at rt for 5 min and transformed into *E. coli* Tam1 cells. Screening of colonies was performed as for T7 polylinker. The plasmid was named SP6-pUC#51.

T7-pUC-PolyA#114 plasmid. The Sindbis 3' end from nt 11392 to 11694 was obtained by PCR on plasmid CDNA-5_Topo #525 with primers: PolyA-F (5' CCCCAATGATCCGACCA 3") (SEQ ID NO:1) and PolyA-R (5' AAAACAAATTTTGTTGATTAATAAAAG 3') (SEQ ID NO:2). PCR conditions: reaction buffer (1×), $MgSO_4$ (1 mM), dNTPs (0.3 mM each), primers (0.3 µM each) and 1 unit of Platinum Pfx DNA Polymerase in a final volume of 25 µl. Three PCR reactions were performed in gradient for annealing temperature: 94° C., 5 min; 35 cycles of [94° C., 45 s; 53.2° C., 30 s (tube 1); or 55.5° C., 30 s (tube 2); or 60.8° C., 30 s (tube 3); 72° C. 45 s] and 72° C. 1 min. The 53.2° C. band was stronger and its DNA was isolated from the gel, phosphorylated with 10 units of T4-Polynucleotide-Kinase (Biolabs) at 37° C., 30 min. After inactivation at 70° C. 10 min, the DNA was ligated to plasmid T7-pUC#32 (previously digested with HpaI and dephosphorylated) using $T_4$-DNA-ligase at 16° C. for 14 h. Screening of recombinants was performed by PCR of colonies using the same primers, Taq-Polymerase and cycles: 94° C., 5 min; 35 cycles of [94° C., 45 s; 53° C., 30 s; 72° C., 45 s] and 72° C. 1 min. The orientation of the insert was analyzed with restriction enzymes AflII/AseI. The positive plasmid was confirmed by sequencing, and named T7-pUC-PolyA#114. From this vector the final vector T7-ARep#68 and SP6-pUC-PolyA#914 was generated to construct the final vector SP6-Arep#68.

Replicon vector constructions. T7-ARep plasmid: Viral cDNA fragments CDNA-1, CDNA-2, and CDNA-3 were cloned in T7-pUC-PolyA#114 to generate a new reporter vector T7-ARep#68. Plasmid CDNA-1_Topo#64 was digested with MfeI and BglII RE and the 2247 bp viral band isolated and ligated, with the quick ligase kit, to T7-pUC-PolyA#114, MfeI, BglII digested and CIP dephosphorylated. TAM1 transformant bacteria were screened by PCR with Taq-Polymerase and primers CDNA-1F and CDNA-1R at: 94° C. 10 min, 35 cycles of [94° C., 30 s; 65° C., 30 s; 72° C. 2.5 min] and 72° C. 2 min. The positive plasmid was named T7-pUC-PolyA-C1#11 and was AvrII/BglII digested and CIP dephosphorylated and ligated, with Quick ligase, to the CDNA-2 1950 bp viral band, obtained after AvrII/BglII digestion of plasmid CDNA-2_Topo#213. Screening of positive colonies was made by PCR with Taq polymerase and primers CDNA-2F and CDNA-2R at: 94° C., 10 min; 35 cycles of [94° C., 30 s; 64° C., 30 s; 72° C. 2.5 m] and 72° C. for 3 min. The plasmid was named T7-pUC-PolyA-C1-C2#35. C3A+B_Topo#810 was digested with XbaI/AvrII and BsshII, the 3350 nt viral C3 band separated in an agarose gel, isolated and ligated (Quick Ligase Kit) to XbaI/AvrII digested T7-pUC-PolyA-C1-C2#35 plasmid. Transformants were analyzed by XbaI/AvrII digestion. The new reporter vector was named T7-ARep#68, and was fully sequenced.

SP6-ARep plasmid. The reporter vector under the SP6 promoter was cloned in three steps. First, the SP6 promoter was cloned into T7-pUC-PolyA#114, then CDNA-1 was inserted and in the last step, the CDNA-2+CDNA-3 band from T7-ARep#68 was cloned.

SP6-pUC#51 was SphI and AflIII digested and the 154 nt band isolated and ligated (T4-DNA-ligase) to the T7-pUC-PolyA#114 SphI/AflIII/CIP band. Plasmids were screened by MboII digestion and checked by sequencing. The positive plasmid was named SP6-pUC-PolyA#902, and was digested with MfeI and BglII, CIP dephosphorylated and ligated (quick ligase) to the MfeI/BglII CDNA-1 band. Colonies were analyzed by PCR with CDNA-1F/CDNA-1R primers at: 94° C. 10 min, 35 cycles of [94° C., 30 s; 65° C., 30 s; 72° C., 2.5 min] and 72° C. 2 min. The positive plasmid was also analyzed by MfeI/BglII digestion and named SP6-pUC-PolyA-C1#306. Plasmid T7-ARep#68 was BglII/XbaI digested, and a 5.6 kb CDNA-2+CDNA-3 band was isolated from an agarose gel and ligated to BglII/XbaI/CIP digested SP6-pUC-PolyA-C1#306 plasmid. Screening was done by BglII and BglII/XbaI digestions. The new vector was named SP6-Arep#701.

Helper vector constructions. T7-AH#17 plasmid. In a first step Sindbis virus nts 1 to 425 were cloned into T7-pUC-PolyA#114. In a second step, both CDNA-4 and CDNA-5 viral fragments were cloned to generate a new helper vector. Sindbis nt 1 to 425 were amplified by PCR using as a template 54 ng of CDNA-1_Topo#64, primers (0.5 µM/each) SIN1-19F (5' ATTGACGGCGTAGTACACA 3') (SEQ ID NO:3) and H-BamR (5'GTATCAAGTAGGATCCGGAG 3') (SEQ ID NO:4) which adds a BamHI RE to allow CDNA-4 fragment cloning, reaction buffer (1×), dNTP's (200 µM), and 1 unit of Taq-DNA-polymerase in final volume of 20 µl. Two PCR reactions were performed in gradient for the following annealing temperature: 94° C. 5 min, 28 cycles of [94° C., 30 s; 45.3° C., 30 s (tube 1); or 46.4° C., 30 s (tube 2); 72° C., 30 s] and 72° C. 1 min. Bands were analyzed in agarose 1.3% gels, extracted, pooled together and digested with MfeI/BamHI. Plasmid T7-pUC-PolyA#114 was MfeI/BamHI digested and CIP dephosphorylated, the band isolated from an agarose gel and ligated to the 350 bp MfeI/BamHI PCR band. Colonies were screened by Taq-PCR with primers SIN1-19F/H-BamR at: 94° C., 10 min; 45 cycles of [94° C., 30 s; 45° C., 30 s; 72° C. 30 s] and 72° C. 1 min. A positive plasmid was checked by sequencing and named T7-pUC-PolyA-5'#604. This plasmid was digested with BamHI and NsiI and CIP dephosphorylated to ligate with viral inserts.

The ligation of CDNA-4 and CDNA-5 was through RE BclI. This enzyme is dam methylation dependent, so to demethylate the DNA, plasmids harboring CDNA-4_Topo#422 and CDNA-5_Topo#525 were transformed into dam⁻/dcm⁻ E. coli strain GM2163 (New England Biolabs). CDNA-4_Topo#422(dam−) was BamHI and BclI digested and plasmid CDNA-5_Topo#525 was digested with BclI and NsiI. In both cases, the enzymes were inactivated at 70° C. for 15 min. The ligation was performed with T4-DNA-Ligase (16° C. for 14 h) with equimolar amounts of the three bands: T7-pUC-PolyA-5'#604 (BamHI/NsiI/CIP), CDNA-4_Topo#422 (dam⁻) (BamHI/BclI) and CDNA-5_Topo#525(dam⁻)(BclI/NsiI). Colonies were screened by BamHI and NsiI digestion. The positive plasmid was named T7-AH#17 and was fully sequenced.

SP6-AH plasmid. Plasmid SP6-pUC-PolyA#902 was digested with MfeI and NsiI, CIP treated and the 2.4 kb band was ligated (T4-DNA-ligase) to the 4.5 kb T7-AH#17 MfeI/NsiI band. Colonies were screened by Taq PCR with primers CDNA-5F and CDNA-5R at: 94° C., 10 min; 25 cycles of [94° C., 30 s; 53° C., 30 s; 72° C. 3 min]. Positive plasmids were checked by NsiI, and NsiI/MfeI digestions and sequenced. The resulting plasmid was named SP6-AH#318

T7-R AND SP6-R plasmids. The four plasmids (SP6-AH#318, SP6-ARep#701, T7-AH#17 and T7-ARep#68) were fully sequenced, and in all four, a deletion of one T at the 3' end of the virus before the polyA, nt 11686 was found. In order to have the same sequence as the virus Ar-339, the deletion was fixed.

The Ar-339 sequence was placed first in plasmid T7-pUC-polyA#114. The new 3' end was obtained by PCR with primers: PolyA-F (5' CCCCAATGATCCGACCA 3") (SEQ ID NO:5) and END-R (5' AAAACAAAATTTTGTTGATTAATAAAAG 3') (SEQ ID NO:6) and cloned into T7-pUC#32, as described previously for T7-pUC-polyA#114 cloning. The new plasmid T7-pUC-3end#9 was sequenced and used to generate new helpers and reporters.

To generate the reporter vectors, the T7-pUC-3end#9 plasmid was digested with XbaI and XhoI and the 423 bp band was cloned into the SP6-Arep#701 XbaI/XhoI 9504 bp band and into the T7-ARep#68 XbaI/XhoI 9504 bp band to generate new reporters SP6-R#406 and T7-R#202, respectively.

T7-H AND SP6-H plasmids. Plasmid T7-pUC-3end#9 was digested with NsiI and XhoI and the 311 bp band was cloned into the SP6-AH#38 NsiI/XhoI 6399 bp band and into the T7-AH#17 NsiI/XhoI 6399 bp band, to generate, respectively, the new helpers SP6-H#432 and T7-H#226. The new reporters and helper plasmids were fully sequenced.

SP6-HE2 mutants. Mutants were made on SP6-H plasmid following the kit QuickChange IIx site-directed mutagenesis (Stratagem, La Jolla, Calif.). Briefly, 10 ng of SP6-H#432 were incubated with complementary primers: E2-I3-F/E2-I3-R or E2-K70-F/E2-K70-R or E2-E181-F/E2-E181-R or E2-V251-F/E2-V251-R, reaction buffer, dNTPs and 2.5 units of pfuUltra HF DNA polymerase. PCR reactions were 95° C. 1 min, 18 cycles of: 95° C. 50 s, 60° C. 50 s, 68° C. 7 min, and final elongation of 68° C. 7 min.

After the PCR reactions 10 U of restriction enzyme DpnI was added and reaction incubated 37° C. 1 hour to digest methylated parental DNA. XL-10-Gold competent E. coli cells were transformed and the colonies analyzed by restriction enzyme digestion (RE). Mutations were verified by sequencing. Multiple mutants were made following the same protocol using previous mutants as template for PCR. The sequence of primers used and nt changes are shown in Table III (Appendix A). Plasmids made: SP6-H-I3#5; SP6-H-K70#59; SP6-H-I3-K70#66; SP6-H-I3-K70-E181#3; SP6-H-K70-V251# SP6-H-I3-K70-E181-V251. In order to make sure that there were not additional mutations due to the PCR technique, the 1270 bp BssHII/BanII fragment of each clone was subcloned in the sequenced plasmid SP6-H.

Reporter gene cloning in replicon vectors. The LacZ gene was cloned in the PmlI/XbaI site of vectors SP6-ARep#701, SP6-R#406, T7-ARep#68 and T7-R#202 to generate SP6-ARepLacZ, SP6-RLacZ, T7-ARepLacZ and T7-RLacZ, respectively.

The firefly luciferase gene was excised at the NheI/XbaI sites from pGL3 plasmid (Promega Co, Madison Wis.) and cloned in the XbaI site of vectors: SP6-ARep#701, SP6-R#406, T7-ARep#68 and T7-R#202 to generate SP6-ARep-Fluc, SP6-RFluc, T7-ARepFluc and T7-RFluc, respectively.

The *Renilla* luciferase gene from plasmid phRL-CMV (Promega Co, Madison Wis.) was cloned in the XhaI site of the replicons, to generate plasmids: SP6-RhRluc and T7-RhRluc.

Example 2

Cells. BHK-21, and ES-2 cells were obtained from the American Type Culture Collection (ATCC). BHK-21 cells were maintained in αMEM (JRH Bioscience) with 5% FBS. ES-2 cells were derived from a patient with clear cell carcinoma, a type of ovarian cancer that has a poor prognosis and is resistant to several chemotherapeutic agents including cisplatin. ES-2 cells were cultured in McCoy's 5A medium (Mediatech) with 5% FBS. All basal media were supplemented with 100 μg/ml of penicillin-streptomycin and 0.5 μg/ml of amphotericin B (both from Mediatech). ES-2/Fluc cells were derived from the ES-2 line by transfection of a plasmid, pIRES2-Luc/EGFP, that expresses a bicistronic mRNA transcript containing both firefly luciferase and EGFP genes. To construct the pIRES2-Luc/EGFP plasmid, a DNA fragment containing the luciferase gene was obtained from pGL-3 basic plasmid (Promega) and then subcloned into the multicloning sites of the pIRES2-EGFP plasmid (BD Biosciences Clontech).

The mouse ovarian MOSEC cell line (clone ID8) was a generous gift from Dr. Katherine F. Roby (University of Kansas Medical Center, Kansas City) and was maintained in Dulbecco's modified Eagle's medium (DMEM) supplemented with 4% FBS and 1× insulin-transferrin-selenium (Mediatech, Inc).

In vitro transcription and vector preparation. The plasmids carrying the Sindbis replicon or JT-BB helper RNAs were linearized with PacI, NotI or XhoI, before in vitro transcription using the mMESSAGE mMACHINE RNA transcription kit (T7 and SP6 version; Ambion). Both helper and replicon RNA transcripts (20 µl each) were then electroporated into BHK-21 cells and incubated in 10 ml of αMEM containing 5% FBS at 37° C. for 12 h. The medium was replaced with 9 ml of Opti-MEM I medium (GIBCO-BRL, Invitrogen San Diego Calif.) supplemented with 0.7 µM $CaCl_2$. After 24 h, the culture medium was collected and stored at −80° C.

Vector titering. The titers of Sindbis vectors were assayed in BHK-21, ES-2, ES-2/Fluc or MOSEC cells. Serial dilutions (300 µL each) of vector were added to $2 \times 10^5$ BHK-21 cells in 12-well plates. After incubation for 1 hour at room temperature, the cells were washed with PBS and incubated with 2 mL of αMEM at 37° C. for 24 hours.

LacZ expression was determined by two methods: staining and counting blue cells/well or reading absorbance. For the first, cells were fixed in PBS containing 0.5% glutaraldehyde at room temperature for 20 minutes, washed three times with PBS, and then stained with PBS containing 1 mg/mL X-gal (5-bromo-4-chloro-3-indolyl-D-galactopyranoside; (Fisher Scientific, Pittsburgh, Pa.), 5 mM potassium ferricyanide, 5 mM potassium ferrocyanide, and 1 mM MgSO4 at 37° C. for 3 hours. After staining with the X-Gal solution, cells that expressed LacZ were blue. Blue-stained cells were counted and vector titers were estimated by determining the number of transducing units (TU) per mL of aliquot. With the second method, cells were lysed with 200 µL of M-PER lysis buffer (Pierce Biotechnology, Rockford, Ill.). 50 µL of the cell lysates were added into 50 µL of All-in-One-Galactosidase Assay Reagent (Pierce Biotechnology) and incubated at room temperature for 5 minutes before reading at 405 nm. Vector titers were estimated as the last dilution having detectable absorbance.

Firefly luciferase activity in cell lysates was determined by aspirating the culture medium from the wells and adding 200 µL per well of culture medium and 200 µL per well of Steady-Glo™ reagent (Promega Corp., Madison, Wis.). Plates were incubated with gentle rocking for 5 minutes until the cells detached from the plates. The cell lysates were then transferred to 12×47 mm cuvettes (BD Pharmingen, San Diego, Calif.), and the luciferase activity of each lysate was determined by taking a 30-second reading with a LUMI-ONE portable luminometer (Bioscan, Inc., Washington, D.C.).

*Renilla* luciferase activity was determined by following the protocol in "*Renilla* Luciferase assay system" (Promega Corp., Madison, Wis.). Briefly, cells were washed with PBS and 250 □l/well of lysis buffer was added. 20 µL of substrate were added to 100 µL of extract and the luciferase activity of each lysate was determined by taking a 30-second reading with a LUMI-ONE portable luminometer (Bioscan, Inc., Washington, D.C.).

Animal models. All animal experiments were done in accordance with NIH and institutional guidelines. To determine the therapeutic effects of Sindbis virus vectors, SCID mice (female, 6-8 week old; Taconic, Germantown, N.Y.) were i.p. injected with $1.5 \times 10^6$ ES-2/Fluc cells/mouse on day 0 and imaged with the IVIS® system the next day (day 1) to confirm the presence of tumor cells. Then on day 4, 5 mice/vector received i.p. treatment with vectors carrying the *Renilla* luciferase: A (JT-BB/SP6-RhRluc), B (SP6-H/JT-RephRluc), C (SP6-H/SP6-RhRluc), D (JT-BB/JT-RephRluc). All vectors had the same titer in ES-2/Fluc cells, and mice were i.p. injected daily with $\sim 10^6$ TU in 0.5 ml Opti-MEM l/mouse. Control mice (n=5) received no Sindbis vector treatment. Disease progression was later determined by IVIS® imaging on days 1, 5, 9 and 13.

Survival curves were compared with log rank test. All the P values presented in this study are two-tailed.

For colocalization experiments, two SCID mice/vector were i.p. inoculated with $2 \times 10^6$ ES-2/Fluc cells on day 0 and received one i.p. treatment of vector C ($\sim 10^6$ TU in 0.5 mL of OptiMEM I) on day 5. The next day (day 6), mice were i.p. injected with 0.3 mL of 0.2 mg/mL coelenterazine (Biotium, Inc., Hayward, Calif.) followed by IVIS® imaging for *Renilla* luciferase activity. 30 minutes later, the same mice were i.p. injected with 0.3 mL of 15 mg/mL D-luciferin (Biotium, Inc) and a second IVIS® imaging for Firefly luciferase activity was performed.

Cell tropism experiments, were done in two groups of SCID mice with 5 mice/vector: one without tumor induction and the second one in mice with induced tumors.

The tumor free animals were i.p. injected with Fluc vectors on day 0, imaged by IVIS® on day 1, received a second injection of vectors on day 2 and on day 3 were IVIS® imaged again.

For the second group, SCID female mice were injected i.p. on day 0 with $2 \times 10^6$ ES-2 cells/mouse and on day 4 mice were injected with vectors carrying the luciferase reporter genes. After the first whole-body IVIS® imaging on day 1, the peritoneum was removed for another IVIS® imaging of the peritoneal cavity. The remaining mice of the group, except one for background control, had a second i.p. injection of vectors on day 6 and imaged again on day 7.

In vivo bioluminescence detection with the IVIS® Imaging System. A cryogenically cooled IVIS® Imaging System Series 100 (Xenogen) was used with Living Image acquisition and analysis software (Version 2.11, Xenogen Corp. Alameda, Calif.) to detect the bioluminescence signals in mice. For firefly luciferase detection, each mouse was injected i.p. with 0.3 ml of 15 mg/ml beetle luciferin (potassium salt; Promega Corp., Madison, Wis.) in PBS. After 5 min, mice were anesthetized with 0.3 ml of avertin (1.25% of 2,2,2-tribromoethanol in 5% tert-amyl alcohol) or isofluran-mixed oxygen. The imaging system first took a photographic image in the chamber under dim illumination; this was followed by luminescent image acquisition. The overlay of the pseudocolor images represents the spatial distribution of photon counts produced by active luciferase. An integration time of 1 min was used for luminescent image acquisition for all mouse tumor models. Living Image software (Wave Metrics Inc., Lake Oswego, Oreg.) was used to integrate the total bioluminescence signals (in terms of proton counts) obtained from mice. The in vitro detection limit of the IVIS® Imaging System is 1,000 ES-2/Fluc cells.

Ar-339 Sequence Analysis

Ar-339 virus was amplified in chicken embryo fibroblasts and cloned into sequencing plasmids as six separate overlapping fragments (FIG. 1). CDNA-3B and CDNA-4 overlap the 312 bp fragment (nt 7334-7646) that contains the viral subgenomic promoter. In order to avoid mutations due to RT or PCR reactions, for each plasmid three different RT reactions were performed and each one served as template for one PCR reaction. The three PCR amplified bands of each fragment were cloned separately, sequenced and compared to verify the virus sequence. The Ar-339 sequence obtained was compared to the Sindbis published sequence (Strauss E G, Rice C M and Strauss J H 1984) and to the sequence of Sindbis vectors that we used previously in our laboratory, JT-BB and JT-Rep. (Tseng et al 2004a,b). The results are shown in Table IV (Appendix A). The differences in sequence between the Strauss sequence and JT vectors are described in Table V (Appendix A). Functional changes between JT and AR-339 plasmids are summarized in Table VI (Appendix A).

In the viral replicase, comparing the Strauss map with Ar-339, three point mutations in nsp1 were found: nt 353 a silent mutation; nt 1380 and 1381. Both change amino acid 441 from Cys to Ile in Ar339. In the Sindbis-like virus supergroup, the methyltransferase nsp1 has four conserved motifs I (a.a 31 to 51), II (a.a 87 to 86), III (168 to 220) and IV (243 to 260) (Rozanov et al. 1992). Cys 441 to Ile is not in the carboxyterminal domain required for enzymatic activity (K468 to L512) (Wang et al. 1996). Nsp2 has three mutations compared to the Strauss sequence, one silent at nt 3698 (A to G) and two (nt 2992 and 3579) that change amino acids 438 (Pro to Leu) and 634 (Lys to Glu) respectively. Both amino acids are outside the active helicase and protease domains of nsp2 (Rikkonen et al. 1994). Sindbis virus with Pro at 438, as described in the Strauss sequence, has lethal effects on virus replication (Rice et al. 1987). In nsp4 there was a silent mutation at nt 7337 (T to C).

Regarding the structural proteins, the Ar-339 capsid protein had two mutations compared with the Strauss sequence, one silent at nt 8345 (C to A) and one at nt 7846 that changed Pro 67 to Gln. In the consensus Strauss sequence and JT vectors a Proline occurs at position 67. This residue is conserved in different isolates of virus in Australia, and for MK6962, a New Guinea isolate, a Tyr (T) is present at this site (Sammels et al. 1999). This change is in the 11 to 74 amino acid region that doesn't bind to Sindbis RNA (Geigenmuller-Gnirke et al. 1993) and is not in E2 or capsid proteins interaction domains residues 36-39, 108 to 111, 172, 180 to 183, 201, 231-234, 240 or 254 (Katherine E. Owen and Richard J. Kuhn, 1996; H. Lee and D. T. Brown 1994).

There were also two silent mutations in E1 at nt 10392 (T to C) and 10469 (T to A) and two differences in the Ar-339 with the Strauss map were found at positions Ala 72 to Val in Ar-339 and 237 (Ser to Ala), which are both located in domain II. Residues of this domain are involved in E1-E1 interaction in the virus spike (Zhang W et al. 2002).

Most of the coding changes were found in the envelope protein E2, in which the antigenic sites and the binding receptor domain of the virus have been described. Comparing the Strauss sequence with Ar-339, five amino acid changes were found located in the external leaf-like domain of the E2 protein, which extends from the amino terminus to residue 218 (Zhang W et al. 2002). Changes are in amino acids: 3 (Ile to Thr); 23 (Val to Ala); 70 (Lys to Glu) and also two of mutations, 172 (Arg to Gly) and 181 (Glu to Lys), occur in the putative binding receptor domain (amino acids 170 to 220). No changes were found in the endodomain that interacts with the capsid protein (from 391 to 483) or with the E2-E1 interaction region.

An analysis of the amino acid changes between the JT plasmids and the Ar-339 sequence revealed only one mutation in the replicase, Cys 441 to Ile of nsp1. In the structural proteins there were a total of eight differences, only one in the capsid protein, Pro 67 to Gln; and seven in the E1 and E2 envelope proteins. Three mutations in E1: Ala 72 to Val; Gly 75 to Asp and Ser 237 to Ala. Most of the differences were found in the E2 protein, three in the leaf-Like domain; Ile 3 to Thr; Lys70 to Glu and Glu 181 to Lys and one in the ectodomain, Val 251 to Ala. V251 is important for virus maturation in CEF (Li M L et al. 1999).

Vector Constructions

To construct the Ar-339 vectors, the Sindbis genome was split into two plasmids: the replicon and the helper (FIG. 2). This vector system is designed to electroporate in vitro transcribed viral RNA into the susceptible cell line to produce replicative defective Sindbis virus, called viral vector, that contains, as a genome, the replicase RNA and lacks the structural genes. For in vitro transcription, a bacteriophage promoter is required before the viral sequence.

In order to compare the yield of viral vectors in this system, two pairs of vectors were produced, one pair with replicon and helper under the control of the SP6 promoter (SP6-H and SP6-R), and the other pair under the control of the T7 promoter (T7-H and T7-R).

The replicon contains the viral replicase, with the packaging signal, nt 945 to nt 1075, (Weiss B et al. 1994; Frolova et al 1997); the viral subgenomic promoter, multicloning site 1 (MCS1) to allow for the insertion and expression of the gene of interest, and the 3' end of the virus (nt 11394 to 11703) to allow viral (−) strand RNA synthesis. A second multicloning site (MCS2) allows the linearization of the plasmid for in vitro transcription.

The helper plasmid contains the first 425 nt of the virus, followed by the 3' end of the virus from nt 7334 to nt 11703 which includes the subgenomic promoter, the capsid and the viral envelope proteins (E3, E2, 6K and E1) and the 3' end (nt 11394 to 11703).

Both plasmids share the following viral sequences: the first 425 nt, the 309 nt of the 3' end and the sub genomic promoter.

Both plasmids have several non-viral elements in common, the replication origin (rep pMB1) and the Ampicillin resistance gene from the pUC cloning plasmid; the promoter for in vitro transcription (T7 or SP6) and the MCS2. In the construction process a plasmid containing the pUC sequences, SP6 or T7 promoter, the multicloning sites, and the 3' viral end, which are common to both vectors, was first generated. The specific viral sequences were then cloned into this plasmid (FIG. 3).

SP6 and T7 Promoters

For in vitro transcription systems, the RNA yield using SP6 or T7 RNA polymerase for long RNA transcripts could differ. To study if the promoter would make a difference in the titer of the viral vectors production, BHK-21 cells were electroporated with two sets of in vitro transcribed RNAs: SP6-AH and SP6-ARepLacZ, to generate the SP6-LacZ viral vector, and with T7-AH and T7-ARepLacZ for the T7-LacZ vector. The comparison of both vector's titers in BHK-21 cell, in repeated experiments, gave equivalent titers≈$10^6$ transducing units (TU)/mL. In terms of infective particles production, both promoters work with the same efficiency in this system.

Sequencing of the four plasmids (SP6-AH, SP6-ARep, T7-AH and T7-ARep) revealed a deletion of one T at the 3' end of the virus before the poly A (SV nt 11686). To study the effect of this deletion on viral vectors, four new plasmids without the deletion were constructed (SP6-H, SP6-R, T7-H and T7-R) and titers of viral vectors from both sets of plasmids were compared. No significant difference was observed indicating that the deletion of T11686 is not critical for vector replication. As these four sets of vectors showed the same in vitro titer, in order to standardize results the experiments with mice were performed using SP6-H and SP6-R plasmids to synthesize viral vectors.

Example 3

Biological Properties

Cell Tropism

Most of the amino acid differences found between JT and Ar-339 vectors were in the envelope proteins. One of them was related to virus adaptation to BHK-21, E2 Lys 70 to Glu (McNight K et al, 1996) and two of them were located in the receptor-binding domain of the E2 protein. To analyze if the amino acid changes had any effect on the viral vector's infectivity, JT, Ar-339 and chimeric viral vectors were produced and titered in three cell lines: BHK-21 (baby hamster kidney), ES-2 and Mosec human and mouse ovarian cancer cell lines respectively. The results are shown in Table VII (Appendix A). Vectors that carry JT-BB helper (JT-BB/SP6-ARepLacZ and JT-BB/JT-RepLacZ) had titers two logarithms higher in BHK-21 than in the other two cell lines; when the helper was SP6-H, the difference observed was only one log. The infectivity of the vectors in vitro was similar in both ovarian cancer cell lines, ES-2 and Mosec. This difference was observed in repeated experiments.

Disease Progression

In order to compare the ability in targeting and suppression of disease progression by Sindbis vectors Ar-339 and JT, JT and Ar-339 chimeric vectors were produced and tested in the ES-2/Fluc mouse metastatic ovarian cancer model described previously (Tseng et al. 2004b). Five female SCID mice per vector group were injected i.p. with $1.5\times10^6$ ES-2/Fluc cells (day 0) and IVIS® imaged the next day to verify the presence of ES-2/Fluc cells. Cells were left to grow for four days before daily treatment with vectors was started. There were five mouse groups, one of which did not receive vector treatment, whereas the remaining 4 had vectors: A(JT-BB/SP6-RhRluc), B (SP6-H/JT-RephRluc), C (SP6-H/SP6-RhRluc) and D (JT-BB/JT-RephRluc). As these strains showed different cell tropism in BHK-21 cells, vectors were titered in the same cell line used to induce the tumor ES-2/Fluc, and titers for all vectors were standardized at $10^6$ TU/mL. Total whole body photon counts were determined by IVIS® imaging on days 1, 5, 13, and 19 to determine disease progression of ES-2/Fluc metastases (FIG. 4). Survival curves were also compared (FIG. 5).

Vector A, carrying the Ar-339 replicase (SP6-RhRluc) and JT structural proteins was more efficient in reducing tumor progression and gave better survival of the animals. The vectors carrying the same structural proteins, vector B versus C and A versus D were compared. In both cases there was more tumor reduction with Ar-339 replicase (SP6-RhRluc). Regarding the structural part, when the vectors carrying the same replicase were analyzed, in one case SP6-H seemed to be more effective (Vectors D versus B), but in the case of A versus C, where the photon count difference is larger, JT-BB is more efficient in tumor targeting. The small differences between vectors B, C and D correlates with similar animal survival data, although both structural proteins and replicase function in the efficiency of the vectors in vivo, these data suggest that an improvement in the targeting of Ar-339 replicase (SP6-R) to tumor cells would lead to more efficient gene therapy vectors.

Co-Localization

Figure 6A:
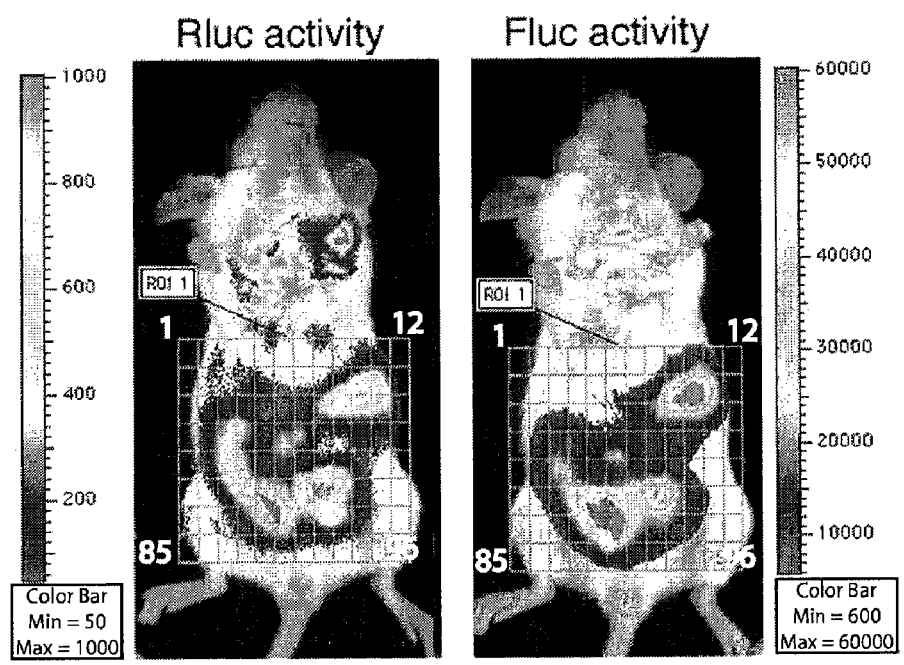
Figure 6B:
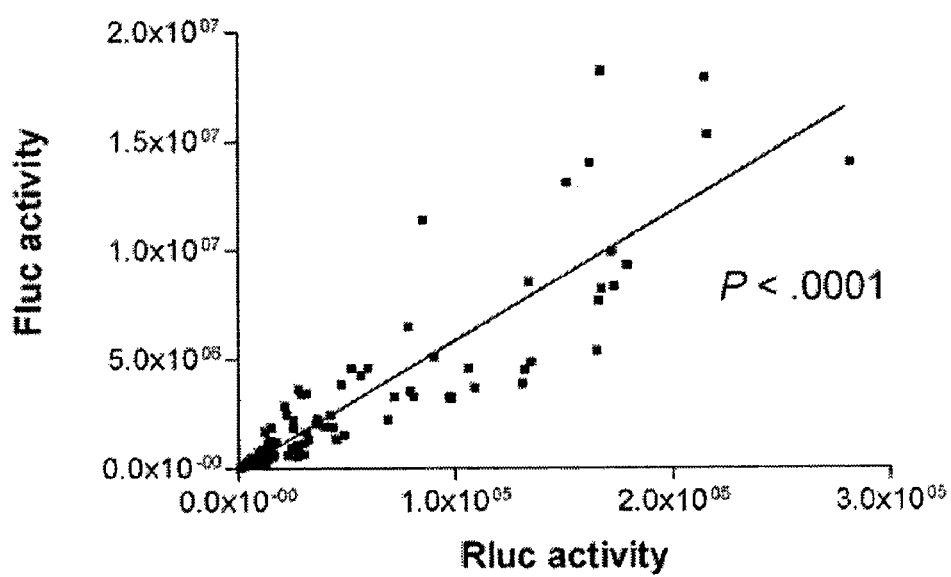

To establish the degree and specificity of Ar-339 Sindbis infection of tumor cells, IVIS® imaging studies were performed that measured independent bioluminescent signals from tumor cells and vectors. The ES-2/Fluc cells expressed the firefly luciferase gene, that uses D-luciferin as substrate, and the vectors carried a different luciferase gene cloned from soft coral *Renilla renifomis* (Rluc) that uses coelenterazine to generate bioluminescence. The two luciferases are highly substrate specific and do not cross-react (Bhaumik S and Gambhir S S. 2002). Each anesthetized mouse was first treated with coelenterazine the image was collected (FIG. 6A, left panel), then treated with D-luciferin for a second IVIS® imaging, this time of ES-2/Fluc cells (FIG. 6A right panel). The bioluminescence signals generated in the same animal from Sindbis/Rluc and ES-2/Fluc, were quantitated using Living Image software. The images of Rluc and Fluc signals were grided (128, 96 boxed regions), and corresponding regions were analyzed for statistical correlation (FIG. 6B). A highly significant correlation was established ($P<0.0001$) indicating that a single i.p. delivery of Ar-339 Sindbis vector lead to the efficient infection of the metastasized tumor cells throughout the peritoneal cavity. In several mice an additional infection outside the peritoneal cavity was observed.

Ar-339 Targeting

Figure 7A:
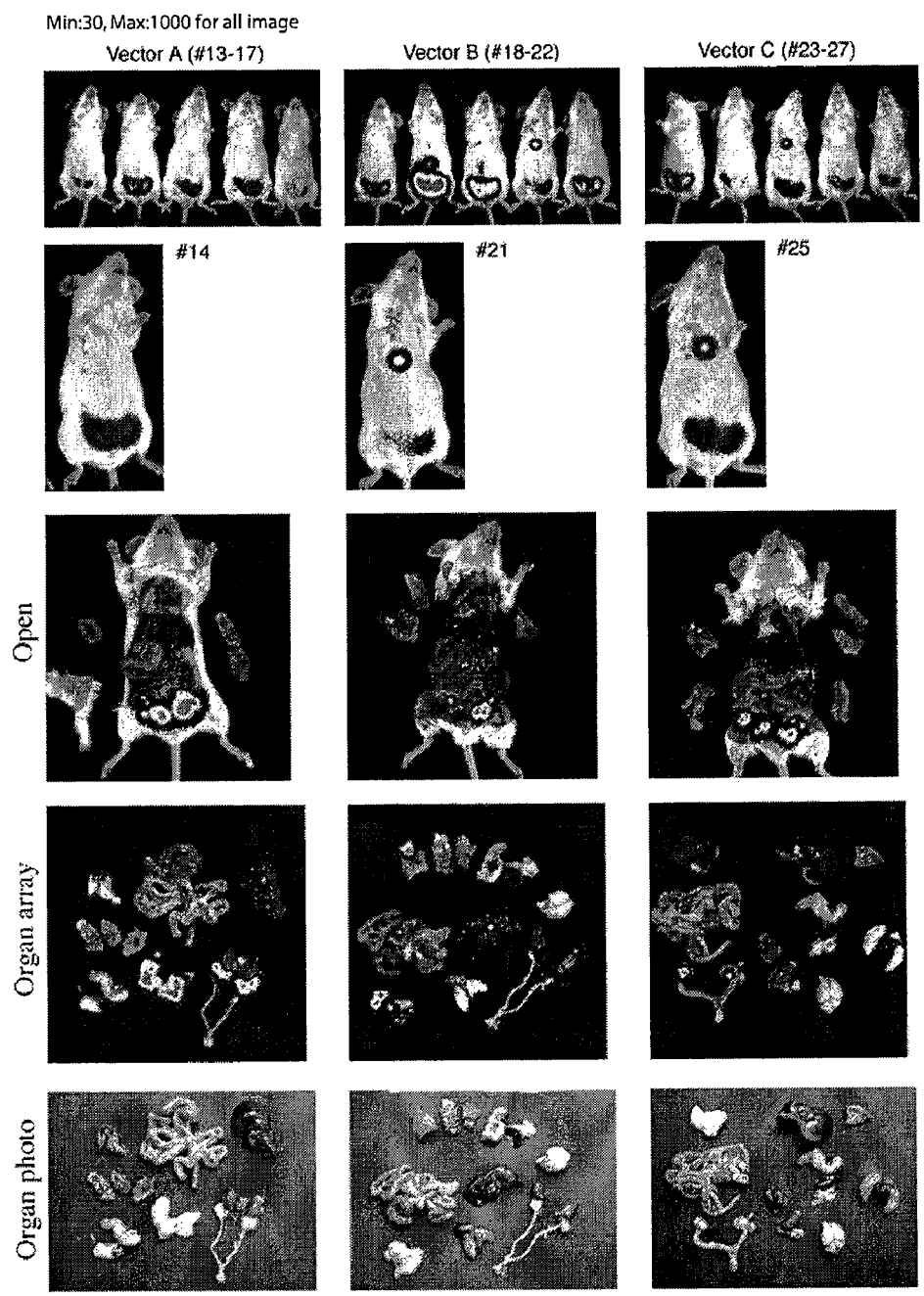
Figure 7B:
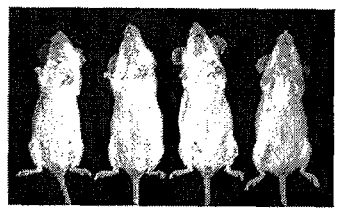
Figure 7B:
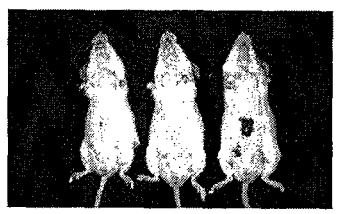
Figure 7B:
Figure 7B:
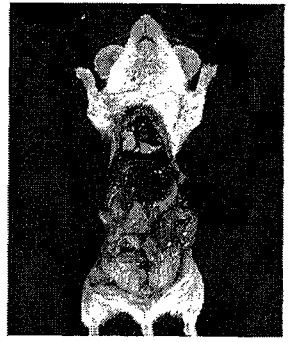
Figure 7B:
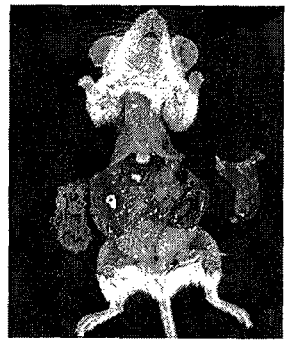
Figure 7B:
Figure 7B:
Figure 7B:
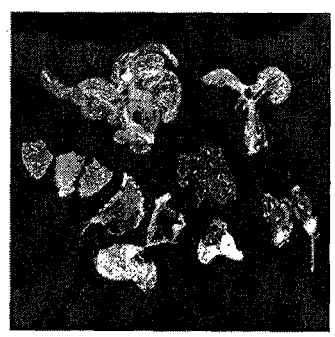
Figure 7B:
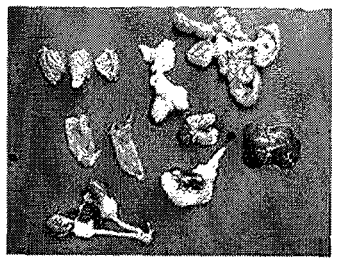
Figure 7B:
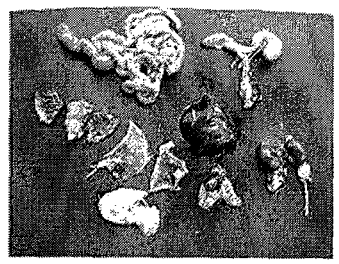

To analyze tissues or organs targeted by the Ar-339 strain, new chimeric vectors were made with firefly luciferase (Fluc) as the reporter gene, since its stronger bioluminescent signal allows the study of vectors in animal organs. Each vector was tested in two groups of 5 SCID female mice: tumor-free and 5 day ES-2 metastasis induced mice. To assess which part of the C vector was responsible for the chest bioluminiscence, three Fluc chimeric vectors were made: A(JT-BB/SP6-RFluc), B(SP6-H/JT-RepFluc) and C (JT-BB/JT-RepFluc). As previously, vectors were titered in ES-2 cells. Tumor free mice received one dose of vector ($10^4$ TU/mL) at day 0 and were IVIS® imaged next day (FIG. 7A). All three groups showed a low background signal in fat tissue. Two out of five vector B mice and one of five mice in vector C group showed some additional bioluminescent signal in the chest, as previously observed in the colocalization experiment. To investigate if vectors were infecting organs in these mice, intraperitoneal cavity and harvested organs were also IVIS® imaged. The chest signal observed corresponded to connective tissue in the ribs, while organs had no background signal. To study if repeated doses of these vectors could lead to accumulative infection in tumor-free mice, a second dose was i.p. injected on day 2 and the image repeated on day 3. The results (FIG. 7B) showed low background signal in fat tissue for vectors B and C and no signal at all for vector A, indicating that the background is transient and shouldn't affect the target effectiveness of Ar-339 vectors in repeated treatment.

Figure 8A:
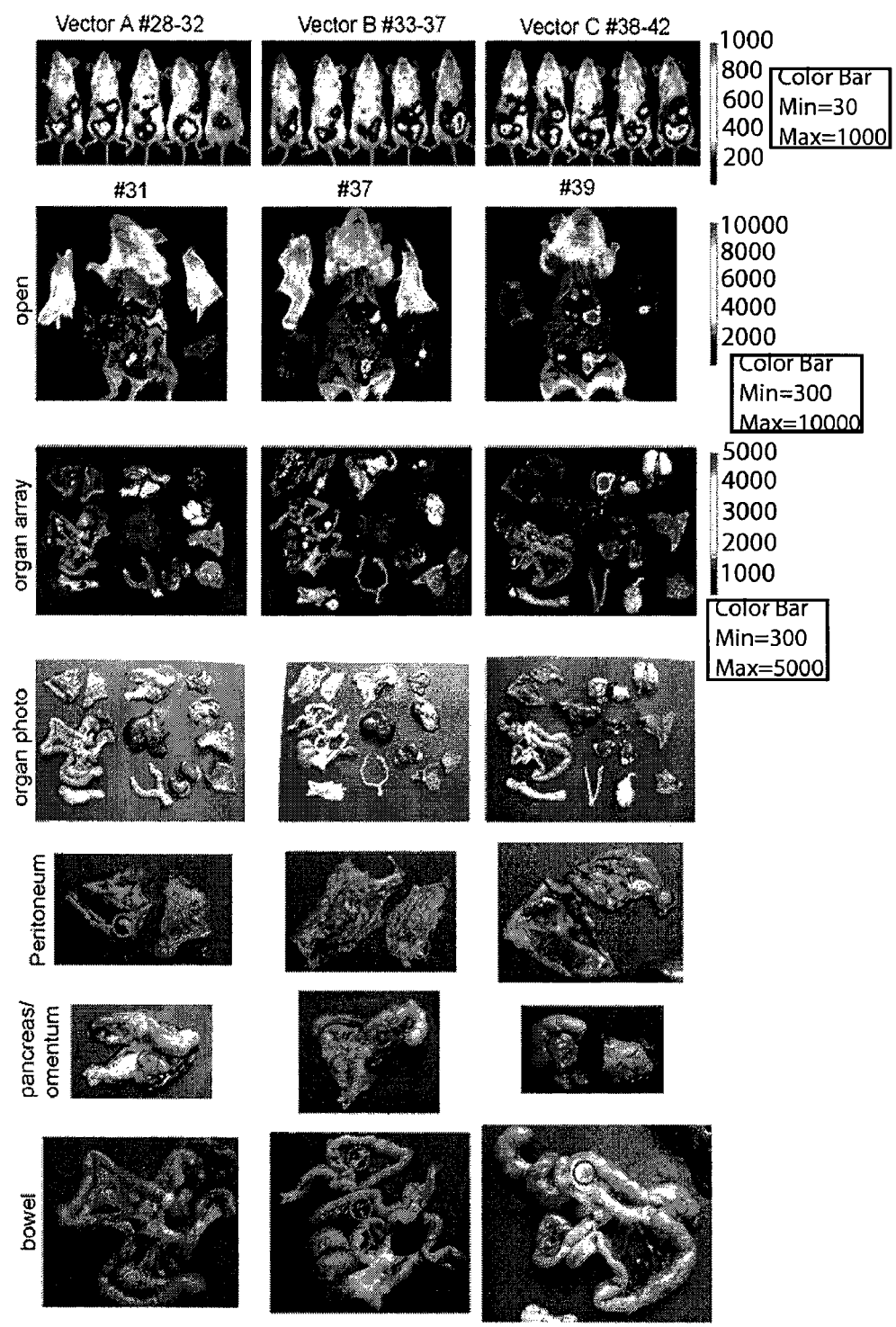
Figure 8B:
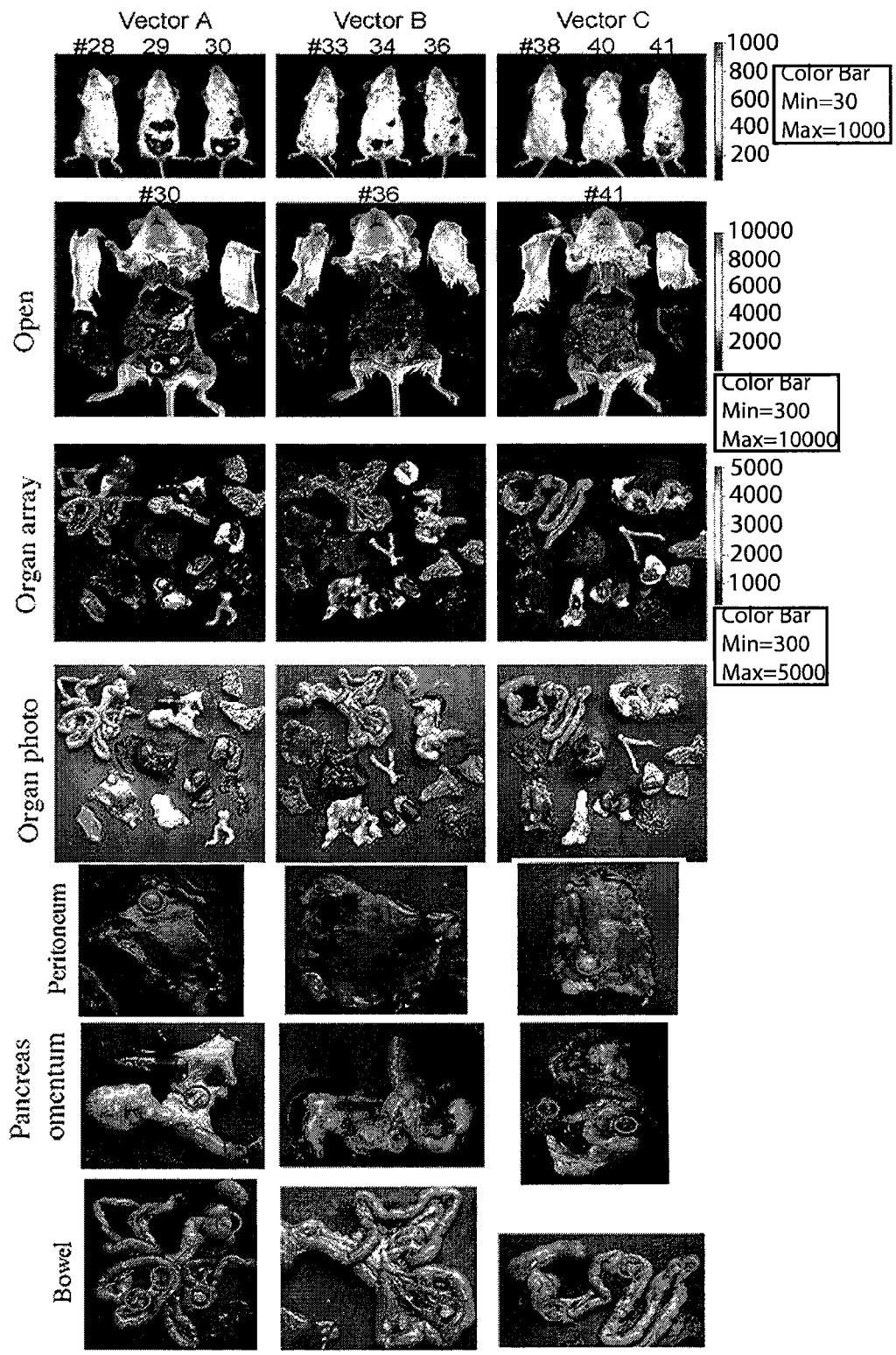
Figure 9A:
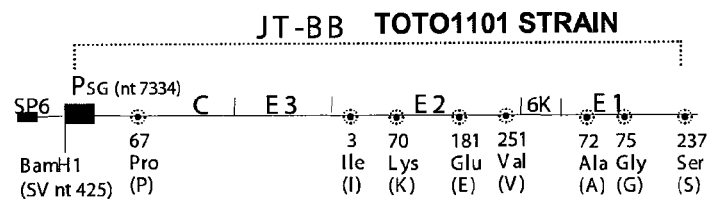
Figure 9B:
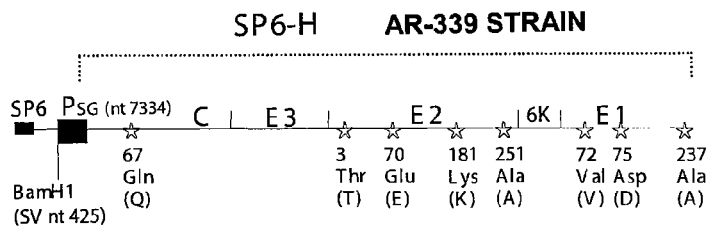
Figure 9C:
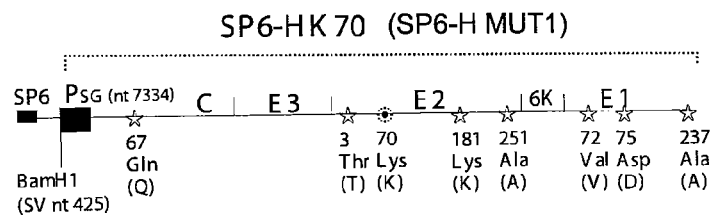
Figure 9D:
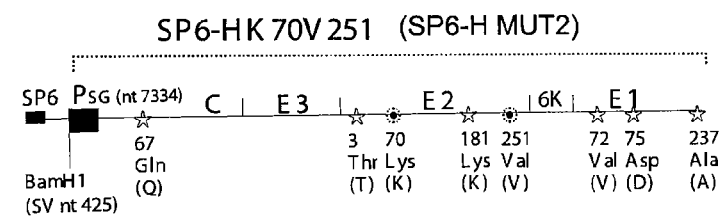
Figure 9E:
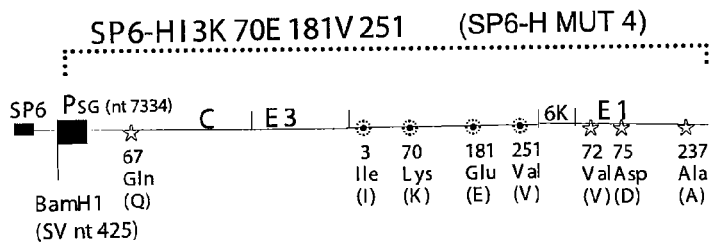

Previous studies of JT/Fluc vector in 5 day ES-2 tumor induced mice, showed that the vector specifically targets metastasized ES-2 cells after one injection and also in a second dose two days later (Tseng et al. 2004). To study if the difference between sequences could affect the specificity of Ar-339 vector, these 3 chimeric vectors were tested in the same model. Mice injected with $2\times10^6$ ES-2 cells on day 0, received one i.p. dose of vectors on day 5 and were IVIS® imaged on day 6. The peritoneal cavity and organs of two mice per group were imaged. As is shown in FIG. 8A for all vectors, bioluminescence correlated with ES-2 metastatic implants. At day 7 two mice per group received a second i.p. dose of vector and one mouse was not injected to serve as a luciferase background signal control (FIG. 8B). Vector A showed a similar signal compared with previous doses, but vectors carrying Ar-339 structural proteins, B and C, showed decreased bioluminescence signals in tumors compared with the first injection. The difference in reinfection suggests that amino acid changes in structural proteins could play an important role in targeting metastases by repetitive treatment with vector.

In order to determine which mutations were critical for the vector properties, a chimeric vector was generated, QE2, that contains E2 from JT-BB and the remaining structural proteins from Ar-339. When we compared with Ar-339 vector in the same IVIS® animal model as in the previous experiment, in tumor free animals, a low background in fat tissue with the first dose was observed and no signal in a second dose. In ES-2 5 day induced tumor mice, vector QE2 targeted tumor and was able to re-infect animals, though the bioluminescent signal was not as strong as for Ar-339 vector (data not shown). This indicates that Ar-339 sequence in the E2 envelope protein was primarily responsible for the targeting pattern, though the optimal amino acid pattern was still not clear. To address this question site directed mutagenesis was performed on the Ar-339 E2 envelope protein.

E2 Mutants

The E2 envelope has been described as the protein that is primarily responsible for cell tropism and infectivity of Sindbis virus. More specifically, Lys 70 is implicated in BHK-21 specificity (McNight K et al, 1996) and also residues 69 to 72 have been related to targeting vertebrate cells (Ohno K et al. 1997; Dubuisson J and Rice C M, 1993). As the Ar-339 strain has a Glu in this position, 3 point mutants were generated that contain Lys at position 70 (FIG. 9). In Mut-1 only Ar-339 Glu 70 was changed to Lys. Amino acid 251 of E2 is highly conserved between different Sindbis isolates (Sammels L M et al. 1999) and mutation to Valine at this position has been related with host range phenotype (Li M L et al. 1999). To explore the influence of this amino acid in vector targeting, Mut-2 was produced that has Lys70 and also Ar-339 Ala 251 mutated to Val. Residues at positions 3 and 181 are located in the external leaf-like domain of the E2 protein and 181 is in the receptor binding domain. To assess if the combination of these 4 amino acid changes in the E2 is responsible for the difference in infection of Ar-339 vectors, mutant Mut-4 was produced with Lys 70, and Val 251 plus changes in Ar-339 Thr 3 to Ile and Ar-339 Lys 181 to Glu (FIG. 9). The mutants were tested in tumor-free and ES-2 5 day induced tumor mice as previously described for vectors A, B and C. To assure that the difference in signals were due to the E2 mutations, all five vectors tested carried the same replicase SP6-RFluc: vector A (JT-BB/SP6-RFluc), C (SP6-H/SP6-RFluc), Mut-1 (SP6-H-K70/SP6-RFluc) Mut-2 (SP6-H-K70-V251/SP6-RFluc) and Mut-4 (SP6-H-I3-K70-E181-V251/SP6-RFluc).

Vectors were titered in BHK-21 cells and in ovarian cell lines ES-2 and Mosec (Table VIII (Appendix A)). Mutants showed a greater difference between A and C when titered in BHK-21 than in ovarian cell lines.

In tumor-free mice vectors A and C gave background in some of the animals. Only one out of the five vector C mice showed a low bioluminescent signal in the ribs (FIG. 10A). In second doses of these vectors the background was even less noticeable (FIG. 10B). Mut-1 and Mut-2 did not produce background bioluminescent signal in either dose. Mut-4 showed barely detectable signal in fat tissue, much less intense than vectors A and C.

In ES-2 tumor induced mice (FIG. 11A) mice #79 in A and #88 in C vector groups did not show bioluminescence; these mice did not develop ES-2 metastatic implants in the peritoneal cavity (these mice are not shown in the Figure).

This result showed a dramatic decrease in the infectivity of mutants Mut-1 and Mut-2 and an important reduction in Mut-4 after the first and second dose (FIG. 11). The change of only one amino acid in Ar-339 E2 at position 70 makes vector C lose the specificity in targeting ES-2 tumor metastases in vivo. The double mutant with Valine at position 251, Mut-2, doesn't revert the vector tropism. Mut-4 combines vector A E2 with Ar-339 E1, E3 and capsid sequences. The fact that Mut-4 could not revert to full infectivity indicates that the interaction between E2 and E1 in the vector spike could also play an important role in vector targeting.

Example 4

Suppression of Disease Progression by Ar-339, MUT-4 and JT Vectors

In previous mouse experiments Vector C showed background infections in some of the animals treated. Although this effect was transient and vector C was efficient in suppression of disease progression, it would be preferable for gene therapy to use a viral vector that does not cause background tissue infections. In tumor targeting experiments of SP6-HE2 mutants, vector Mut-4 showed tumor targeting although with less intensity than vector C (FIG. 11) and did not show background infection (compare FIGS. 10A and 10B). With the aim of improving this vector system, the ability of Mut-4 in tumor reduction was studied and vector-tumor colocalization analyzed, using the same model described for vectors A, B, C and D as in previous experiments.

Materials and Methods

Animal models. All animal experiments were done in accordance with NIH and institutional guidelines. To determine the therapeutic effects of Sindbis virus vectors, SCID mice (female, 6-8 week old; Taconic, Germantown, N.Y.) were i.p. injected with $1.5\times10^6$ ES-2/Fluc cells/mouse on day 0 and imaged with the IVIS® system the next day (day 1) to confirm the presence of tumor cells. Then on day 4, 10 mice/vector received i.p. treatment with vectors carrying the *Renilla* luciferase: Mut-4 (SP6-HI3K70E181V251/SP6-RHRluc), C (SP6-H/SP6-RhRluc) and D (JT-BB/JT-RephRluc). All vectors had the same titer in ES-2/Fluc cells, and mice were i.p. injected daily with $\sim10^6$ TU in 0.5 ml Opti-MEM I/mouse. Control mice (n=5) received no Sindbis vector treatment. Disease progression was later determined by IVIS® imaging on days 1, 5, 9 and 13.

Survival curves were compared with log rank test. All the P values presented in this study are two-tailed.

For colocalization experiments, two SCID mice/vector were i.p. inoculated with $1.5\times10^6$ ES-2/Fluc cells on day 0 and received one i.p. treatment of vector Mut-4 ($\sim10^6$ TU in 0.5 mL of OptiMEM I) on day 5. The next day (day 6), mice were i.p. injected with 0.3 mL of 0.2 mg/mL coelenterazine (Biotium, Inc., Hayward, Calif.) followed by IVIS® imaging for *Renilla* luciferase activity. 30 minutes later, the same mice were i.p. injected with 0.3 mL of 15 mg/mL D-luciferin (Biotium, Inc) and a second IVIS® imaging for Firefly luciferase activity was performed.

Results

Colocalization. To measure the degree and specificity of Mut-4 Sindbis infection of tumor cells, IVIS® imaging studies were performed that measured independent bioluminescent signals from tumor cells and vector Mut-4 (SP6-HI3K70E181V251/SP6-RhRluc). The ES-2/Fluc cells expressed the Firefly luciferase gene, that uses D-luciferin as a substrate, and the vector carried a different luciferase gene cloned from soft coral *Renilla reniformis* (hRluc) that uses coelenterazine to generate bioluminescence. The two luciferases are highly substrate specific and do not cross-react (Bhaumik, S. and Gambhir, S. S. 2002). Each anesthetized mouse was first treated with coelenterazine and the image was collected (FIG. 12A, left panel), then treated with D-luciferin for sequential IVIS® imaging of ES-2/Fluc cells (FIG. 12A, right panel). The bioluminescence signals generated in the same animal from vector and ES-2/Fluc were quantitated using Living Image software. The images of Rluc and Fluc signals were grided (12×8, 96 boxed regions), and the corresponding regions were analyzed for statistical correlation (FIG. 12B). A highly significant correlation was established ($P<0.0001$) indicating that a single i.p. delivery of Mut-4 Sindbis vector leads to very efficient infection of the metastasized tumor cells throughout the peritoneal cavity.

Disease progression. In order to compare the ability of Sindbis vectors Ar-339 and Mut-4 in targeting and suppression of disease, vectors were constructed and tested in the ES-2/Fluc mouse metastatic ovarian cancer model described previously. Ten female SCID mice per vector group were injected i.p. with 1.5×10$^6$ ES-2/Fluc cells (day 0) and IVIS® imaged the next day to verify the presence of ES-2/Fluc cells in the mice. Cells were left to grow for four days before daily treatment with vectors was started. There were four groups of animals, one of which did not receive vector treatment, the remaining 4 were injected daily with 10$^6$ TU/ml doses of vectors carrying *Renilla luciferase* reporter gene: C (SP6-H/SP6-RhRluc), Mut-4 (SP6-HI3K70E181V251/SP6-RhRluc). and D (JT-BB/JT-RephRluc).

Total whole body photon counts were determined by IVIS® imaging on days 1, 5, 13, and 19 to determine disease progression of ES-2/Fluc metastases. Survival curves were also compared (FIG. 13). Mice treated with vectors C and Mut-4 showed similar photo count reduction and survival proportions. These data suggest that vector Mut-4 (SP6-HI3K70E181V251/SP6-RHRluc) has similar in vivo efficiency in tumor reduction as vector C (SP6-H/SP6-RhRluc) and so can also be used in gene therapy. Both vectors, C and Mut-4, showed significantly improved tumor reduction and mouse survival compared to vector D.

Example 5

Background

The titer in BHK cells of defective Sindbis virus vectors C (SP6-H/SP6Rfluc), Mut-1 (SP6H-K70/SP6RFluc), Mut-2 (SP6H-K70-V251/SP6RFluc), and Mut-4 (SP6H-I3-K70-E181-V251/SP6RFluc) were lower than the titer of the vector carrying the JT-BB helper (Table A). The titer of the Mut-4 vector in BHK cells was ten times lower than the JT vector. Since all of the vectors carried the same replicon plasmid, the difference in titer should be due to the sequence of the Helper plasmid. In order to improve the production of the viral vectors, amino acid residues 72, 75 and 237 of the E1 protein in the Helper plasmid SP6H-I3-K70-E181-V251 were changed to Val, Asp and Ala respectively. These are the corresponding amino acids in the JT-BB Helper plasmid. The capsid residues were not modified. A summary of the differences in amino acid residues between these helpers is shown in Table D.

It has been disclosed that Helper RNAs with the tRNAAsp at the 5' terminus are replicated to higher levels than RNAs with a 5' terminus identical to that of Sindbis virus genomic RNA (U.S. Pat. No. 5,091,300). They also produced higher levels of PFU, indicating that they were packaged to higher levels than were Helper RNAs which had the Sindbis virus genomic 5' terminus (20, 21). Because of this data, nt 11 to nt 73 of the AsptRNA sequence were cloned into the 5 end of the Helper vector.

DM-Helper Cloning.

The DM-Helper plasmid, was constructed from the SP6H-I3-K70-E181-V251 plasmid (SEQ ID NO:39)) following 3 main steps: first, the AvrII restriction size was introduced in the 5' end; second, E1 amino acid residues 72, 75 and 231 were mutagenized; third, the tRNA sequence in the AvrII site was added at the 5' end. The sequence of primers used and nucleotide changes are shown in Table B.

1.—AvrII mutagenesis. The introduction of the AvrII site was performed using the QuickChange IIx site-directed mutagenesis kit (Stratagene, La Jolla, Calif.) using the manufacturer's instructions. Briefly, 10 ng of SP6H-I3-K70-E181-V251 plasmid (SEQ ID NO:39) were incubated with its complementary primers: AvrII-F and AvrII-R, reaction buffer, dNTPs and 2.5 units of pfuUltra HF DNA polymerase. PCR reactions were 95° C. 1 min, 18 cycles of: 95° C. 50 s, 60° C. 50 s, 68° C. 7 min, and final elongation of 68° C. 7 min. After the PCR reactions 10 U of restriction enzyme DpnI was added and the reaction was incubated at 37° C. for 1 hour to digest methylated parental DNA. XL-10-Gold competent *E. coli* cells were transformed and the colonies analyzed by restriction enzyme digestion (RE). Mutations were verified by sequencing. The plasmid produced was named #810.

2.—E1 mutagenesis. The same QuickChange IIx site-directed mutagenesis kit (Stratagene, La Jolla, Calif.) was used to mutagenize consecutively E1 residues 72, 75 and 251. In the first reaction the complementary primers E1-7172F/E1-7172R were used yielding the plasmid #815. The second reaction was performed using 10 ng of plasmid #815 with primers E1-237F/E1-237R to obtain plasmid #821.

3.—Adding tRNA to 5' end of vector 821, the T-125 plasmid. First the T-125 plasmid containing the tRNA sequence was generated, then tRNA was cloned into plasmid #821. Primer pairs TRNA-F(T-F)/TRNA-R(T-R)[1] (25 uM/each) were boiled for 1 min and cooled down to room temperature for primer annealing. This reaction (150 ng) was used as a template in the PCR reaction with primers T-F and T-R. The PCR conditions were: reaction buffer (1×), dNTP's (200 μM), forward and reverse primers (0.5 μM/each) and 1 unit of Taq-DNA-polymerase in a final volume of 20 μl. The PCR reaction was performed in three secondary tubes with a gradient for annealing temperature: 95° C., 5 min; 35 cycles of [95° C., 30 s; 52.1° C., 30 s (tube 1); or 55.2° C., 30 s (tube 2); or 58.5° C., 30 s (tube 3); 72° C., 30 s] and 72° C. 30 sec. Bands were stronger for the 52.1° C. annealing temperature. The 124 bp bands were then isolated and ligated to the pCR®2.1-TOPO vector (Invitrogen, San Diego Calif.; cat#K45-0040) *E. coli* Tam1 competent cells were transformed with the ligation and positively selected colonies screened by double digestion with AvrII and MfeI. The positive plasmid was named T-125 and was checked by sequencing.

[1]TRNA-F and TRNA-R are commercially available complementary oligonucleotides (Gene Link, Hawthorne, N.Y.). TRNA-F contains from the 5' end the Avr Restriction Endonuclease (RE) site for cloning, the SP6 promoter, the tRNA sequence, the 5' end of the Sindbis virus (SV) sequence (from nt29 to nt46) and the Mfe I RE site at the 5' end.

Plasmid T-125 was digested with AvrII and MfeI, the 109 bp band was isolated in an agarose gel, and ligated to the AvrII/MfeI band of the 821 plasmid. Screening of positive colonies was performed by digesting the plasmids with restriction enzymes AvrII/MfeI and the positive plasmid DM-helper#9 was fully sequenced.

Vector Production and Titering

Cells. BHK-21 were obtained from the American Type Culture Collection (ATCC Manassas, Va.). BHK-21 cells were maintained in αMEM (JRH Bioscience) with 5% FBS. Basal media was supplemented with 100 μg/ml of penicillin-streptomycin and 0.5 μg/ml of amphotericin B (both from Mediatech).

In vitro transcription and vector preparation. The plasmids carrying the Sindbis replicon SP6-R (SEQ ID No. 36) or DM-Helper helper RNAs were linearized with XhoI, before in vitro transcription using the mMESSAGE mMACHINE RNA transcription kit (SP6 version; Ambion). Both helper and replicon RNA transcripts (20 μl each) were then electroporated into BHK-21 cells and incubated in 10 ml of αMEM containing 5% FBS at 37° C. for 12 h. The medium was replaced with 9 ml of Opti-MEM I medium (GIBCO-BRL, Invitrogen San Diego Calif.) supplemented with 0.7 μM CaCl$_2$. After 24 h, the culture medium was collected and stored at −80° C.

DM-Helper Vector titering. The titers of Sindbis vectors were assayed in BHK-21 cells. Serial dilutions (50 μL each) of vector were added to 10$^4$ BHK-21 cells in 96-well plates. After incubation for 1 hour at room temperature, the cells were washed with PBS and incubated with 200 μL of αMEM at 37° C. overnight (≈12 hours).

The next day total of RNA from each well was extracted separately using the Trizol extraction protocol (Invitrogen cat# 15596-018). One μg of each RNA was used as template to make cDNA with primer cDNA5-R (5'-TTTTTGAAAT-GTTAAAAACAAAATTTTGTTG (SEQ ID NO: 18)) and ThermoScript™ RNaseH-reverse transcriptase (Invitrogen cat# 12236-022), at 60° C. for 2 h, following the manufacture $R^1$ S protocol.

The presence of Sindbis cDNA in each dilution was detected by real time PCR using the MyiQ Single-Color Real-Time PCR Detection System (BioRad, Cat#170-9740)

The PCR reactions were performed for each vector cDNA dilution. One hundred ng of the cDNA reaction were used as template for each PCR reaction, with 250 nM primers cDNA5-R (5'-TTTTTGAAATGTTAAAAA-CAAAATTTTGTTG (SEQ NO: 18)) and 7692F (5'-TGATC-CGACCAGCAAAACTC (SEQ ID NO: 42)), using SGMIX (2×) (Biorad, Cat# 170-882).

For generating the standard curve 10× serial dilutions of the XhoI linearized SP6RLacZ plasmid were used, three reactions per dilution, ranging from $10^3$ pg to $10^{-3}$ pg.

All reactions were performed in 96 well plates with thermic conditions: 95.0° C. 5 min, 40 cycles of: 95° C. 20 sec, 60.0° C. 30 sec and 72.0° C. 30 sec. Fluorescence data were acquired at 72.0° C. in each cycle. Melting curves started at 55.0° C. 10 see, increasing set-point temperature after cycle 2 by 0.5° C.

The presence of the 301 amplified band was checked by electrphoresis in agarose gels. The results of the titration are set forth in Table C.

Tables for Example 5

TABLE A

Titer of Sindbis vectors in BHK cells

| | VECTOR | Titer in BHK |
|---|---|---|
| A | (JTBB/SP6RFluc) | $10^7$ |
| C | (SP6-H/SP6Rfluc) | $10^5$ |
| Mut-1 | (SP6H-K70/SP6RFluc) | $10^4$ |
| Mut-2 | (SP6H-K70-V251/SP6RFluc) | $10^5$ |
| Mut-4 | (SP6H-I3-K70-E181-V251/SP6RFluc) | $10^6$ |
| DM-Helper | (DM-Helper/SP6R) | $10^9$ |

TABLE B

Primers to construct DM-Helper#9

| Primer | Sequence (5'→3') | RE |
|---|---|---|
| TRNA-F | GTGGGAG*CCTAGG*GTACATTTAGGTGACACTATA GGATATAGTGGTGAGTATCCCCGCCTGTCATGCG GGAGACCGGGGTTCGGTTCCCCGACGGGGAGCCA AACAGCCGAC*CAATTG*CACTAC (SEQ ID NO: 43) | AvrII MfeI |
| TRNA-R | GTAGTG*CAATTG*GTCGGCTGTTTGGCTCCCCGTC GGGGAACCGAACCCCGGTCTCCCGCATGACAGGC GGGGATACTCACCACTATATCCTATAGTGTCACC TAAATGTAC*CCTAGG*CTCCCAC (SEQ ID NO: 44) | MfeI AvrII |
| T-F | GTGGGAC*CCTAGG*GTAC (SEQ ID NO: 45) | AvrII |

TABLE B-continued

Primers to construct DM-Helper#9

| Primer | Sequence (5'→3') | RE |
|---|---|---|
| T-R | GTAGTG*CAATTG*GTCGG (SEQ ID NO: 46) | MfeI |
| AvrII-F | GCTCACATGTGGGAG*CCTAGG*GTACATTTAGGTG AC (SEQ ID NO: 47) | AvrII |
| AvrII-R | GTCACCTAAATGTAC*CCTAGG*CTCCCACATGTGA GC (SEQ ID NO: 48) | AvrII |
| E1-7275F | GTCAGCCGGCCG*CGCATGCA*G*GTATACC*TGCAAG (SEQ ID NO: 49) | SphI BstZ17I |
| E1-7275R | CTTGCA*GGTATAC*CCT*GCATGC*GCGGCCG GCTGAC (SEQ ID NO: 50) | BstZ17I SphI |
| E1-237F | CCGTACACGCAGGC*CTCTTC*AGGATTTGAGATGT GG (SEQ ID NO: 51) | EarI |
| E1-237R | CCACATCTCAAATCCT*GAAGAG*GCCTGCGTGTAC GG (SEQ ID NO: 52) | EarI |

TABLE C

Titer of DM-Helper vector in BHK cells by Real time PCR

| DILUTION | DM-Empty (pg) | (M) AVERAGE | (−) Back | Band in gel |
|---|---|---|---|---|
| 1.E−06 | 4.70E+03 | 2.40E+03 | 3.55E+03 | 3.55E+03 | + |
| 1.E−07 | 5.56E−02 | 3.09E−02 | 4.33E−02 | 4.09E−02 | + |
| 1.E−08 | | 1.42E−02 | 1.42E−02 | 1.18E−02 | + |
| 1.E−09 | 7.83E−02 | 6.55E−02 | 7.19E−02 | 6.95E−02 | + |
| 1E−10 | 4.57E−03 | 2.34E−03 | 3.46E−03 | 1.09E−03 | − |
| 1E−11 | 1.01E−02 | 5.82E−03 | 7.96E−03 | 5.59E−03 | − |
| 1E−12 | 1.68E−03 | 5.36E−03 | 3.52E−03 | 1.15E−03 | − |
| Water | | 1.32E−03 | 1.32E−03 | −1.05E−03 | − |
| BHK-55 | | 2.37E−03 | 2.37E−03 | 0.00E+00 | − |

TABLE D residue comparison of helper mutants

| nt | Protein (a.a.) | JT-BB | Mut-4 | DM-Helper |
|---|---|---|---|---|
| 7846 | Capsid (67) | Pro | Gln | Gln |
| 8638 | E2 (3) | Ile | Ile | Ile |
| 8838 | E2 (70) | Lys | Lys | Lys |
| 9171 | E2 (181) | Glu | Glu | Glu |
| 9382 | E2 (251) | Val | Val | Val |
| 10279 | E1 (72) | Ala | Val | Ala |
| 10288 | E1 (75) | Gly | Asp | Gly |
| 10773 | E1 (237) | Ser | Ala | Ser |

TABLE E

Comparison of 5[1] terminus of Helper plasmids in U.S. Pat. No. 5,091,309 and DM

```
'309 patent   1GGATATAGTGGTGAGTATCCCCGCCTGTCACGCGGGAGACCGGGGTTCGGTTCCCCGACG   60
DM-Helper     1..............................T.............................   60

'309 patent  61GGGAGCCAAACAGCCGACCAATTGCACTACCATCACAATGGAGAAGCCAGTAGTAAACGT  120
DM-Helper    61............................................................  120

'309 patent 121AGACGTAGACCCCCAGAGTCCGTTTGTCGTGCAACTGCAAAAA-GCTTCCCGCAATTTGA  179
DM-Helper   121...........................................A................  180

'309 patent 180GGTAGTAGCACAGCAGGTCACTCCAAATGACCATGCTAATGCCAGAGCATTTTCGCATCT  239
DM-Helper   181............................................................  240

'309-patent 240GGCCAGTAAACTAATCGAGCTGGAGGTTCCTACCACAGCGACGATCTTGGACATAGGCAG  299
DM-Helper   241............................................................  300

'309 patent 300CGCACCGGCTCGTAGCATGTTTTCCGAGCACCAGTATCATTGTGTCTGCCCCATGCGTAG  359
DM-Helper   301...............A............................................  360

'309 patent 360TCCAGAAGACCCGGACCGCATGATGAAATATGCCAGTAAACTGGCGGAAAAAGCGTGCAA  419
DM-Helper   361............................................................  420

'309 patent 420GATTACAAACAAGAACTTGCATGAGAAGATTAAGGATCTCCGGA (SEQ ID NO: 53)  463
DM-Helper   421............................................ (SEQ ID NO: 54)  464

Score = 152 bits (79), Expect = 3e-33
Identities = 79/79 (100%), Gaps = 0/79 (0%)
Strand = Plus/Plus '309 Patent 526AAATATGCCAGTAAACTGGCGGAAAAAGCGTGCAAGATTACAAACAAGAACTTGCATGAG  585
DM-Helper   386............................................................  445

'309 Patent 586AAGATTAGGATCTCCGGA (SEQ ID NO: 55)                            604
DM-Helper   446.................. (SEQ ID NO: 55)                            464

CPU time:       0.04 user secs.      0.02 sys. Secs      0.06 total secs.
```

TABLE F

DM-Helper components

| Nt → nt | Part from: | Description |
|---|---|---|
| 1_66 | Oligos | Nt 9 to nt 70 of Asp-tRNA sequence |
| 67_464 | SV nt 29_426 | |
| 67_97 | SV nt 29_59 | 5' end untranscribed |
| 98_464 | SV nt 60_426 | Nsp1 5' end nt 1 to 367 |
| 461_4831 | SV 7333_11703 | SGP + Helper proteins |
| 461_726 | SV 7333_7598 | Nt 1583 to nt 1848 of nsp4 sequence = 3' end. Works as SGP enhancer |
| 727_774 | SV 7599_7646 | Subgenomic promoter (SGP), core sequence |
| 775_1566 | SV 7647_8438 | Capsid protein sequence |
| 1567_1758 | SV 8439_8630 | E3 envelope protein sequence |
| 1759_3027 | SV 8631_9899 | E2 envelope protein sequence |
| 3028_3192 | SV 9900_10064 | 6K peptide sequence |
| 3193_4509 | SV 10065_11381 | E1 envelope protein sequence |
| 4510_4830 | SV 11382_11703 | 3' end untranslated region |
| 4831_4869 | SV Poly A tail | |
| 4870_4897 | Oligos | Multi cloning site MCS |
| 4898_6728 | Bacterial part pUC | |
| 5034_5894 | Bacterial part pUC | Beta Lactamase (=Amp resistant gene) |
| 6039_6668 | Bacterial part pUC | Bacterial DNA replication origin ColE1 |
| 6729_6746 | Oligos | SP6 promoter |

A restriction endonuclease map of the DM-Helper plasmid is shown in FIG. 14.

It can be seen from the data presented herein that defective Sindbis virus vectors which are produced using the novel DM-Helper plasmid disclosed herein have acquired the improved binding characteristics of the Mut-4 vector and production of higher titers of the JT vector.

DM-HELPER SEQUENCE (6746 bp)

SEQ ID NO: 41

GGATATAGTGGTGAGTATCCCCGCCTGTCATGCGGGAGACCGGGGTTCGG

TTCCCCGACGGGGAGCCAAACAGCCGACCAATTGCACTACCATCACAATG

GAGAAGCCAGTAGTAAACGTAGACGTAGACCCCCAGAGTCCGTTTGTCGT

GCAACTGCAAAAAAGCTTCCCGCAATTTGAGGTAGTAGCACAGCAGGTCA

CTCCAAATGACCATGCTAATGCCAGAGCATTTTCGCATCTGGCCAGTAAA

CTAATCGAGCTGGAGGTTCCTACCACAGCGACGATCTTGGACATAGGCAG

CGCACCGGCTCGTAGAATGTTTTCCGAGCACCAGTATCATTGTGTCTGCC

CCATGCGTAGTCCAGAAGACCCGGACCGCATGATGAAATATGCCAGTAAA

CTGGCGGAAAAAGCGTGCAAGATTACAAACAAGAACTTGCATGAGAAGAT

TAAGGATCTCCGGATCCCCTGAAAAGGCTGTTTAAGTTGGGTAAACCGCT

CCCAGCCGACGACGAGCAAGACGAAGACAGAAGACGCGCTCTGCTAGATG

AAACAAAGGCGTGGTTTAGAGTAGGTATAACAGGCACTTTAGCAGTGGCC

GTGACGACCCGGTATGAGGTAGACAATATTACACCTGTCCTACTGGCATT

GAGAACTTTTGCCCAGAGCAAAAGAGCATTCCAAGCCATCAGAGGGGAAA

TAAAGCATCTCTACGGTGGTCCTAAATAGTCAGCATAGTACATTTCATCT

GACTAATACTACAACACCACCACCATGAATAGAGGATTCTTTAACATGCT

CGGCCGCCGCCCCTTCCCGGCCCCCACTGCCATGTGGAGGCCGCGGAGAA

GGAGGCAGGCGGCCCCGATGCCTGCCCGCAACGGGCTGGCTTCTCAAATC

-continued

```
CAGCAACTGACCACAGCCGTCAGTGCCCTAGTCATTGGACAGGCAACTAG
ACCTCAACCCCCACGTCCACGCCAGCCACCGCGCCAGAAGAAGCAGGCGC
CCAAGCAACCACCGAAGCCGAAGAAACCAAAAACGCAGGAGAAGAAGAAG
AAGCAACCTGCAAAACCCAAACCCGGAAAGAGACAGCGCATGGCACTTAA
GTTGGAGGCCGACAGATTGTTCGACGTCAAGAACGAGGACGGAGATGTCA
TCGGGCACGCACTGGCCATGGAAGGAAAGGTAATGAAACCTCTGCACGTG
AAAGGAACCATCGACCACCCTGTGCTATCAAAGCTCAAATTTACCAAGTC
GTCAGCATACGACATGGAGTTCGCACAGTTGCCAGTCAACATGAGAAGTG
AGGCATTCACCTACACCAGTGAACACCCCGAAGGATTCTATAACTGGCAC
CACGGAGCGGTGCAGTATAGTGGAGGTAGATTTACCATCCCTCGCGGAGT
AGGAGGCAGAGGAGACAGCGGTCGTCCGATCATGGATAACTCCGGTCGGG
TTGTCGCGATAGTCCTCGGTGGAGCTGATGAAGGAACACGAACTGCCCTT
TCGGTCGTCACCTGGAATAGTAAAGGGAAGACAATTAAGACGACCCCGGA
AGGGACAGAAGAGTGGTCCGCAGCACCACTGGTCACGGCAATGTGTTTGC
TCGGAAATGTGAGCTTCCCATGCGACCGCCCGCCCACATGCTATACCCGC
GAACCTTCCAGAGCCCTCGACATCCTTGAAGAGAACGTGAACCATGAGGC
CTACGATACCCTGCTCAATGCCATATTGCGGTGCGGATCGTCTGGCAGAA
GCAAAAGAAGCGTCATCGATGACTTTACCCTGACCAGCCCCTACTTGGGC
ACATGCTCGTACTGCCACCATACTGAACCGTGCTTCAGCCCTGTTAAGAT
CGAGCAGGTCTGGGACGAAGCGGACGATAACACCATACGCATACAGACTT
CCGCCCAGTTTGGATACGACCAAAGCGGAGCAGCAAGCGCAAACAAGTAC
CGCTACATGTCGCTTAAGCAGGATCACACCGTTAAAGAAGGCACCATGGA
TGACATCAAGATTAGCACCTCAGGACCGTGTAGAAGGCTTAGCTACAAAG
GATACTTTCTCCTCGCAAAATGCCCTCCAGGGGACAGCGTAACGGTTAGC
ATAGTGAGTAGCAACTCAGCAACGTCATGTACACTGGCCCGCAAGATAAA
ACCAAAATTCGTGGGACGGAAAAATATGATCTACCTCCCGTTCACGGTA
AAAAAATTCCTTGCACAGTGTACGACCGTCTGAAAGAAACAACTGCAGGC
TACATCACTATGCACAGGCCGGGCCCGCACGCTTATACATCCTACCTGGA
AGAATCATCAGGGAAAGTTTACGCAAAGCCGCCATCTGGGAAGAACATTA
CGTATGAGTGCAAGTGCGGCGACTACAAGACCGGAACCGTTTCGACCCGC
ACCGAAATCACTGGTTGCACCGCCATCAAGCAGTGCGTCGCCTATAAGAG
CGACCAAACGAAGTGGGTCTTCAACTCACCGGACTTGATCCGACATGACG
ACCACACGGTCCAAGGGAAATTGCATTTGCCTTTCAAGTTGATCCCGAGT
ACCTGCATGGTCCCTGTTGCCCACGCGCCGAATGTAATACATGGCTTTAA
ACACATCAGCCTCCAATTAGATACAGACCACTTGACATTGCTCACCACCA
GGAGACTAGGGGCAAACCCGGAACCAACCACTGAATGGATCGTCGGAAAG
ACGGTCAGAAACTTCACCGTCGACCGAGATGGCCTGGAATACATATGGGG
AAATCATGAGCCAGTGAGGGTCTATGCCCAAGAGTCAGCACCAGGAGACC
CTCACGGATGGCCACACGAAATAGTACAGCATTACTACCATCGCCATCCT
GTGTACACCATCTTAGCCGTCGCATCAGCTACCGTGGCGATGATGATTGG
CGTAACTGTTGCAGTGTTATGTGCCTGTAAAGCGCGCCGTGAGTGCCTGA
CGCCATACGCCCTGGCCCCAAACGCCGTAATCCCAACTTCGCTGGCACTC
TTGTGCTGCGTTAGGTCGGCCAATGCTGAAACGTTCACCGAGACCATGAG
TTACTTGTGGTCGAACAGTCAGCCGTTCTTCTGGGTCCAGTTGTGCATAC
CTTTGGCCGCTTTCATCGTTCTAATGCGCTGCTGCTCCTGCTGCCTGCCT
TTTTTAGTGGTTGCCGGCGCCTACCTGGCGAAGGTAGACGCCTACGAACA
TGCGACCACTGTTCCAAATGTGCCACAGATACCGTATAAGGCACTTGTTG
AAAGGGCAGGGTATGCCCCGCTCAATTTGGAGATCACTGTCATGTCCTCG
GAGGTTTTGCCTTCCACCAACCAAGAGTACATTACCTGCAAATTCACCAC
TGTGGTCCCCTCCCCAAAAATCAAATGCTGCGGCTCCTTGGAATGTCAGC
CGGCCGCGCATGCAGGGTATACCTGCAAGGTCTTCGGAGGGGTCTACCCC
TTTATGTGGGGAGGAGCGCAATGTTTTTGCGACAGTGAGAACAGCCAGAT
GAGTGAGGCGTACGTCGAACTGTCAGCAGATTGCGCGTCTGACCACGCGC
AGGCGATTAAGGTGCACACTGCCGCGATGAAAGTAGGACTGCGTATAGTG
TACGGGAACACTACCAGTTTCCTAGATGTGTACGTGAACGGAGTCACACC
AGGAACGTCTAAAGACTTGAAAGTCATAGCTGGACCAATTTCAGCATCGT
TTACGCCATTCGATCATAAGGTCGTTATCCATCGCGGCCTGGTGTACAAC
TATGACTTCCCGGAATATGGAGCGATGAAACCAGGAGCGTTTGGAGACAT
TCAAGCTACCTCCTTGACTAGCAAGGATCTCATCGCCAGCACAGACATTA
GGCTACTCAAGCCTTCCGCCAAGAACGTGCATGTCCCGTACACGCAGGCC
TCTTCAGGATTTGAGATGTGGAAAAACAACTCAGGCCGCCCACTGCAGGA
AACCGCACCTTTCGGGTGTAAGATTGCAGTAAATCCGCTCCGAGCGGTGG
ACTGTTCATACGGGAACATTCCCATTTCTATTGACATCCCGAACGCTGCC
TTTATCAGGACATCAGATGCACCACTGGTCTCAACAGTCAAATGTGAAGT
CAGTGAGTGCACTTATTCAGCAGACTTCGGCGGGATGGCCACCCTGCAGT
ATGTATCCGACCGCGAAGGTCAATGCCCCGTACATTCGCATTCGAGCACA
GCAACTCTCCAAGAGTCGACAGTACATGTCCTGGAGAAAGGAGCGGTGAC
AGTACACTTTAGCACCGCGAGTCCACAGGCGAACTTTATCGTATCGCTGT
GTGGGAAGAAGACAACATGCAATGCAGAATGTAAACCACCAGCTGACCAT
ATCGTGAGCACCCCGCACAAAAATGACCAAGAATTTCAAGCCGCCATCTC
AAAAACATCATGGAGTTGGCTGTTTGCCCTTTTCGGCGGCGCCTCGTCGC
TATTAATTATAGGACTTATGATTTTTGCTTGCAGCATGATGCTGACTAGC
ACACGAAGATGACCGCTACGCCCCAATGATCCGACCAGCAAAACTCGATG
TACTTCCGAGGAACTGATGTGCATAATGCATCAGGCTGGTACATTAGATC
CCCGCTTACCGCGGGCAATATAGCAACACTAAAAACTCGATGTACTTCCG
AGGAAGCGCAGTGCATAATGCTGCGCAGTGTTGCCACATAACCACTATAT
TAACCATTTATCTAGCGGACGCCAAAAACTCAATGTATTTCTGAGGAAGC
GTGGTGCATAATGCCACGCAGCGTCTGCATAACTTTTATTATTTCTTTTA
TTAATCAACAAAATTTTGTTTTTAACATTTCAAAAAAAAAAAAAAAAAAA
AAAAAAAAAAAAAAAAAAAATTTAAATTAATTAAGCGGCCGCCTCGAGGAC
GTCAGGTGGCACTTTTCGGGGAAATGTGCGCGGAACCCCTATTTGTTTAT
```

-continued

```
TTTTCTAAATACATTCAAATATGTATCCGCTCATGAGACAATAACCCTGA
TAAATGCTTCAATAATATTGAAAAAGGAAGAGTATGAGTATTCAACATTT
CCGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGGGT
GCACGAGTGGGTTACATCGAACTGGATCTCAACAGCGGTAAGATCCTTGA
GAGTTTTCGCCCCGAAGAACGTTTTCCAATGATGAGCACTTTTAAAGTTC
TGCTATGTGGCGCGGTATTATCCCGTATTGACGCCGGGCAAGAGCAACTC
GGTCGCCGCATACACTATTCTCAGAATGACTTGGTTGAGTACTCACCAGT
CACAGAAAAGCATCTTACGGATGGCATGACAGTAAGAGAATTATGCAGTG
CTGCCATAACCATGAGTGATAACACTGCGGCCAACTTACTTCTGACAACG
ATCGGAGGACCGAAGGAGCTAACCGCTTTTTTGCACAACATGGGGGATCA
TGTAACTCGCCTTGATCGTTGGGAACCGGAGCTGAATGAAGCCATACCAA
ACGACGAGCGTGACACCACGATGCCTGTAGCAATGGCAACAACGTTGCGC
AAACTATTAACTGGCGAACTACTTACTCTAGCTTCCCGGCAACAATTAAT
AGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTAT
CGTAGTTATCTACACGACGGGGAGTCAGGCAACTATGGATGAACGAAATA
GACAGATCGCTGAGATAGGTGCCTCACTGATTAAGCATTGGTAACTGTCA
GACCAAGTTTACTCATATATACTTTAGATTGATTTAAAACTTCATTTTTA
ATTTAAAAGGATCTAGGTGAAGATCCTTTTTGATAATCTCATGACCAAAA
TCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTT
GCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAA
CTCTGTAGCACCGCCTACATACCTCGCTCTGCTAATCCTGTTACCAGTGG
CTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCAC
ACAGCCCAGCTTGGAGCGAACGACCTACACCGAACTGAGATACCTACAGC
GTGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCT
GACTTGAGCGTCGATTTTTGTGATGCTCGTCAGGGGGCGGAGCCTATGG
AAAAACGCCAGCAACGCGGCCTTTTTACGGTTCCTGGCCTTTTGCTGGCC
TTTTGCTCACATGTGGGAGCCTAGGGTACATTTAGGTGACACTATA
```

References for Example 5

20.—Schlesinger, S., R. Levis, B. G. Weiss, M. Tsiang, and H. Huang. 1987. Replication and packaging sequences in defective interfering RNAs of Sindbis virus, p. 241-250. In M. A. Brinton and R. R. Rueckert (ed.), Positive strand RNA viruses. Alan R. Liss, New York.

21 Sindbis virus expression vectors: packaging of RNA replicons by using defective helper RNAs. Bredenbeck P J, Frolov I, Rice C M, Schlesinger S. J Virol. 1993 November; 67 (11):6439-46.

Example 6

Generation of Plasmid T7DM-Helper#101

The T7DM-Helper#101 plasmid is derived from the DM-helper plasmid described above in Example 5. The Sindbis sequence that is transcribed in vitro from this plasmid to make the RNA for electroporation is the same as the DMHelper. The difference is that the SP6 promoter was replaced by the T7 promoter and two EcoRV restriction sites were added flanking the T7-Sindbis sequence, to allow for subcloning this fragments in other vectors.

Summary of Cloning Strategy

Step 1: Oligos were generated from the sequence: AvrII-EcoRV-T7-Sindbis5end-MfeI and clone in the TOPO vector. Plasmid T1

Step 2: The EcoRV restriction site was inserted in the 3' end of the Sindbis sequence in the DMHelper plasmid, after the XhoI site used to linearize the DNA for in vitro transcription. Plasmid EcoRV_DMHelper#6

Step 3: The AvrII-5end-MfeI fragment was cloned into the plasmid generated in step 2. Plasmid T7DM-Helper#101.

T7DM-Helper#101 Cloning

Plasmid T1.

The reaction mix of primers T7-5End-F and T7-5End-R (4.4 ug/each) in water, was boiled for 1 min and cooled down to RT for primer annealing.

One hundred ng of the primer mix was ligated to the pcr4blunt_topo vector (Invitrogen, San Diego, Calif.) to make the new plasmid T1. The oligo insert was sequenced.

Plasmid EcoRV_DMHelper#6

The EcoRV_DMHelper#6 helper mas made from plasmid DM-Helper is using the QuickChange IIx site-directed mutagenesis kit following the manufacturer's instructions (Stratagene, La Jolla, Calif.). Briefly, 20 ng of DM-Helper were incubated with complementary primers: EcoRV-End-F/EcoRV-End-R, reaction buffer, dNTPs and 2.5 units of pfu Ultra HF DNA polymerase. PCR reactions were 95° C. 1 min, 18 cycles of 95° C. 50 s, 60° C. 50 s, 68° C. 13.5 min, and final elongation of 68° C. 7 min.

After the PCR reactions, 10 U of restriction enzyme DpnI was added and the reaction was incubated at 37° C. for 2 hours to digest the methylated parental DNA. XL-10-Gold competent E. coli cells were transformed and the colonies analyzed by restriction EcoRV enzyme digestion. Mutations in the new plasmid were verified by sequencing.

Plasmid T7DM-Helper#101.

The T1 Plasmid was digested with enzymes AvrII and MfeI O/N at 37° C. The 130 bp band was isolated from an agarose gel and ligated in the AvrII and MfeI digested EcoRV_DM-Helper#6 plasmid. E. coli DH5-α cells were transformed with the ligation and colonies were screened by AvrII/MfeI digestion. The new plasmid, T7DM-Helper#101, was fully sequenced.

TABLE 1

| PRIMER | SEQUENCE | RE |
|---|---|---|
| T7-5End-F | GATCCTAGGATATCAACAGCTATGACATGATTACGAATT<br>TAATACGACTCACTATAGGATATAGTGGTGAGTATCCCCGCCTGT<br>CATGCGGGAGACCGGGGTTCGGTTCCCCGACGGGGAGCCAAACA<br>GCCGACCAATTGCAC<br>(SEQ ID NO: 56) | AvrII<br>EcoRV<br>MfeI |
| T7-5End-R | GTGCAATTGGTCGGCTGTTTGGCTC-<br>CCCGTCGGGGAACCGAACCC<br>CGGTCTCCCGCATGACAGGCGGG-<br>GATACTCACCACTATATCCTAT<br>AGTGAGTCGTATTAAATTCGTAATCAT-<br>GTCATAGCTGTTGATATC<br>CTAGGATC (SEQ ID NO: 57) | |
| EcoRV-End-F | GCGGCCGCCTCGAGGACGGATATCGCACTTTTCGGGGAAA<br>(SEQ ID NO: 58) | XhoI<br>EcoRV |
| EcoRV-End-R | TTTCCCCGAAAAGTGCGATATCACGTCCTCGAGGCGGCCGC<br>(SEQ ID NO: 59) | EcoRV<br>XhoI | primers used to generate T7DM-Helper #101 vector. Shaded T7 promote sequence

```
Plasmid T7DM-Helper#101 sequece (6771 bp):
(SEQ ID NO: 60)
GGATATAGTGGTGAGTATCCCCGCCTGTCATGCGGGAGACCGGGGTTCGG

TTCCCCGACGGGGAGCCAAACAGCCGACCAATTGCACTACCATCACAATG

GAGAAGCCAGTAGTAAACGTAGACGTAGACCCCCAGAGTCCGTTTGTCGT

GCAACTGCAAAAAGCTTCCCGCAATTTGAGGTAGTAGCACAGCAGGTCA

CTCCAAATGACCATGCTAATGCCAGAGCATTTTCGCATCTGGCCAGTAAA

CTAATCGAGCTGGAGGTTCCTACCACAGCGACGATCTTGGACATAGGCAG

CGCACCGGCTCGTAGAATGTTTTCCGAGCACCAGTATCATTGTGTCTGCC

CCATGCGTAGTCCAGAAGACCCGGACCGCATGATGAAATATGCCAGTAAA

CTGGCGGAAAAAGCGTGCAAGATTACAAACAAGAACTTGCATGAGAAGAT

TAAGGATCTCCGGATCCCCTGAAAAGGCTGTTTAAGTTGGGTAAACCGCT

CCCAGCCGACGACGAGCAAGACGAAGACAGAAGACGCGCTCTGCTAGATG

AAACAAAGGCGTGGTTTAGAGTAGGTATAACAGGCACTTTAGCAGTGGCC

GTGACGACCCGGTATGAGGTAGACAATATTACACCTGTCCTACTGGCATT

GAGAACTTTTGCCCAGAGCAAAAGAGCATTCCAAGCCATCAGAGGGGAAA

TAAAGCATCTCTACGGTGGTCCTAAATAGTCAGCATAGTACATTTCATCT

GACTAATACTACAACACCACCACCATGAATAGAGGATTCTTTAACATGCT

CGGCCGCCGCCCCTTCCCGGCCCCCACTGCCATGTGGAGGCCGCGGAGAA

GGAGGCAGGCGGCCCCGATGCCTGCCCGCAACGGGCTGGCTTCTCAAATC

CAGCAACTGACCACAGCCGTCAGTGCCCTAGTCATTGGACAGGCAACTAG

ACCTCAACCCCCACGTCCACGCCAGCCACCGCGCCAGAAGAAGCAGGCGC

CCAAGCAACCACCGAAGCCGAAGAAACCAAAAACGCAGGAGAAGAAGAAG

AAGCAACCTGCAAAACCCAAACCCGGAAAGAGACAGCGCATGGCACTTAA

GTTGGAGGCCGACAGATTGTTCGACGTCAAGAACGAGGACGGAGATGTCA

TCGGGCACGCACTGGCCATGGAAGGAAAGGTAATGAAACCTCTGCACGTG

AAAGGAACCATCGACCACCCTGTGCTATCAAAGCTCAAATTTACCAAGTC

GTCAGCATACGACATGGAGTTCGCACAGTTGCCAGTCAACATGAGAAGTG

AGGCATTCACCTACACCAGTGAACACCCCGAAGGATTCTATAACTGGCAC

CACGGAGCGGTGCAGTATAGTGGAGGTAGATTTACCATCCCTCGCGGAGT

AGGAGGCAGAGGAGACAGCGGTCGTCCGATCATGGATAACTCCGGTCGGG

TTGTCGCGATAGTCCTCGGTGGAGCTGATGAAGGAACACGAACTGCCCTT

TCGGTCGTCACCTGGAATAGTAAAGGGAAGACAATTAAGACGACCCCGGA

AGGGACAGAAGAGTGGTCCGCAGCACCACTGGTCACGGCAATGTGTTTGC

TCGGAAATGTGAGCTTCCCATGCGACCGCCCGCCCACATGCTATACCCGC

GAACCTTCCAGAGCCCTCGACATCCTTGAAGAGAACGTGAACCATGAGGC

CTACGATACCCTGCTCAATGCCATATTGCGGTGCGGATCGTCTGGCAGAA

GCAAAAGAAGCGTCATCGATGACTTTACCCTGACCAGCCCCTACTTGGGC

ACATGCTCGTACTGCCACCATACTGAACCGTGCTTCAGCCCTGTTAAGAT

CGAGCAGGTCTGGGACGAAGCGGACGATAACACCATACGCATACAGACTT

CCGCCCAGTTTGGATACGACCAAAGCGGAGCAGCAAGCGCAAACAAGTAC

CGCTACATGTCGCTTAAGCAGGATCACACCGTTAAAGAAGGCACCATGGA

TGACATCAAGATTAGCACCTCAGGACCGTGTAGAAGGCTTAGCTACAAAG

GATACTTTCTCCTCGCAAAATGCCCTCCAGGGGACAGCGTAACGGTTAGC

ATAGTGAGTAGCAACTCAGCAACGTCATGTACACTGGCCCGCAAGATAAA

ACCAAAATTCGTGGGACGGGAAAAATATGATCTACCTCCCGTTCACGGTA

AAAAAATTCCTTGCACAGTGTACGACCGTCTGAAAGAAACAACTGCAGGC

TACATCACTATGCACAGGCCGGGCCCGCACGCTTATACATCCTACCTGGA

AGAATCATCAGGGAAAGTTTACGCAAAGCCGCCATCTGGGAAGAACATTA

CGTATGAGTGCAAGTGCGGCGACTACAAGACCGGAACGGTTTCGACCCGC

ACCGAAATCACTGGTTGCACCGCCATCAAGCAGTGCGTCGCCTATAAGAG

CGACCAAACGAAGTGGGTCTTCAACTCACCGGACTTGATCCGACATGACG

ACCACACGGTCCAAGGGAAATTGCATTTGCCTTTCAAGTTGATCCCGAGT

ACCTGCATGGTCCCTGTTGCCCACGCGCCGAATGTAATACATGGCTTTAA

ACACATCAGCCTCCAATTAGATACAGACCACTTGACATTGCTCACCACCA

GGAGACTAGGGGCAAACCCGGAACCAACCACTGAATGGATCGTCGGAAAG

ACGGTCAGAAACTTCACCGTCGACCGAGATGGCCTGGAATACATATGGGG
```

```
AAATCATGAGCCAGTGAGGGTCTATGCCCAAGAGTCAGCACCAGGAGACC
CTCACGGATGGCCACACGAAATAGTACAGCATTACTACCATCGCCATCCT
GTGTACACCATCTTAGCCGTCGCATCAGCTACCGTGGCGATGATGATTGG
CGTAACTGTTGCAGTGTTATGTGCCTGTAAAGCGCGCCGTGAGTGCCTGA
CGCCATACGCCCTGGCCCCAAACGCCGTAATCCCAACTTCGCTGGCACTC
TTGTGCTGCGTTAGGTCGGCCAATGCTGAAACGTTCACCGAGACCATGAG
TTACTTGTGGTCGAACAGTCAGCCGTTCTTCTGGGTCCAGTTGTGCATAC
CTTTGGCCGCTTTCATCGTTCTAATGCGCTGCTGCTCCTGCTGCCTGCCT
TTTTTAGTGGTTGCCGGCGCCTACCTGGCGAAGGTAGACGCCTACGAACA
TGCGACCACTGTTCCAAATGTGCCACAGATAGCGTATAAGGCACTTGTTG
AAAGGGCAGGGTATGCCCCGCTCAATTTGGAGATCACTGTCATGTGCTCG
GAGGTTTTGCCTTCCACCAACCAAGAGTACATTACCTGCAAATTCACCAC
TGTGGTCCCCTCCCCAAAAATCAAATGCTGCGGCTCCTTGGAATGTCAGC
CGGCCGCGCATGCAGGGTATACCTGCAAGGTCTTCGGAGGGGTCTACCCC
TTTATGTGGGGAGGAGCGCAATGTTTTGCGACAGTGAGAACAGCCAGAT
GAGTGAGGCGTACGTCGAACTGTCAGCAGATTGCGCGTCTGACCACGCGC
AGGCGATTAAGGTGCACACTGCCGCGATGAAAGTAGGACTGGGTATAGTG
TACGGGAACACTACCAGTTTCCTAGATGTGTACGTGAACGGAGTCACACC
AGGAACGTCTAAAGACTTGAAAGTCATAGCTGGACCAATTTCAGCATCGT
TTACGCCATTCGATCATAAGGTCGTTATCCATCGCGGCCTGGTGTACAAC
TATGACTTCCCGGAATATGGAGCGATGAAACCAGGAGCGTTTGGAGACAT
TCAAGCTACCTCCTTGACTAGCAAGGATCTCATCGCCAGCACAGACATTA
GGCTACTCAAGCCTTCCGCCAAGAACGTGCATGTCCCGTACACGCAGGCC
TCTTCAGGATTTGAGATGTGGAAAAACAACTCAGGCCGCCCACTGCAGGA
AACCGCACCTTTCGGGTGTAAGATTGCAGTAAATCCGCTCCGAGCGGTGG
ACTGTTCATACGGGAACATTCCCATTTCTATTGACATCCCGAACGCTGCC
TTTATCAGGACATCAGATGCACCACTGGTCTCAACAGTCAAATGTGAAGT
CAGTGAGTGCACTTATTCAGCAGACTTCGGCGGGATGGCCACCCTGCAGT
ATGTATCCGACCGCGAAGGTCAATGCCCCGTACATTCGCATTCGAGCACA
GCAACTCTCCAAGAGTCGACACTACATGTCCTGGAGAAAGGAGCGGTGAC
AGTACACTTTAGCACCGCGAGTCCACAGGCGAACTTTATCGTATCGCTGT
GTGGGAAGAAGACAACATGCAATGCAGAATGTAAACCACCAGCTGACCAT
ATCGTGAGCACCCCGCACAAAAATGACCAAGAATTTCAAGCCGCCATCTC
AAAAACATCATGGAGTTGGCTGTTTGCCCTTTTCGGCGGCGCCTCGTCGC
TATTAATTATAGGACTTATGATTTTTGCTTGCAGCATGATGCTGACTAGC
ACACGAAGATGACCGCTACGCCCCAATGATCCGACCAGCAAAACTCGATG
TACTTCCGAGGAACTGATGTGCATAATGCATCAGGCTGGTACATTAGATC
CCCGCTTACCGCGGGCAATATAGCAACACTAAAAACTCGATGTACTTCCG
AGGAAGCGCAGTGCATAATGCTGCGCAGTGTTGCCACATAACCACTATAT
TAACCATTTATCTAGCGGACGCCAAAAACTCAATGTATTTCTGAGGAAGC
GTGGTGCATAATGCCACGCAGCGTCTGCATAACTTTTATTATTTCTTTTA
TTAATCAACAAAATTTTGTTTTTAACATTTCAAAAAAAAAAAAAAAAAA
AAAAAAAAAAAAAAAAAAATTTAAATTAATTAAGCGGCCGCCTCGAGGACG
TGATATCGCACTTTTCGGGGAAATGTGCGCGGAACCCCTATTTGTTTATT
TTTCTAAATACATTCAAATATGTATCCGCTCATGAGACAATAACCCTGAT
AAATGCTTCAATAATATTGAAAAAGGAAGAGTATGAGTATTCAACATTTC
CGTGTCGCCCTTATTCCCTTTTTGCGGCATTTTGCCTTCCTGTTTTTGC
TCACCCAGAAACGCTGGTGAAAGTAAAAGATGCTGAAGATCAGTTGGGTG
CACGAGTGGGTTACATCGAACTGGATCTCAACAGCGGTAAGATCCTTGAG
AGTTTTCGCCCCGAAGAACGTTTTCCAATGATGAGCACTTTTAAAGTTCT
GCTATGTGGCGCGGTATTATCCCGTATTGACGCCGGGCAAGAGCAACTCG
GTCGCCGCATACACTATTCTCAGAATGACTTGGTTGAGTACTCACCAGTC
ACAGAAAAGCATCTTACGGATGGCATGACAGTAAGAGAATTATGCAGTGC
TGCCATAACCATGAGTGATAACACTGCGGCCAACTTACTTCTGACAACGA
TCGGAGGACCGAAGGAGCTAACCGCTTTTTTGCACAACATGGGGGATCAT
GTAACTCGCCTTGATCGTTGGGAACCGGAGCTGAATGAAGCCATACCAAA
CGACGAGCGTGACACCACGATGCCTGTAGCAATGGCAACAACGTTGCGCA
AACTATTAACTGGCGAACTACTTACTCTAGCTTCCCGGCAACAATTAATA
GACTGGATGGAGGCGGATAAAGTTGCAGGACCACTTCTGCGCTCGGCCCT
TCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATC
GTAGTTATCTACACGACGGGGAGTCAGGCAACTATGGATGAACGAAATAG
ACAGATCGCTGAGATAGGTGCCTCACTGATTAAGCATTGGTAACTGTCAG
ACCAAGTTTACTCATATATACTTTAGATTGATTTAAAACTTCATTTTTAA
TTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGA
TCAAAGGATCTTCTTGAGATCCTTTTTTTCTGCGCGTAATCTGCTGCTTG
CAAACAAAAAAACCACCGCTACCAGCGGTGGTTTGTTTGCCGGATCAAGA
GCTACCAACTCTTTTTCCGAAGGTAACTGGCTTCAGCAGAGCGCAGATAC
CAAATACTGTCCTTCTAGTGTAGCCGTAGTTAGGCCACCACTTCAAGAAC
TCTGTAGCACCGCCTACATACCTCGCTCTGCTAATCCTGTTACCAGTGGC
TGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACA
CAGCCCAGCTTGGAGCGAACGACCTACACCGAACTGAGATACCTACAGCG
TGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCA
GGGGGAAACGCCTGGTATCTTTATAGTCCTGTCGGGTTTCGCCACCTCTG
ACTTGAGCGTCGATTTTTGTGATGCTCGTCAGGGGGGCGGAGCCTATGG
AAAAACGCCAGCAACGCGGCCTTTTTACGGTTCCTGGCCTTTTGCTGGCC
TTTTGCTCACATGTGGGAGCCTAGGATATCAACAGCTATGACATGATTAC
GAATTTAATACGACTCACTATA
```

Example 7

Generation of Plasmid T7StuI-RLacZ#22

The T7StuI-RLacZ#22 plasmid is derived from the T7-RLacZ#202 plasmid. The Sindbis sequence that is transcribed in vitro from this plasmid to make the RNA for electroporation is the same as for T7-RLacZ#202. Two StuI restriction sites were added flanking the T7-Sindbis sequence, to allow for subcloning this fragments in other vectors.

The double mutant T7-StuI-RLacZ#202 plasmid was made by mutagenesis of plasmid T7-RLacZ#202 in two steps: first by introducing a StuI Restriction site in the 5' end to make the 5-StuIRLacZ#2 plasmid, and second using this new vector to mutagenize the 3' end.

Double mutations were made on plasmid T7-StuI-RLacZ#202 using the QuickChange IIx site-directed mutagenesis kit by following the manufacturer's instructions (Stratagene, La Jolla, Calif.). Briefly, 20 ng of T7-StuI-RLacZ#202 were incubated with complementary primers: 5-T7LZ-StuIF/5-T7LZ-StuIR, reaction buffer, dNTPs and 2.5 units of pfu Ultra HF DNA polymerase. PCR reactions were 95° C. 1 min, 18 cycles of: 95° C. 50 s, 60° C. 50 s, 68° C. 13.5 min, and final elongation of 68° C. 7 min.

After the PCR reactions, 10 U of restriction enzyme DpnI was added and the reaction was incubated at 37° C. for 1 hour to digest the methylated parental DNA. XL-10-Gold competent *E. coli* cells were transformed and the colonies analyzed by restriction enzyme digestion (RE). Mutations in the new plasmid were verified by sequencing.

The final plasmid (T7StuI-RLacZ#22) was made following the same protocol using the new plasmid 5-StuIRLacZ#2 as a template for PCR and primers 3-T7LZ-StuI-F/3-T7LZ-StuI-R.

The sequence of primers used and nt changes are shown in Table 2

TABLE 2

Underline RE sequence. Low case residues mutated

| PRIMER NAME | SEQUENCE | RE SITE |
|---|---|---|
| 5-T7LZ-StuIF | CATGTGGGAGGCctGAGTACTTAATACGACTCACTATAGG (SEQ ID NO: 61) | StuI |
| 5-T7LZ-StuIR | CCTATAGTGAGTCGTATTAAGTACTCagGCCTCCCACATG (SEQ ID NO: 62) | StuI |
| 3-T7LZ-StuIF | CCTCGAGGACGTCAGGTaGgcCTTTTCGGGGAAATGTGC (SEQ ID NO: 63) | StuI |
| 3-T7LZ-StuIR | GCACATTTCCCCGAAAAGgcCtACCTGACGTCCTCGAGG (SEQ ID NO: 64) | StuI |

Plasmid T7StuI-RLacZ#22 sequence (13092 bp)
(SEQ ID NO: 65)
ATTGACGGCGTAGTACACACTATTGAATCAAACAGCCGACCAATTGCACT

ACCATCACAATGGAGAAGCCAGTAGTAAACGTAGACGTAGACCCCCAGAG

TCCGTTTGTCGTGCAACTGCAAAAAAGCTTCCCGCAATTTGAGGTAGTAG

CACAGCAGGTCACTCCAAATGACCATGCTAATGCCAGAGCATTTTCGCAT

CTGGCCAGTAAACTAATCGAGCTGGAGGTTCCTACCACAGCGACGATCTT

GGACATAGGCAGCGCACCGGCTCGTAGAATGTTTTCCGAGCACCAGTATC

ATTGTGTCTGCCCCATGCGTAGTCCAGAAGACCCGGACCGCATGATGAAA

TATGCCAGTAAACTGGCGGAAAAAGCGTGCAAGATTACAAACAAGAACTT

GCATGAGAAGATTAAGGATCTCCGGACCGTACTTGATACGCCGGATGCTG

AAACACCATCGCTCTGCTTTCACAACGATGTTACCTGCAACATGCGTGCC

GAATATTCCGTCATGCAGGACGTGTATATCAACGCTCCCGGAACTATCTA

TCATCAGGCTATGAAAGGCGTGCGGACCCTGTACTGGATTGGCTTCGACA

CCACCCAGTTCATGTTCTCGGCTATGGCAGGTTCGTACCCTGCGTACAAC

ACCAACTGGGCCGACGAGAAAGTCCTTGAAGCGCGTAACATCGGACTTTG

CAGCACAAAGCTGAGTGAAGGTAGGACAGGAAAATTGTCGATAATGAGGA

AGAAGGAGTTGAAGCCCGGGTCGCGGGTTTATTTCTCCGTAGGATCGACA

CTTTATCCAGAACACAGAGCCAGCTTGCAGAGCTGGCATCTTCCATCGGT

GTTCCACTTGAATGGAAAGCAGTCGTACACTTGCCGCTGTGATACAGTGG

TGAGTTGCGAAGGCTACGTAGTGAAGAAAATCACCATCAGTCCCGGGATC

ACGGGAGAAACCGTGGGATACGCGGTTACACACAATAGCGAGGGCTTCTT

GCTATGCAAAGTTACTGACACAGTAAAAGGAGAACGGGTATCGTTCCCTG

TGTGCACGTACATCCCGGCCACCATATGCGATCAGATGACTGGTATAATG

GCCACGGATATATCACCTGACGATGCACAAAAACTTCTGGTTGGGCTCAA

CCAGCGAATTGTCATTAACGGTAGGACTAACAGGAACACCAACACCATGC

AAAATTACCTTCTGCCGATCATAGCACAAGGGTTCAGCAAATGGGCTAAG

GAGCGCAAGGATGATCTTGATAACGAGAAAATGCTGGGTACTAGAGAACG

CAAGCTTACGTATGGCTGCTTGTGGGCGTTTCGCACTAAGAAAGTACATT

CGTTTTATCGCCCACCTGGAACGCAGACCATCGTAAAAGTCCCAGCCTCT

TTTAGCGCTTTTCCCATGTCGTCCGTATGGACGACCTCTTTGCCCATGTC

GCTGAGGCAGAAATTGAAACTGGCATTGCAACCAAAGAAGGAGGAAAAAC

TGCTGCAGGTCTCGGAGGAATTAGTCATGGAGGCCAAGGCTGCTTTGGAG

GATGCTCAGGAGGAAGCCAGAGCGGAGAAGCTCCGAGAAGCACTTCCACC

ATTAGTGGCAGACAAAGGCATCGAGGCAGCCGCAGAAGTTGTCTGCGAAG

TGGAGGGGCTCCAGGCGGACATCGGAGCAGCATTAGTTGAAACCCCGCGC

GGTCACGTAAGGATAATACCTCAAGCAAATGACCGTATGATCGGACAGTA

```
TATCGTTGTCTCGCCAAACTCTGTGCTGAAGAATGCCAAACTCGGACCAG
CGCACCCGCTAGCAGATCAGGTTAAGATCATAACACACTCCGGAAGATCA
GGAAGGTACGCGGTCGAACCATACGACGCTAAAGTACTGATGCCAGCAGG
AGGTGCCGTACCATGGCCAGAATTCCTAGCACTGAGTGAGAGCGCCACGT
TAGTGTACAACGAAAGAGAGTTTGTGAACGGCAAACTATACCACATTGCC
ATGCATGGCCCCGCCAAGAATACAGAAGAGGAGCAGTACAAGGTTACAAA
GGCAGAGCTTGCAGAAACAGAGTACGTGTTTGACGTGGACAAGAAGCGTT
GCGTTAAGAAGGAAGAAGCCTCAGGTCTGGTCCTCTCGGGAGAACTGACC
AACCCTCCCTATCATGAGCTAGCTCTGGAGGGACTGAAGACCCGACCTGC
GGTCCCGTACAAGGTCGAAACAATAGGAGTGATAGGCACACCGGGGTCGG
GCAAGTCAGCTATTATCAAGTCAACTGTCACGGCACGAGATCTTGTTACC
AGCGGAAAGAAAGAAAATTGTCGCGAAATTGAGCCCGACGTGCTAAGACT
GAGGGGTATGCAGATTACGTCGAAGACAGTAGATTCGGTTATGCTCAACG
GATGCCACAAAGCCGTAGAAGTGCTGTACGTTGACGAAGCGTTCGCGTGC
CACGCAGGAGCACTACTTGCCTTGATTGCTATCGTCAGGCCCCGCAAGAA
GGTAGTACTATGCGGAGACCCCATGCAATGCGGATTCTTCAACATGATGC
AACTAAAGGTACATTTCAATCACCCTGAAAAAGACATATGCACCAAGACA
TTCTACAAGTATATCTCCCGGCGTTGCACACAGCCAGTTACAGCTATTGT
ATCGACACTGCATTACGATGGAAAGATGAAAACCACGAACCCGTGCAAGA
AGAACATTGAAATCGATATTACAGGGGCCACAAAGCCGAAGCCAGGGGAT
ATCATCCTGACATGTTTCCGCGGGTGGGTTAAGCAATTGCAAATCGACTA
TCCCGGACATGAAGTAATGACAGCCGCGGCCTCACAAGGGCTAACCAGAA
AAGGAGTGTATGCCGTCCGGCAAAAAGTCAATGAAAACCCACTGTACGCG
ATCACATCAGAGCATGTGAACGTGTTGCTCACCCGCACTGAGGACAGGCT
AGTGTGGAAAACC1TGCAGGGCGACCCATGGATTAAGCAGCTCACTAACA
TACCTAAAGGAAACTTTCAGGCTACTATAGAGGACTGGGAAGCTGAACAC
AAGGGAATAATTGCTGCAATAAACAGCCCCACTCCCCGTGCCAATCCGTT
CAGCTGCAAGACCAACGTTTGCTGGGCGAAAGCATTGGAACCGATACTAG
CCACGGCCGGTATCGTACTTACCGGTTGCCAGTGGAGCGAACTGTTCCCA
CAGTTTGCGGATGACAAACCACATTCGGCCATTTACGCCTTAGACGTAAT
TTGCATTAAGTTTTTCGGCATGGACTTGACAAGCGGACTGTTTTCTAAAC
AGAGCATCCCACTAACGTACCATCCCGCCGATTCAGCGAGGCCGGTAGCT
CATTGGGACAACAGCCCAGGAACCCGCAAGTATGGGTACGATCACGCCAT
TGCCGCCGAACTCTCCCGTAGATTTCCGTGTTCCAGCTAGCTGGGAAGG
GCACACAACTTGATTTGCAGACGGGGAGAACCAGAGTTATCTCTGCACAG
CATAACCTGGTCCCGGTGAACCGCAATCTTCCTCACGCCTTAGTCCCCGA
GTACAAGGAGAAGCAACCCGGCCCGGTCGAAAAATTCTTGAACGAGTTCA
AAGACCACTCAGTACTTGTGGTATCAGAGGAAAAAATTGAAGCTCCCCGT
AAGAGAATCGAATGGATCGCCCCGATTGGCATAGCCGGTGCAGATAAGAA
CTACAACCTGGCTTTCGGGTTTCCGCCGCAGGCACGGTACGACCTGGTGT
TCATCAACATTGGAACTAAATACAGAAACCACCACTTTCAGCAGTGCGAA
GACCATGCGGCGACCTTAAAAACCCTTTCGCGTTCGGCCCTGAATTGCCT
TAACCCAGGAGGCACCCTCGTGGTGAAGTCCTATGGCTACGCCGACCGCA
ACAGTGAGGACGTAGTCACCGCTCTTGCCAGAAAGTTTGTCAGGGTGTCT
GCAGCGAGACCAGATTGTGTCTCAAGCAATACAGAAATGTACCTGATTTT
CCGACAACTAGACAACAGCCGTACACGGCAATTCACCCCGCACCATCTGA
ATTGCGTGATTTCGTCCGTGTATGAGGGTACAAGAGATGGAGTTGGAGCC
GCGCCGTCATACCGCACCAAAAGGGAGAATATTGCTGACTGTCAAGAGGA
AGCAGTTGTCAACGCAGCCAATCCGCTGGGTAGACCAGGCGAAGGAGTCT
GCCGTGCCATCTATAAACGTTGGCCGACCAGTTTTACCGATTCAGCCACG
GAGACAGGCACCGCAAGAATGACTGTGTGCCTAGGAAAGAAAGTGATCCA
CGCGGTCGGCCCTGATTTCCGGAAGCACCCAGAAGCAGAAGCCTTGAAAT
TGCTACAAAACGCCTACCATGCAGTGGCAGACTTAGTAAATGAACATAAC
ATCAAGTCTGTCGCCATTCCACTGCTATCTACAGGCATTTACGCAGCCGG
AAAAGACCGCCTTGAAGTATCACTTAACTGCTTGACAACCGCGCTAGACA
GAACTGACGCGGACGTAACCATCTATTGCCTGGATAAGAAGTGGAAGGAA
AGAATCGACGCGGCACTCCAACTTAAGGAGTCTGTAACAGAGCTGAAGGA
TGAAGATATGGAGATCGACGATGAGTTAGTATGGATCCATCCAGACAGTT
GCTTGAAGGGAAGAAAGGGATTCAGTACTACAAAAGGAAAATTGTATTCG
TACTTCGAAGGCACCAAATTCCATCAAGCAGCAAAAGACATGGCGGAGAT
AAAGGTCCTGTTCCCTAATGACCAGGAAAGTAATGAACAACTGTGTGCCT
ACATATTGGGTGAGACCATGGAAGCAATCCGCGAAAAGTGCCCGGTCGAC
CATAACCCGTCGTCTAGCCCGCCCAAAACGTTGCCGTGCCTTTGCATGTA
TGCCATGACGCCAGAAAGGGTCCACAGACTTAGAAGCAATAACGTCAAAG
AAGTTACAGTATGCTCCTCCACCCCCCTTCCTAAGCACAAAATTAAGAAT
GTTCAGAAGGTTCAGTGCACGAAAGTAGTCCTGTTTAATCCGCACACTCC
CGCATTCGTTCCCGCCCGTAAGTACATAGAAGTGCCAGAACAGCCTACCG
CTCCTCCTGCACAGGCCGAGGAGGCCCCCGAAGTTGTAGCGACACCGTCA
CCATCTACAGCTGATAACACCTCGCTTGATGTCACAGACATCTCACTGGA
TATGGATGACAGTAGCGAAGGCTCACTTTTTTCGAGCTTTAGCGGATCGG
ACAACTCTATTACTAGTATGGACAGTTGGTCGTCAGGACCTAGTTCACTA
GAGATAGTAGACCGAAGGCAGGTGGTGGTGGCTGACGTTCATGCCGTCCA
AGAGCCTGCCCCTATTCCACCGCCAAGGCTAAAGAAGATGGCCCGCCTGG
CAGCGGCAAGAAAAGAGCCCACTCCACCGGCAAGCAATAGCTCTGAGTCC
CTCCACCTCTCTTTTGGTGGGTATCCATGTCCCTCGGATCAATTTTCGA
CGGAGAGACGGCCCGCCAGGCAGCGGTACAACCCCTGGCAACAGGCCCCA
CGGATGTGCCTATGTCTTTCGGATCGTTTTCCGACGGAGAGATTGATGAG
CTGAGCCGCAGAGTAACTGAGTCCGAACCCGTCCTGTTTGGATCATTTGA
ACCGGGCGAAGTGAACTCAATTATATCGTCCCGATCAGCCGTATCTTTTC
CACTACGCAAGCAGAGACGTAGACGCAGGAGCAGGAGGACTGAATACTGA
CTAACCGGGGTAGGTGGGTACATATTTTCGACGGACACAGGCCCTGGGCA
```

-continued

CTTGCAAAAGAAGTCCGTTCTGCAGAACCAGCTTACAGAACCGACCTTGG
AGCGCAATGTCCTGGAAAGAATTCATGCCCCGGTGCTCGACACGTCGAAA
GAGGAACAACTCAAACTCAGGTACCAGATGATGCCCACCGAAGCCAACAA
AAGTAGGTACCAGTCTCGTAAAGTAGAAAATCAGAAAGCCATAACCACTG
AGCGACTACTGTCAGGACTACGACTGTATAACTCTGCCACAGATCAGCCA
GAATGCTATAAGATCACCTATCCGAAACCATTGTACTCCAGTAGCGTACC
GGCGAACTACTCCGATCCACAGTTCGCTGTAGCTGTCTGTAACAACTATC
TGCATGAGAACTATCCGACAGTAGCATCTTATCAGATTACTGACGAGTAC
GATGCTTACTTGGATATGGTAGACGGGACAGTCGCCTGCCTGGATACTGC
AACCTTCTGCCCCGCTAAGCTTAGAAGTTACCCGAAAAAACATGAGTATA
GAGCCCCGAATATCCGCAGTGCGGTTCCATCAGCGATGCAGAACACGCTA
CAAAATGTGCTCATTGCCGCAACTAAAAGAAATTGCAACGTCACGCAGAT
GCGTGAACTGCCAACACTGGACTCAGCGACATTCAATGTCGAATGCTTTC
GAAAATATGCATGTAATGACGAGTATTGGGAGGAGTTCGCTCGGAAGCCA
ATTAGGATTACCACTGAGTTTGTCACCGCATATGTAGCTAGACTGAAAGG
CCCTAAGGCCGCCGCACTATTTGCAAAGACGTATAATTTGGTCCCATTGC
AAGAAGTGCCTATGGATAGATTCGTCATGGACATGAAAAGAGACGTGAAA
GTTACACCAGGCACGAAACACACAGAAGAAAGACCGAAAGTACAAGTGAT
ACAAGCCGCAGAACCCCTGGCGACTGCTTACTTATGCGGGATTCACCGGG
AATTAGTGCGTAGGCTTACGGCCGTCTTGCTTCCAAACATTCACACGCTT
TTTGACATGTCGGCGGAGGATTTTGATGCAATCATAGCAGAACACTTCAA
GCAAGGCGACCCGGTACTGGAGACGGATATCGCATCATTCGACAAAAGCC
AAGACGACGCTATGGCGTTAACCGGTCTGATGATCTTGGAGGACCTGGGT
GTGGATCAACCACTAGTCGACTTGATCGAGTGCGCCTTTGGAGAAATATC
ATCCACCCATCTACCTACGGGTACTCGTTTTAAATTCGGGGCGATGATGA
AATCCGGAATGTTCCTCACACTTTTTGTCAACACAGTTTTGAATGTCGTT
ATCGCCAGCAGAGTACTAGAAGAGCGGCTTAAAACGTCCAGATGTGCAGC
GTTCATTGGCGACGACAACATCATACATGGAGTAGTATCTGACAAAGAAA
TGGCTGAGAGGTGCGCCACCTGGCTCAACATGGAGGTTAAGATCATCGAC
GCAGTCATCGGTGAGAGACCACCTTACTTCTGCGGCGGATTTATCTTGCA
AGATTCGGTTACTTCCACAGCGTGCCGCGTGGCGGACCCCCTGAAAAGGC
TGTTTAAGTTGGGTAAACCGCTCCCAGCCGACGACGAGCAAGACGAAGAC
AGAAGACGCGCTCTGCTAGATGAAACAAAGGCGTGGTTTAGAGTAGGTAT
AACAGGCACTTTAGCAGTGGCCGTGACGACCCGGTATGAGGTAGACAATA
TTACACCTGTCCTACTGGCATTGAGAACTTTTGCCCAGAGCAAAAGAGCA
TTCCAAGCCATCAGAGGGGAAATAAAGCATCTGTACGGTGGTCCTAAATA
GTCAGCATAGTACATTTCATCTGACTAATACTACAACACCACCACCTCTA
GACCATGGATCCCGTCGTTTTACAACGTCGTGACTGGGAAAACCCTGGCG
TTACCCAACTTAATCGCCTTGCAGCACATCCCCCTTTCGCCAGCTGGCGT
AATAGCGAAGAGGCCCGCACCGATCGCCCTTCCCAACAGTTGCGCAGCCT

GAATGGCGAATGGCGCTTTGCCTGGTTTCCGGCACCAGAAGCGGTGCCGG
AAAGCTGGCTGGAGTGCGATCTTCCTGAGGCCGATACTGTCGTCGTCCCC
TCAAACTGGCAGATGCACGGTTACGATGGGCCCATCTACACCAACGTGAC
CTATCCCATTACGGTCAATCCGCCGTTTGTTCCCACGGAGAATCCGACGG
GTTGTTACTCGCTCACATTTAATGTTGATGAAAGCTGGCTACAGGAAGGC
CAGACGCGAATTATTTTTGATGGCGTTAACTCGGCGTTTCATCTGTGGTG
CAACGGGCGCTGGGTCGGTTACGGCCAGGACAGTCGTTTGCCGTCTGAAT
TTGACCTGAGCGCATTTTTACGCGCCGGAGAAAACCGCCTCGCGGTGATG
GTGCTGCGCTGGAGTGACGGCAGTTATCTGGAAGATCAGGATATGTGGCG
GATGAGCGGCATTTTCCGTGACGTCTCGTTGCTGCATAAACCGACTACAC
AAATCAGCGATTTCCATGTTGCCACTCGCTTTAATGATGATTTCAGCCGC
GCTGTACTGGAGGCTGAAGTTCAGATGTGCGGCGAGTTGCGTGACTACCT
ACGGGTAACAGTTTCTTTATGGCAGGGTGAAACGCAGGTCGCCAGCGGCA
CCGCGCCTTTCGGCGGTGAAATTATCGATGAGCGTGGTGGTTATGCCGAT
CGCGTCACACTACGTCTGAACGTCGAAAACCCGAAACTGTGGAGCGCCGA
AATCCCGAATCTCTATCGTGCGGTGGTTGAACTGCACACCGCCGACGGCA
CGCTGATTGAAGCAGAAGCCTGCGATGTCGGTTTCCGCGAGGTGCGGATT
GAAAATGGTCTGCTGCTGCTGAACGGCAAGCCGTTGCTGATTCGAGGCGT
TAACCGTCACGAGCATCATCCTCTGCATGGTCAGGTCATGGATGAGCAGA
CGATGGTGCAGGATATCCTGCTGATGAAGCAGAACAACTTTAACGCCGTG
CGCTGTTCGCATTATCCGAACCATCCGCTGTGGTACACGCTGTGCGACCG
CTACGGCCTGTATGTGGTGGATGAAGCCAATATTGAAACCCACGGCATGG
TGCCAATGAATCGTCTGACCGATGATCCGCGCTGGCTACCGGCGATGAGC
GAACGCGTAACGCGAATGGTGCAGCGCGATCGTAATCACCCGAGTGTGAT
CATCTGGTCGCTGGGGAATGAATCAGGCCACGGCGCTAATCACGACGCGC
TGTATCGCTGGATCAAATCTGTCGATCCTTCCCGCCCGGTGCAGTATGAA
GGCGGCGGAGCCGACACCACGGCCACCGATATTATTTGCCCGATGTACGC
GCGCGTGGATGAAGACCAGCCCTTCCCGGCTGTGCCGAAATGGTCCATCA
AAAAATGGCTTTCGCTACCTGGAGAGACGCGCCCGCTGATCCTTTGCGAA
TACGCCCACGCGATGGGTAACAGTCTTGGCGGTTTCGCTAAATACTGGCA
GGCGTTTCGTCAGTATCCCCGTTTACAGGGCGGCTTCGTCTGGGACTGGG
TGGATCAGTCGCTGATTAAATATGATGAAAACGGCAACCCGTGGTCGGCT
TACGGCGGTGATTTTGGCGATACGCCGAACGATCGCCAGTTCTGTATGAA
CGGTCTGGTCTTTGCCGACCGCACGCCGCATCCAGCGCTGACGGAAGCAA
AACACCAGCAGCAGTTTTTCCAGTTCCGTTTATCCGGGCAAACCATCGAA
GTGACCAGCGAATACCTGTTCCGTCATAGCGATAACGAGCTCCTGCACTG
GATGGTGGCGCTGGATGGTAAGCCGCTGGCAAGCGGTGAAGTGCCTCTGG
ATGTCGCTCCACAAGGTAAACAGTTGATTGAACTGCCTGAACTACCGCAG
CCGGAGAGCGCCGGGCAACTCTGGCTCACAGTACGCGTAGTGCAACCGAA
CGCGACCGCATGGTCAGAAGCCGGGCACATCAGCGCCTGGCAGCAGTGGC
GTCTGGCGGAAAACCTCAGTGTGACGCTCCCCGCCGCGTCCCACGCCATC

-continued

```
CCGCATCTGACCACCAGCGAAATGGATTTTTGCATCGAGCTGGGTAATAA
GCGTTGGCAATTTAACCGCCAGTCAGGCTTTCTTTCACAGATGTGGATTG
GCGATAAAAAACAACTGCTGACGCCGCTGCGCGATCAGTTCACCCGTGCA
CCGCTGGATAACGACATTGGCGTAAGTGAAGCGACCCGCATTGACCCTAA
CGCCTGGGTCGAACGCTGGAAGGCGGCGGGCCATTACCAGGCCGAAGCAG
CGTTGTTGCAGTGCACGGCAGATACACTTGCTGATGCGGTGCTGATTACG
ACCGCTCACGCGTGGCAGCATCAGGGGAAAACCTTATTTATCAGCCGGAA
AACCTACCGGATTGATGGTAGTGGTCAAATGGCGATTACCGTTGATGTTG
AAGTGGCGAGCGATACACCGCATCCGGCGCGGATTGGCCTGAACTGCGAG
CTGGCGCAGGTAGCAGAGCGGGTAAACTGGCTCGGATTAGGGCCGCAAGA
AAACTATCCCGACCGCCTTACTGCCGCCTGTTTTGACCGCTGGGATCTGC
CATTGTCAGACATGTATACCCCGTACGTCTTCCCGAGCGAAAACGGTCTG
CGCTGCGGGACGCGCGAATTGAATTATGGCCCACACCAGTGGCGCGGCGA
CTTCCAGTTCAACATCAGCCGCTACAGTCAACAGCAACTGATGGAAACCA
GCCATCGCCATCTGCTGCACGCGGAAGAAGGCACATGGCTGAATATCGAC
GGTTTCCATATGGGGATTGGTGGCGACGACTCCTGGAGCCCGTCAGTATC
GGCGGAATTCCAGCTGAGCGCCGGTCGCTACCATTACCAGTTGGTCTGGT
GTCAAAATAATAATAACCGGGCAGGGGGATCCTAGACGCTACGCCCCA
ATGATCCGACCAGCAAAACTCGATGTACTTCCGAGGAACTGATGTGCATA
ATGCAGGAATTCGATATCAAGCTAGATCTCACGTGAGCATGCGTTTAAAC
TGGGCCCAATGTTCCCCAATGATCCGACCAGCAAAACTCGATGTACTTCC
GAGGAACTGATGTGCATAATGCATCAGGCTGGTACATTAGATCCCCGCTT
ACCGCGGGCAATATAGCAACACTAAAAACTCGATGTACTTCCGAGGAAGC
GCAGTGCATAATGCTGCGCAGTGTTGCCACATAACCACTATATTAACCAT
TTATCTAGCGGACGCCAAAAACTCAATGTATTTCTGAGGAAGCGTGGTGC
ATAATGCCACGCAGCGTCTGCATAACTTTTATTATTTCTTTTATTAATCA
ACAAAATTTTGTTTTTAACATTTCAAAAAAAAAAAAAAAAAAAAAAAAA
AAAAAAAAAAAATTTAAATTAATTAAGCGGCCGCCTCGAGGACGTCAGGT
AGGCCTTTTCGGGGAAATGTGCGCGGAACCCCTATTTGTTTATTTTTCTA
AATACATTCAAATATGTATCCGCTCATGAGACAATAACCCTGATAAATGC
TTCAATAATATTGAAAAGGAAGAGTATGAGTATTCAACATTTCCGTGTC
GCCCTTATTCCCTTTTTTGCGGCATTTTGCCTTCCTGTTTTTGCTCACCC
AGAAACGCTGGTGAAAGTAAAAGATGCTGAAGATGAGTTGGGTGCACGAG
TGGGTTACATCGAACTGGATCTCAACAGCGGTAAGATCCTTGAGAGTTTT
CGCCCCGAAGAACGTTTTCCAATGATGAGCACTTTTAAAGTTCTGCTATG
TGGCGCGGTATTATCCCGTATTGACGCCGGGCAAGAGCAACTCGGTCGCC
GCATACACTATTCTCAGAATGACTTGGTTGAGTACTCACCAGTCACAGAA
AAGCATCTTACGGATGGCATGACAGTAAGAGAATTATGCAGTGCTGCCAT
AACCATGAGTGATAACACTGCGGCCAACTTACTTCTGACAACGATCGGAG
GACCGAAGGAGCTAACCGCTTTTTTGCACAACATGGGGGATCATGTAACT
CGCCTTGATCGTTGGGAACCGGAGCTGAATGAAGCCATACCAAACGACGA
GCGTGACACCACGATGCCTGTAGCAATGGCAACAACGTTGCGCAAACTAT
TAACTGGCGAACTACTTACTCTAGCTTCCCGGCAACAATTAATAGACTGG
ATGGAGGCGGATAAAGTTGCAGGACCACTTCTGCGCTCGGCCCTTCCGGC
TGGCTGGTTTATTGCTGATAAATCTGGAGCCGGTGAGCGTGGGTCTCGCG
GTATCATTGCAGCACTGGGGCCAGATGGTAAGCCCTCCCGTATCGTAGTT
ATCTACACGACGGGGAGTCAGGCAACTATGGATGAACGAAATAGACAGAT
CGCTGAGATAGGTGCCTCACTGATTAAGCATTGGTAACTGTCAGACCAAG
TTTACTCATATATACTTTAGATTGATTTAAAACTTCATTTTTAATTTAAA
AGGATCTAGGTGAAGATCCTTTTTGATAATCTCATGACCAAAATCGCTTA
ACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACA
AAAAAACCACCGCTACCAGCGGTGGTTTGTTTGCCGGATCAAGAGCTACC
AACTCTTTTTCCGAAGGTAACTGGCTTCAGCAGAGCGCAGATACCAAATA
CTGGTCTTCTAGTGTAGCCGTAGTTAGGCCACCACTTCAAGAACTCTGTA
GCACCGCCTACATACCTCGCTCTGCTAATCCTGTTACCAGTGGCTGCTGC
CAGTGGCGATAAGTCGTGTCTTACCGGGTTGGACTCAAGACGATAGTTAC
CGGATAAGGCGCAGCGGTCGGGCTGAACGGGGGGTTCGTGCACACAGCCC
AGCTTGGAGCGAACGACCTACACCGAACTGAGATACCTACAGCGTGAGCT
ATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGA
AACGCCTGGTATCTTTATAGTCCTGTCGGGTTTCGCCACCTCTGACTTGA
GCGTCGATTTTTGTGATGCTCGTCAGGGGGCGGAGCCTATGGAAAAACG
CCAGCAACGCGGCCTTTTTACGGTTCCTGGCCTTTTGCTGGCCTTTTGCT
CACATGTGGGAGGCCTGAGTACTTAATACGACTCACTATAGG
```

TABLE 3

T7StuIR-LacZ (13.092 bp) components

| Nt → nt | Part from: | Description |
|---|---|---|
| 1_7646 | SV 1_7646 | 5' end untranscribed + replicase (nsp1, nsp2, nsp3 and nsp4) + subgenomic promoter |
| 7647_7654 | Oligos | Multi cloning site MCS |
| 7,655_10,711 | Plasmid | LacZ gene (coding for b-galactosidase) |
| 10712_10864 | Oligos | Multi cloning site MCS |
| 10864_11174 | SV 11,393_11,703 | 3' end untranslated region |
|  | Oligos | Multi cloning site MCS |
| 11,236 | Oligos | XhoI Restriction site for linearization |
| 11,254 | Oligos | StuI new restriction site for subcloning |
| 11248_13051 | Bacterial part pUC |  |
| 11,377_12,237 | plasmid | Beta Lactamase (=Amp resistant gene) |
| 12,963_12,999 | plasmid | Bacterial DNA replication origin ColE1 |
| 13051_13092 | Oligos | T7 promoter |
| 13064 | oligos | StuI new restriction site for subcloning |
| 13074_13092 | oligos | T7 core sequence |

Paper Example 1

Production of C6/36 Packaging Cell Line with Rederived Ar-339 Plasmids

Plasmids SP6-H and SP6-R can be used to engineer insect plasmids to generate a mosquito C6/36-derived packaging cell line producing Ar-339 Sindbis vectors. Three plasmids with the Opal2 mosquito promoter (described in Theilmann et al., J. Virology, 1995, 69 (12):7775-7781) are required to constitutively express viral sequences in mosquito cells. The replicon plasmid (pIZ-Ar339-R) will have the replicase, subgenomic promoter and gene of interest and the other two will contain the split helper sequences, one with capsid protein only (PIB-Ar339-C) and the second one with E1, E2, E3 and K6 envelope proteins (pIZ-Ar339-H). In a first step the C6/36 cell line (available from the American Type Culture Collection, ATCC, Manassas, Va. as ATCC CRL 1660) will be transfected with replicon plasmid (pIZ-Ar339-R) and clones will be selected. In a second step the previous clones containing the replicon will be transfected with the capsid plasmid (PIB-Ar339-C) and replicon and capsid positive clones selected. In the last step, the $2^{nd}$ helper plasmid (pIZ-Ar339-H) will be transfected into the previously isolated clones to generate the packaging cell line that express all three plasmids.

1.—Cloning of SP6-R Replicase into PIZ/V5-His Plasmid

In order to clone the Ar-339 replicase in PIZ/V5-His (Invitrogen, San Diego, Calif.) it is necessary to introduce a SacI RE site before the SP6 promoter.

1.1—PCR Reactions will be performed on SP6-R#406 plasmid using primers SacI_SP6F and cDNA-1R, and then the 2340 bp band will be cloned in pcr4blunt_topo vector (Invitrogen, San Diego, Calif.). The new plasmids TOPO-Rep1

Primer sequences:

```
Primer sequences:
SacI_SP6F    GGCTAGAGCTCATTTAGGTGACA (SacI)
             (SEQ ID NO: 66)

cDNA-1R      GTAACAAGATCTCGTGCCGTGACA
             (SEQ ID NO: 8)
```

1.2.—The SP6-R#406 plasmid will be digested with BglII/NotI and cloned the 5776 bp band into BglII/NotI TOPO-Rep1 to make new plasmid TOPO-Ar339-R 1.3.—The 8085 bp SacI/NotI TOPO-Ar339-R band will be cloned into SacI/NotI PIZ/V5-His to generate pIZ-Ar339-R.

2.—Cloning of Ar-339 Helper P

In order to minimize the presence of recombinant replicative competent virus, the helper genome will be split into two plasmids: PIB-Ar339-C and pIZ-Ar339-H.

2.1 Construction of pIB-Ar339-C

The Ar-339 Capsid DNA sequence will be cloned into pIB-V5-His (Invitrogen, San Diego, Calif.) at the BamHI/SpeI site of the vector. PCR will be performed on plasmid SP6-H#432 using primers C1-F and C1-R to obtain the Ar-339 capsid 1133 bp DNA band.

```
C1-F GGA TCT CCG GAT CCC CTG AAA AGG (BamHI)
     (SEQ ID NO: 67)

C1-R GTG ACC AGT GGA CTA GTG GAC CAC TCT TC (SpeI)
     (SEQ ID NO: 68)
```

The band will be digested and cloned into the pIB-V5-His vector at the BamHI/SpeI site to make the new plasmid pIB-Ar-339-C.

2.2 Construction of pIZ-Ar339-H

The first step is to clone the 5' end of Ar-339 (from nt 425 to 692) into pIZ/V5-His. PCR reactions will be performed on SP6H#432 plasmid with primers 416B-F and 676NB-R. Restriction sites will be included in this no coding sequence to allow further cloning of helper sequence.

```
416B-F
GGA TCT CCG GAT CCC CTG AAA AGG CTG T (BamHI)
(SEQ ID NO: 69)

676NB-R
GAT GAA AGG ATC CTC GCG AAC TAT TTA GGA CCA CCG
(BamHI/NruI) (SEQ ID NO: 70)
```

The 296 bp band will be digested with BamHI and cloned in the BamHI site of pIZ/V5-His to make pIZ-5END plasmid.

In a second step SP6-H#432 plasmid will be digested with NruI and XhoI and the 3435 bp band will be cloned into the NruI/XhoI site of the pIZ-5END plasmid.

REFERENCES

Bhaumik S, Gambhir S S. Optical imaging of *Renilla* luciferase reporter gene expression in living mice. Proc Natl Acad Sci USA 2002; 99:377-82.

Burge B W, Pfefferkorn E R. "Complementation between temperature-sensitive mutants of Sindbis virus". Virology. 1966 October; 30 (2):214-23.

Dubuisson J, Rice C M. "Sindbis virus attachment: isolation and characterization of mutants with impaired binding to vertebrate cells." J Virol. 1993 June; 67 (6):3363-74.

Frolova E, Frolov I, Schlesinger S. "Packaging signals in alphaviruses." J Virol. 1997 January; 71 (1):248-58.

Frothingham (1955). "Tissue culture applied to the study of Sindbis virus." Am. J. Trop. Med. Hyg. 4: 863-871.

Geigenmuller-Gnirke U, Nitschko H, Schlesinger S. "Deletion analysis of the capsid protein of Sindbis virus: identification of the RNA binding region." J Virol. 1993 March; 67 (3):1620-6.

Hurlbut, H. S. (1953). "The experimental transmission of coxsackie-like viruses by mosquitoes." J. Egypt. Med. Assoc. 36: 495-498.

Lee H, Brown D T. "Mutations in an exposed domain of Sindbis virus capsid protein result in the production of noninfectious virions and morphological variants." Virology. 1994 July; 202 (1):390-400.

Levy-Mintz P, Kielian M. "Mutagenesis of the putative fusion domain of the Semliki Forest virus spike protein." J Virol. 1991 August; 65 (8):4292-300.

Li M L, Liao H J, Simon L D, Stollar V. "An amino acid change in the exodomain of the E2 protein of Sindbis virus, which impairs the release of virus from chicken cells but not from mosquito cells." Virology. 1999 Nov. 10; 264 (1):187-94.

McKnight K L, Simpson D A, Lin S C, Knott T A, Polo J M, Pence D F, Johannsen D B, Heidner H W, Davis N L, Johnston R E. "Deduced consensus sequence of Sindbis virus strain AR339: mutations contained in laboratory strains which affect cell culture and in vivo phenotypes." J Virol. 1996 March; 70 (3):1981-9.

Myles K M, Pierro D J, Olson K E. "Deletions in the putative cell receptor-binding domain of Sindbis virus strain MRE16 E2 glycoprotein reduce midgut infectivity in *Aedes aegypti*." J Virol. 2003 August; 77 (16):8872-81.

Ohno K, Sawai K, Iijima Y, Levin B, Meruelo D. "Cell-specific targeting of Sindbis virus vectors displaying IgG-binding domains of protein A". Nat. Biotechnol. 1997 August; 15 (8):763-7.

Owen K. E. and Kuhn. R. J. "Identification of a region in the Sindbis virus nucleocapsid protein that is involved in specificity of RNA encapsidation". J. of Virology, May 1996, p 2757-2763.

Rice C M, Levis R, Strauss J H, Huang H V "Production of infectious RNA transcripts from Sindbis virus cDNA clones: mapping of lethal mutations, rescue of a temperature-sensitive marker, and in vitro mutagenesis to generate defined mutants." J Virol. 1987 December; 61 (12):3809-19.

Rikkonen M, Peranen J, Kaariainen L. "ATPase and GTPase activities associated with Semliki Forest virus nonstructural protein nsP2." J Virol. 1994 September; 68 (9):5804-10.

Rozanov M N, Koonin E V, Gorbalenya A E. "Conservation of the putative methyltransferase domain: a hallmark of the 'Sindbis-like' supergroup of positive-strand RNA viruses." J Gen Virol. 1992 August; 73 (Pt 8):2129-34.

Sammels L M, Lindsay M D, Poidinger M, Coelen R J, Mackenzie J S. "Geographic distribution and evolution of Sindbis virus in Australia." J GenVirol. 1999 March; 80 (Pt 3):739-48.

Strauss E G, Rice C M, Strauss J R. "Complete nucleotide sequence of the genomic RNA of Sindbis virus." Virology. 1984 February; 133 (1):92-110.

Strauss, J. H. and Strauss, E. G. "The alphaviruses: gene expression, replication, and evolution" Microbiol Rev. 1994 September; 58 (3): 491-562.

Taylor, R M and H S Hurlbut (1953). "Isolation of coxsackie-like viruses from mosquitoes." J. Egypt. Med. Assoc. 36: 489-494.

Taylor, R M, H S Hurlbut, T H Work, J R Kingsbury and T E Frothingham (1955). "Sindbis virus: A newly recognized arthropod-transmitted virus." Am. J. Trop. Med. Hyg. 4: 844-846.

Tseng J C, Levin B, Hirano T, Yee H, Pampeno C, Meruelo D. In vivo antitumor activity of sindbis viral vectors. J Natl Cancer Inst (Bethesda) 2002; 94:1790-802.

Tseng J C, Levin B, Hurtado A, et al. Systemic tumor targeting and killing by Sindbis viral vectors. Nat Biotechnol 2004a; 22:70-7.

Tseng J C, Hurtado A, Yee H, Levin B, Boivin C, Benet M, Blank S V, Pellicer A, Meruelo D. "Using sindbis viral vectors for specific detection and suppression of advanced ovarian cancer in animal models." Cancer Res. 2004b Sep. 15; 64 (18):6684-92.

Wang H L, O'Rear J, Stollar V. "Mutagenesis of the Sindbis virus nsP1 protein: effects on methyltransferase activity and viral infectivity." Virology. 1996 Mar. 15; 217 (2):527-31.

Weiss B, Geigenmuller-Gnirke U, Schlesinger S. "interactions between Sindbis virus RNAs and a 68 amino acid derivative of the viral capsid protein further defines the capsid binding site." Nucleic Acids Res. 1994 Mar. 11; 22 (5):780-6.

Zhang W, Mukhopadhyay S, Pletnev S V, Baker T S, Kuhn R J, Rossmann M G "Placement of the structural proteins in Sindbis virus." J Virol. 2002 November; 76 (22):11645-58.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

APPENDIX A

TABLE I

Primers used for Sindbis cDNA cloning.

| PRIMER | SEQUENCE (5'→3') | | SV NT | cDNA bp |
|---|---|---|---|---|
| cDNA-1F | ATTGACGGCGTAGTACAC | (SEQ ID NO: 7) | 1-20 | cDNA-1 |
| cDNA-1R | GTAACAAGATCTCGTGCCGTGACA (Bgl II) | (SEQ ID NO: 8) | 2299-2276 | 2276 bp |
| cDNA-2F | GGCACGAGATCTTGTTACCAGC (Bgl II) | (SEQ ID NO: 9) | 2281-2303 | cDNA-2 |
| cDNA-2R | CTTTCTTTCCTAGGCACACAGTCATTCTT (Avr II) | (SEQ ID NO: 10) | 4265-4293 | 2012 bp |
| cDNA-3F | GACTGTGTGCCTAGGAAAGAAAGTG (Avr II) | (SEQ ID NO: 11) | 4271-4295 | cDNA-3A |
| SV-6932R | CACACCCAGGTCCTCCAAGATC | (SEQ ID NO: 12) | 6932-6953 | 2682 bp |
| SV-6882F | GCATCATTCGACAAAAGCCAAG | (SEQ ID NO: 13) | 6882-6903 | cDNA-3B |
| SV-C3R | CTCTTCTAGAGGTGGTGGTGTTGTAGTATT (XbaI) | (SEQ ID NO: 14) | 7626-7656 | 774 bp |
| cDNA-4F | GGATCCCCTGAAAAGGCTGTTTAAG (BamHI) | (SEQ ID NO: 15) | 7334-7359 | cDNA-4 |
| cDNA-4R | TCATGTCTGATCAAGTCCGGTGA (BclI) | (SEQ ID NO: 16) | 9370-9348 | 2014 bp |
| cDNA-5F | GGACTTGATCAGACATGACGACCA (BclI) | (SEQ ID NO: 17) | 9353-9376 | CDNA-5 |
| cDNA-5R | TTTTTGAAATGTTAAAAACAAAATTTTGTTG | (SEQ ID NO: 18) | 11678-11703 | 2350 bp |

The restriction endonuclease recognition sites are underlined. Sindbis virus nucleotide numbers follow Strauss et al (1984) sequence (Accession# NC_001547.1)

TABLE II

| Primers used to generate vector polylinkers. | |
|---|---|
| PRIMER (RE) | SEQUENCE 5'→3' |
| Poly1-T7(+) (AflIII) | CCCACATGTGGGAGGCTAGAGTACTTAATACGACTCACTATAGGATTGACGGCGTAGTACACACTATTGAATCAAACAGCCGACC (SEQ ID NO: 19) |
| Poly1-SP6(+) (AflIII) | CCCACATGTGGGAGGCTAGAGTACATTTAGGTGACACTATAGAAATTGACGGCGTAGTACACACTATTGAATCAAACAGCCGACC (SEQ ID NO: 20) |
| Poly-2(−) (XbaI) | GGCGCGCCTCTAGACTAGCCTAGGTATGGAAGATCTTCCGCGGATCCGCCTAGTGCAATTGGTCGGCTGTTTGATTCAAT (SEQ ID NO: 21) |
| Poly-3(+) XbaI) | AGGCTAGTCTAGAGGCGCGCCGATCTCACGTGAGCATGCGTTTAAACTGGGCCCAATGTTAACATTTCAAAAAAAAAAAAAAAAA (SEQ ID NO: 22) |
| Poly-4(−) (AatII) | GGTGATGACGTCCTCGAGGCGGCCGCTTAATTAATTTAAATTTTTTTTTTTTTTTTTTTTTTTTTTTTTTTTTTTTTTTGAAATGT (SEQ ID NO: 23) |
| PCRPoly-1F (AflIII) | ATATATATCCCACATGT (SEQ ID NO: 24) |
| PCRPoly-2R | GCGCGCCTCTAGA (SEQ ID NO: 25) |
| PCRPoly-3F | AGGCTAGTCTAGAGGC (SEQ ID NO: 26) |
| PCRPoly-4R (AatII) | GGTGATGACGTCCT (SEQ ID NO: 27) |

Restriction endonuclease recognition sites (RE) are underlined. Overlapping sequences are shown in bold.

TABLE III

| PRIMERS USED IN SITE-DIRECTED MUTAGENESIS OF E2 GENE. | | |
|---|---|---|
| PRIMER | SEQUENCE 5'→3' | RE |
| E2-I3-F | GCAAAAGAAGCGTCATCGATGACTTTACCCTGACCAGC (SEQ ID NO: 28) | ClaI |
| E2-I3-R | GCTGGTCAGGGTAAAGTCATCGATGACGCTTCTTTTGC (SEQ ID NO: 29) | ClaI |
| E2-K70-F | CTACATGTCGCTTAAGCAGGATCACACCGTTAAAG (SEQ ID NO: 30) | Afl II |
| E2-K70-R | CTTTAACGGTGTGATCCTGCTTAAGCGACATGTAG (SEQ ID NO: 31) | Afl II |
| E2-E181-F | CGGGCCCGCACGCTTATACATCCTACCTGGAAGAATCATC (SEQ ID NO: 32) | Sma I |
| E2-E181-R | GATGATTCTTCCAGGTAGGATGTATAAGCGTGCGGGCCCG (SEQ ID NO: 33) | Sma I |
| E2-V251-F | GACTTGATCCGACATGACGACCACACGGTCCAAGGG (SEQ ID NO: 34) | Mme I |
| E2-V251-R | CCCTTGGACCGTGTGGTCGTCATGTCGGATCAAGTC (SEQ ID NO: 35) | Mme I |

Nucleotides changed are underlined and the new restriction sites generated are indicated (RE)

TABLE IV

Nucleotide differences between Ar-339, JT vectors and Sindbis virus Strauss sequence (Strauss et al. 1984)

| nt | Protein (a. a.) | JT | Strauss | Ar-339 | Codon Strauss → Ar339 | Codon Strauss → JT | Codon JT → Ar339 |
|---|---|---|---|---|---|---|---|
| 353 | nsP1 (98) | C | C | T | UAC(Tyr)_UAU(Tyr) | UAC(Tyr)_UAC(Tyr) | UAC(Tyr)_UAU(Tyr) |
| 1380-1 | nsP1 (441) | TG | TG | AT | UGC(Cys)_AUC(Ile) | UGC(Cys)_UGC(Cys) | UGC(Cys)_AUC(Ile) |
| 2992 | nsP2 (438) | T | C | T | CCC(Pro)_CUC(Leu) | CCC(Pro)_CUC(Leu) | CUC(Leu)_CUC(Leu) |
| 3579 | nsP2 (634) | G | A | G | AAA(Lys)_GAA(Glu) | AAA(Lys)_GAA(Glu) | GAA(Glu)_GAA(Glu) |
| 3698 | nsP2 (673) | A | G | G | AAG(Lys)_AAG(Lys) | AAA(Lys)_GAA(Glu) | GAA(Glu)_GAA(Glu) |
| 5702 | nsP3 (534) | T | A | A | CCA(Pro)_CCA(Pro) | CCA(Pro)_CCU(Pro) | CCU(Pro)_CCA(Pro) |
| 7337 | nsP4 (529) | T | T | C | GAU(Asp)_GAC(Asp) | GAU(Asp)_GAC(Asp) | GAU(Asp)_GAC(Asp) |
| 7846 | C (67) | C | C | A | CCG(Pro)_CAG(Gln) | CCG(Pro)_CCG(Pro) | CCG(Pro)_CAG(Gln) |
| 8009 | C (121) | A | G | G | GAG(Glu)_GAG(Glu) | GAG(Glu)_GAA(Glu) | GAA(Glu)_GAG(Glu) |
| 8345 | C (233) | C | C | A | GGC(Gly)_GGA(Gly) | GGC(Gly)_GGC(Gly) | GGC(Gly)_GGA(Gly) |
| 8638 | E2 (3) | T | T | C | AUU(Ile)_ACU(Thr) | AUU(Ile)_AUU(Ile) | AUU(Ile)_ACU(Thr) |
| 8698 | E2 (23) | A | T | A | GUA(Val)_GCA(Ala) | GUA(Val)_GCA(Ala) | GCA(Ala)_GCA(Ala) |
| 8838 | E2 (70) | A | A | G | AAG(Lys)_GAG(Glu) | AAG(Lys)_AAG(Lys) | AAG(Lys)_GAG(Glu) |
| 9144 | E2 (172) | G | A | G | AGA(Arg)_GGA(Gly) | AGA(Arg)→GGA(Gly) | GGA(Gly)_GGA(Gly) |
| 9171 | E2 (181) | G | G | A | GAA(Glu)_AAA(Lys) | GAA(Glu)_GAA(Glu) | GAA(Glu)_AAA(Lys) |
| 9382 | E2 (251) | T | C | C | GCC(Ala)_GCC(Ala) | GCC(Ala)_GUC(Val) | GUC(Val)_GCC(Ala) |
| 10279 | E1 (72) | C | C | T | GCU(Ala)_GUU(Val) | GCU(Ala)_GCU(Ala) | GCU(Ala)_GUU(Val) |
| 10288 | E1 (75) | G | A | A | GAC(Asp)_GAC(Asp) | GAC(Asp)_GGC(Gly) | GGC(Gly)_GAC(Asp) |
| 10392 | E1 (109) | T | T | C | UUG(Leu)_CUG(Leu) | UUG(Leu)_UUG(Leu) | UUG(Leu)_CUG(Leu) |
| 10469 | E1 (133) | T | T | A | AUU(Ile)_AUA(Ile) | AUU(Ile)_AUU(Ile) | AUU(Ile)_AUA(Ile) |
| 10773 | E1 (237) | T | T | G | UCA(Ser)_GCA(Ala) | UCA(Ser)_UCA(Ser) | UCA(Ser)_GCA(Ala) |

Nucleotide numbers follow the Strauss et al sequence. (Acession #NC_001547.1)

TABLE V

Nucleotide differences between JT vectors and Strauss sequence

| nt | Protein (a. a.) | Codon Strauss → JT | Plasmid |
|---|---|---|---|
| 2992 | nsP2 (438) | CCC(Pro)_CUC(Leu) | Replicon |
| 3579 | nsP2 (634) | AAA(Lys)_GAA(Glu) | Replicon |
| 3698 | nsP2 (673) | AAG(Lys)_AAA(Lys) | Replicon |
| 5702 | nsP3 (534) | CCA(Pro)_CCU(Pro) | Replicon |
| 7337 | nsP4 (529) | GAU(Asp)_GAC(Asp) | Replicon |
| 8009 | Capsid (121) | GAG(Glu)_GAA(Glu) | Helper |
| 8698 | E2 (23) | GUA(Val)_GCA(Ala) | Helper |
| 9144 | E2 (172) | AGA(Arg)_GGA(Gly) | Helper |
| 9382 | E2 (251) | GCC(Ala)_GUC(Val) | Helper |
| 10288 | E1 (75) | GAC(Asp)_GGC(Gly) | Helper |

Strauss et al 1984 sequence. (Accession #NC_001547.1)

TABLE VI

Summary of amino acid differences between JT and Ar-339 vectors

| nt | Protein (a. a.) | Codon JT → Ar339 | Plasmid |
|---|---|---|---|
| 13080/1381 | nsP1 (441) | UGC(Cys)_AUC(Ile) | Replicon |
| 7846 | Capsid (67) | CCG(Pro)_CAG(Gln) | Helper |
| 8638 | E2 (673) | AUU(Ile)_ACU(Thr) | Helper |
| 8838 | E2 (70) | AAG(Lys)_GAG(Glu) | Helper |
| 9171 | E2 (181) | GAA(Glu)_AAA(Lys) | Helper |
| 9382 | E2 (251) | GUC(Val)_GCC(Ala) | Helper |
| 10279 | E1 (72) | GCU(Ala)_GUU(Val) | Helper |
| 10288 | E1 (75) | GGC(Gly)_GAC(Asp) | Helper |
| 10773 | E1 (153) | UCA(Ser)_GCA(Ala) | Helper |

TABLE VII

TITER OF CHIMERIC VIRAL VECTORS.

| VIRAL VECTOR | BHK-21 cells (TU/mL) | ES-2/Fluc cells (TU/mL) | Mosec cells (TU/mL) |
|---|---|---|---|
| JT-BB/SP6-ARepLacZ | $3 \times 10^6$ | $3 \times 10^4$ | $3 \times 10^4$ |
| SP6-AH/JT-RepLacZ | $3 \times 10^4$ | $3 \times 10^3$ | $3 \times 10^3$ |
| SP6-AH/SP6-ARepLacZ | $3 \times 10^4$ | $3 \times 10^3$ | $3 \times 10^3$ |
| JT-BB/JT-RepLacZ | $3 \times 10^6$ | $3 \times 10^4$ | $3 \times 10^4$ |

Vectors were titered in BHK-21, ES-2/Fluc and Mosec cell lines. TU transducing units

TABLE VIII

TITERS OF E2 MUTANT VECTORS.

| VIRAL VECTOR | | BHK-21 (TU/mL) | ES-2/Fluc (TU/mL) | Mosec (TU/mL) |
|---|---|---|---|---|
| A | (JT-BB/SP6-RFluc) | $10^7$ | $10^5$ | $10^6$ |
| C | (SP6-H/SP6-RFluc) | $10^5$ | $10^3$ | $10^4$ |
| Mut-1 | (SP6H-K70/SP6-RFluc) | $10^4$ | $10^3$ | $10^5$ |
| Mut-2 | (SP6H-K70-V251/SP6-RFluc) | $10^5$ | $10^4$ | $10^2$ |
| Mut-4 | (SP6H-I3-K70-E181-V251/SP6-RFluc) | $10^6$ | $10^4$ | $10^5$ |

Vectors were titered in BHK-21, ES-2/Fluc and Mosec cell lines. TU transducing units

The invention claimed is:

1. An isolated nucleic acid comprising a nucleotide sequence consisting of the sequence as set forth in SEQ ID NO: 60 (T7-DM H101).

2. An isolated nucleic acid comprising a nucleotide sequence consisting of the sequence as set forth in SEQ ID NO: 65 T7-StuI-RLacZ#202.

3. A method for producing defective Sindbis virus vectors comprising the steps of
   (a) providing a linearized Replicon plasmid comprising a nucleotide sequence consisting of the sequence as set forth in SEQ ID NO: 65 and a linearized Helper plasmid comprising a nucleotide sequence consisting of the sequence as set forth in SEQ ID NO: 60;
   (b) transcribing said Replicon plasmid and said Helper plasmid to produce RNA;
   (c) collecting the RNA transcribed in step (b) from said Replicon plasmid and said Helper plasmid and transfecting cells with said RNA;
   (d) incubating said transfected cells for a time and at a temperature effective for producing defective Sindbis viral vectors; and
   (e) collecting said defective Sindbis viral vectors from the medium of said transfected cells.

* * * * *

SEQUENCE LISTING

<160> NUMBER OF SEQ ID NOS: 70

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccccaatgat ccgacca                                                    17

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaacaaatt ttgttgatta ataaaag                                         27

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
attgacggcg tagtacaca                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtatcaagta ggatccggag                                                 20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 5
ccccaatgat ccgacca                                                      17

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaaacaaaat tttgttgatt aataaaag                                          28

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
attgacggcg tagtacac                                                     18

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtaacaagat ctcgtgccgt gaca                                              24

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcacgagat cttgttacca gc                                                22

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctttctttcc taggcacaca gtcattctt                                         29

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```

```
gactgtgtgc ctaggaaaga aagtg                                          25

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cacacccagg tcctccaaga tc                                             22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcatcattcg acaaaagcca ag                                             22

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcttctaga ggtggtggtg ttgtagtatt                                     30

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggatcccctg aaaaggctgt ttaag                                          25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcatgtctga tcaagtccgg tga                                            23

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggacttgatc agacatgacg acca                                           24
```

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttttgaaat gttaaaaaca aaattttgtt g                              31

<210> SEQ ID NO 19
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cccacatgtg ggaggctaga gtacttaata cgactcacta taggattgac ggcgtagtac    60
acactattga atcaaacagc cgacc                                         85

<210> SEQ ID NO 20
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cccacatgtg ggaggctaga gtacatttag gtgacactat agaaattgac ggcgtagtac    60
acactattga atcaaacagc cgacc                                         85

<210> SEQ ID NO 21
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcgcgcctc tagactagcc taggtatgga agatcttccg cggatccgcc tagtgcaatt    60
ggtcggctgt ttgattcaat                                               80

<210> SEQ ID NO 22
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aggctagtct agaggcgcgc cgatctcacg tgagcatgcg tttaaactgg gcccaatgtt    60
aacatttcaa aaaaaaaaaa aaaaa                                         85

<210> SEQ ID NO 23
<211> LENGTH: 85
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 23
ggtgatgacg tcctcgaggc ggccgcttaa ttaatttaaa tttttttttt tttttttttt    60
tttttttttt tttttttga aatgt                                          85

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atatatatcc cacatgt                                                  17

<210> SEQ ID NO 25
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcgcgcctct aga                                                      13

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aggctagtct agaggc                                                   16

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtgatgacg tcct                                                     14

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcaaaagaag cgtcatcgat gactttaccc tgaccagc                           38

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 29
gctggtcagg gtaaagtcat cgatgacgct tcttttgc                               38

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctacatgtcg cttaagcagg atcacaccgt taaag                                  35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctttaacggt gtgatcctgc ttaagcgaca tgtag                                  35

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgggcccgca cgcttataca tcctacctgg aagaatcatc                             40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gatgattctt ccaggtagga tgtataagcg tgcgggcccg                             40

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gacttgatcc gacatgacga ccacacggtc caaggg                                 36

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 35
cccttggacc gtgtggtcgt catgtcggat caagtc        36

<210> SEQ ID NO 36
<211> LENGTH: 9928
<212> TYPE: DNA
<213> ORGANISM: Sindbis virus

<400> SEQUENCE: 36

```
attgacggcg tagtacacac tattgaatca aacagccgac caattgcact accatcacaa      60
tggagaagcc agtagtaaac gtagacgtag accccccagag tccgtttgtc gtgcaactgc    120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaaagcgtgc aagattacaa acaagaactt gcatgagaag attaaggatc    420
tccggaccgt acttgatacg ccggatgctg aaacaccatc gctctgcttt cacaacgatg    480
ttacctgcaa catgcgtgcc gaatattccg tcatgcagga cgtgtatatc aacgctcccg    540
gaactatcta tcatcaggct atgaaaggcg tgcggaccct gtactggatt ggcttcgaca    600
ccacccagtt catgttctcg gctatggcag gttcgtaccc tgcgtacaac accaactggg    660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag agcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacca   1380
tcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa aatgccaaa ctcgcaccag   1800
cgcacccgct agcagatcag gttaagatca ataacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
```

```
aggttacaaa ggcagagctt gcagaaacag agtacgtgtt tgacgtggac aagaagcgtt    2100
gcgttaagaa ggaagaagcc tcaggtctgg tcctctcggg agaactgacc aaccctccct    2160
atcatgagct agctctggag ggactgaaga cccgacctgc ggtcccgtac aaggtcgaaa    2220
caataggagt gataggcaca ccggggtcgg gcaagtcagc tattatcaag tcaactgtca    2280
cggcacgaga tcttgttacc agcggaaaga aagaaaattg tcgcgaaatt gaggccgacg    2340
tgctaagact gaggggtatg cagattacgt cgaagacagt agattcggtt atgctcaacg    2400
gatgccacaa agccgtagaa gtgctgtacg ttgacgaagc gttcgcgtgc cacgcaggag    2460
cactacttgc cttgattgct atcgtcaggc cccgcaagaa ggtagtacta tgcggagacc    2520
ccatgcaatg cggattcttc aacatgatgc aactaaaggt acatttcaat caccctgaaa    2580
aagacatatg caccaagaca ttctacaagt atatctcccg gcgttgcaca cagccagtta    2640
cagctattgt atcgacactg cattacgatg aaagatgaa aaccacgaac ccgtgcaaga    2700
agaacattga aatcgatatt acaggggcca caaagccgaa gccaggggat catcatcctga    2760 catgttccg cgggtgggtt aagcaattgc aaatcgacta tcccggacat gaagtaatga    2820
cagccgcggc ctcacaaggg ctaaccagaa aaggagtgta tgccgtccgg caaaaagtca    2880
atgaaaaccc actgtacgcg atcacatcag agcatgtgaa cgtgttgctc acccgcactg    2940
aggacaggct agtgtggaaa accttgcagg gcgacccatg gattaagcag ctcactaaca    3000
tacctaaagg aaactttcag gctactatag aggactggga agctgaacac aagggaataa    3060
ttgctgcaat aaacagcccc actccccgtg ccaatccgtt cagctgcaag accaacgttt    3120
gctgggcgaa agcattggaa ccgatactag ccacggccgg tatcgtactt accggttgcc    3180
agtggagcga actgttccca cagttttgcg atgacaaacc acattcggcc atttacgcct    3240
tagacgtaat ttgcattaag ttttttcggca tggacttgac aagcggactg ttttctaaac    3300
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg gcacacaact tgatttgcag acggggagaa    3480
ccagagttat ctctgcacag cataaacctgg tcccggtgaa ccgcaatctt cctcacgcct    3540
tagtccccga gtacaaggag aagcaacccg gcccggtcga aaaattcttg aaccagttca    3600
aacaccactc agtacttgtg gtatcagagg aaaaaattga agctccccgt aagagaatcg    3660
aatggatcgc cccgattggc atagccggtg cagataagaa ctacaacctg gctttcgggt    3720
ttccgccgca ggcacggtac gacctggtgt tcatcaacat tggaactaaa tacagaaacc    3780
accactttca gcagtgcgaa gaccatgcgg cgaccttaaa aacccttttcg cgttcggccc    3840 tgaattgcct taacccagga ggcacccctcg tggtgaagtc ctatggctac gccgaccgca    3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcacccccg caccatctga attgcgtgat ttcgtccgtg tatgagggta    4080
caagagatgg agttggagcc gcgccgtcat accgcaccaa aagggagaat attgctgact    4140
gtcaagagga agcagttgtc aacgcagcca atccgctggg tagaccaggc aaggagtct    4200 gccgtgccat ctataaacgt tggccgacca gttttaccga ttcagccacg gagacaggca    4260
ccgcaagaat gactgtgtgc ctaggaaaga aagtgatcca cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
```

-continued

| | |
|---|---|
| acgcagccgg aaaagaccgc cttgaagtat cacttaactg cttgacaacc gcgctagaca | 4500 |
| gaactgacgc ggacgtaacc atctattgcc tggataagaa gtggaaggaa agaatcgacg | 4560 |
| cggcactcca acttaaggag tctgtaacag agctgaagga tgaagatatg gagatcgacg | 4620 |
| atgagttagt atggatccat ccagacagtt gcttgaaggg aagaaaggga ttcagtacta | 4680 |
| caaaaggaaa attgtattcg tacttcgaag gcaccaaatt ccatcaagca gcaaaagaca | 4740 |
| tggcggagat aaaggtcctg ttccctaatg accaggaaag taatgaacaa ctgtgtgcct | 4800 |
| acatattggg tgagaccatg gaagcaatcc gcgaaaagtg cccggtcgac cataacccgt | 4860 |
| cgtctagccc gcccaaaacg ttgccgtgcc tttgcatgta tgccatgacg ccagaaaggg | 4920 |
| tccacagact tagaagcaat aacgtcaaag aagttacagt atgctcctcc acccccttc | 4980 |
| ctaagcacaa aattaagaat gttcagaagg ttcagtgcac gaaagtagtc ctgtttaatc | 5040 |
| cgcacactcc cgcattcgtt cccgcccgta agtacataga agtgccagaa cagcctaccg | 5100 |
| ctcctcctgc acaggccgag gaggccccg aagttgtagc gacaccgtca ccatctacag | 5160 |
| ctgataacac ctcgcttgat gtcacagaca tctcactgga tatggatgac agtagcgaag | 5220 |
| gctcactttt ttcgagcttt agcggatcgg acaactctat tactagtatg gacagttggt | 5280 |
| cgtcaggacc tagttcacta gagatagtag accgaaggca ggtggtggtg gctgacgttc | 5340 |
| atgccgtcca agagcctgcc cctattccac cgccaaggct aaagaagatg gcccgcctgg | 5400 |
| cagcggcaag aaaagagccc actccaccgg caagcaatag ctctgagtcc ctccacctct | 5460 |
| cttttggtgg ggtatccatg tccctcggat caattttcga cggagagacg gcccgccagg | 5520 |
| cagcggtaca accctggca acaggcccca cggatgtgcc tatgtctttc ggatcgtttt | 5580 |
| ccgacggaga gattgatgag ctgagccgca gagtaactga gtccgaaccc gtcctgtttg | 5640 |
| gatcatttga accgggcgaa gtgaactcaa ttatatcgtc ccgatcagcc gtatcttttc | 5700 |
| cactacgcaa gcagagacgt agacgcagga gcaggaggac tgaatactga ctaaccgggg | 5760 |
| taggtgggta catattttcg acggacacag gccctgggca cttgcaaaag aagtccgttc | 5820 |
| tgcagaacca gcttacagaa ccgaccttgg agcgcaatgt cctggaaaga attcatgccc | 5880 |
| cggtgctcga cacgtcgaaa gaggaacaac tcaaactcag gtaccagatg atgcccaccg | 5940 |
| aagccaacaa aagtaggtac cagtctcgta aagtagaaaa tcagaaagcc ataaccactg | 6000 |
| agcgactact gtcaggacta cgactgtata actctgccac agatcagcca gaatgctata | 6060 |
| agatcaccta tccgaaacca ttgtactcca gtagcgtacc ggcgaactac tccgatccac | 6120 |
| agttcgctgt agctgtctgt aacaactatc tgcatgagaa ctatccgaca gtagcatctt | 6180 |
| atcagattac tgacgagtac gatgcttact tggatatggt agacgggaca gtcgcctgcc | 6240 |
| tggatactgc aaccttctgc cccgctaagc ttagaagtta cccgaaaaaa catgagtata | 6300 |
| gagccccgaa tatccgcagt gcggttccat cagcgatgca gaacacgcta caaaatgtgc | 6360 |
| tcattgccgc aactaaaaga aattgcaacg tcacgcagat gcgtgaactg ccaacactgg | 6420 |
| actcagcgac attcaatgtc gaatgctttc gaaaatatgc atgtaatgac gagtattggg | 6480 |
| aggagttcgc tcggaagcca attaggatta ccactgagtt tgtcaccgca tatgtagcta | 6540 |
| gactgaaagg ccctaaggcc gccgcactat ttgcaaagac gtataatttg gtcccattgc | 6600 |
| aagaagtgcc tatggataga ttcgtcatgg acatgaaaag agacgtgaaa gttacaccag | 6660 |
| gcacgaaaca cacagaagaa agaccgaaag tacaagtgat acaagccgca gaacccctgg | 6720 |
| cgactgctta cttatgcggg attcaccggg aattagtgcg taggcttacg gccgtcttgc | 6780 |
| ttccaaacat tcacacgctt tttgacatgt cggcggagga ttttgatgca atcatagcag | 6840 |

```
aacacttcaa gcaaggcgac ccggtactgg agacggatat cgcatcattc gacaaaagcc    6900
aagacgacgc tatggcgtta accggtctga tgatcttgga ggacctgggt gtggatcaac    6960
cactactcga cttgatcgag tgcgcctttg gagaaatatc atccacccat ctacctacgg    7020
gtactcgttt taaattcggg gcgatgatga atccggaat gttcctcaca ctttttgtca     7080
acacagtttt gaatgtcgtt atcgccagca gagtactaga gagcggctt aaaacgtcca    7140 gatgtgcagc gttcattggc gacgacaaca tcatacatgg agtagtatct gacaaagaaa    7200
tggctgagag gtgcgccacc tggctcaaca tggaggttaa gatcatcgac gcagtcatcg    7260
gtgagagacc accttacttc tgcggcggat ttatcttgca agattcggtt acttccacag    7320
cgtgccgcgt ggcggacccc ctgaaaaggc tgtttaagtt gggtaaaccg ctcccagccg    7380
acgacgagca agacgaagac agaagacgcg ctctgctaga tgaaacaaag gcgtggttta    7440
gagtaggtat aacaggcact ttagcagtgg ccgtgacgac ccggtatgag gtagacaata    7500
ttacacctgt cctactggca ttgagaactt ttgcccagag caaaagagca ttccaagcca    7560 tcaggggga aataaagcat ctctacggtg gtcctaaata gtcagcatag tacatttcat     7620
ctgactaata ctacaacacc accacctcta gaggcgcgcc gatctcacgt gagcatgcgt    7680
ttaaactggg cccaatgttc cccaatgatc cgaccagcaa aactcgatgt acttccgagg    7740
aactgatgtg cataatgcat caggctggta cattagatcc ccgcttaccg cgggcaatat    7800
agcaacacta aaaactcgat gtacttccga ggaagcgcag tgcataatgc tgcgcagtgt    7860
tgccacataa ccactatatt aaccatttat ctagcggacg ccaaaaactc aatgtatttc    7920
tgaggaagcg tggtgcataa tgccacgcag cgtctgcata acttttatta tttctttat    7980 taatcaacaa aattttgttt ttaacatttc aaaaaaaaaa aaaaaaaaaa aaaaaaaaa    8040 aaaaaaaatt taaattaatt aagcggccgc ctcgaggacg tcaggtggca cttttcgggg    8100
aaatgtgcgc ggaacccta tttgtttatt tttctaaata cattcaaata tgtatccgct    8160
catgagacaa taaccctgat aaatgcttca ataatattga aaaaggaaga gtatgagtat    8220
tcaacatttc cgtgtcgccc ttattccctt ttttgcggca ttttgccttc ctgttttgc    8280 tcacccagaa acgctggtga agtaaaaga tgctgaagat cagttgggtg cacgagtggg    8340
ttacatcgaa ctggatctca acagcggtaa gatccttgag agttttcgcc ccgaagaacg    8400
ttttccaatg atgagcactt ttaaagttct gctatgtggc gcggtattat cccgtattga    8460
cgccgggcaa gagcaactcg gtcgccgcat acactattct cagaatgact tggttgagta    8520
ctcaccagtc acagaaaagc atcttacgga tggcatgaca gtaagagaat tatgcagtgc    8580
tgccataacc atgagtgata acactgcggc caacttactt ctgacaacga tcggaggacc    8640
gaaggagcta accgcttttt tgcacaacat ggggatcat gtaactcgcc ttgatcgttg     8700
ggaaccggag ctgaatgaag ccataccaaa cgacgagcgt gacaccacga tgcctgtagc    8760
aatggcaaca acgttgcgca aactattaac tggcgaacta cttactctag cttcccggca    8820
acaattaata gactggatgg aggcggataa agttgcagga ccacttctgc gctcggccct    8880
tccggctggc tggtttattg ctgataaatc tggagccggt gagcgtgggt ctcgcggtat    8940
cattgcagca ctggggccag atggtaagcc ctcccgtatc gtagttatct acacgacggg    9000
gagtcaggca actatggatg aacgaaatag acagatcgct gagataggtg cctcactgat    9060
taagcattgg taactgtcag accaagttta ctcatatata ctttagattg atttaaaact    9120 tcattttaa tttaaaagga tctaggtgaa gatcctttt gataatctca tgaccaaaat     9180
cccttaacgt gagttttcgt tccactgagc gtcagacccc gtagaaaaga tcaaaggatc    9240
```

```
ttcttgagat cctttttttc tgcgcgtaat ctgctgcttg caaacaaaaa aaccaccgct    9300
accagcggtg gtttgtttgc cggatcaaga gctaccaact cttttccga  aggtaactgg    9360
cttcagcaga gcgcagatac caaatactgg tcttctagtg tagccgtagt taggccacca    9420
cttcaagaac tctgtagcac cgcctacata cctcgctctg ctaatcctgt taccagtggc    9480
tgctgccagt ggcgataagt cgtgtcttac cgggttggac tcaagacgat agttaccgga    9540
taaggcgcag cggtcgggct gaacggggggg ttcgtgcaca cagcccagct tggagcgaac    9600
gacctacacc gaactgagat acctacagcg tgagctatga gaaagcgcca cgcttcccga    9660
agggagaaag gcggacaggt atccggtaag cggcagggtc ggaacaggag agcgcacgag    9720
ggagcttcca gggggaaacg cctggtatct ttatagtcct gtcgggtttc gccacctctg    9780
acttgagcgt cgatttttgt gatgctcgtc aggggggcgg agcctatgga aaaacgccag    9840
caacgcggcc ttttacggt  tcctggcctt tgctggcct  tttgctcaca tgtgggaggc    9900
tagagtacat ttaggtgaca ctatagaa                                       9928

<210> SEQ ID NO 37
<211> LENGTH: 6711
<212> TYPE: DNA
<213> ORGANISM: Sindbis virus

<400> SEQUENCE: 37
attgacggcg tagtacacac tattgaatca aacagccgac caattgcact accatcacaa      60
tggagaagcc agtagtaaac gtagacgtag accccccagag tccgtttgtc gtgcaactgc    120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaaagcgtgc aagattacaa acaagaactt gcatgagaag attaaggatc    420
tccggatccc ctgaaaaggc tgtttaagtt gggtaaaccg ctcccagccg acgacgagca    480
agacgaagac agaagacgcg ctctgctaga tgaaacaaag gcgtggttta gagtaggtat    540
aacaggcact ttagcagtgg ccgtgacgac ccggtatgag gtagacaata ttacacctgt    600
cctactggca ttgagaactt tgcccagag  caaaagagca ttccaagcca tcagagggga    660
aataaagcat ctctacggtg gtcctaaata gtcagcatag tacatttcat ctgactaata    720
ctacaacacc accaccatga atagaggatt ctttaacatg ctcggccgcc gccccttccc    780
ggccccccact gccatgtgga ggccgcggag aaggaggcag gcggccccga tgcctgcccg    840
caacgggctg gcttctcaaa tccagcaact gaccacagcc gtcagtgccc tagtcattgg    900
acaggcaact agacctcaac ccccacgtcc acgccagcca ccgcgccaga agaagcaggc    960
gcccaagcaa ccaccgaagc cgaagaaacc aaaaacgcag gagaagaaga gaagcaacc   1020
tgcaaaaccc aaacccggaa agagacagcg catggcactt aagttggagg ccgacagatt   1080
gttcgacgtc aagaacgagg acggagatgt catcgggcac gcactggcca tggaaggaaa   1140
ggtaatgaaa cctctgcacg tgaaaggaac catcgaccac cctgtgctat caaagctcaa   1200
atttaccaag tcgtcagcat acgacatgga gttcgcacag ttgccagtca acatgagaag   1260
tgaggcattc acctacacca gtgaacaccc cgaaggattc tataactggc accacggagc   1320
ggtgcagtat agtggaggta gatttaccat ccctcgcgga gtaggaggca gaggagacag   1380
cggtcgtccg atcatggata actccggtcg ggttgtcgcg atagtcctcg gtggagctga   1440
```

-continued

```
tgaaggaaca cgaactgccc tttcggtcgt cacctggaat agtaaaggga agacaattaa    1500
gacgaccccg gaagggacag aagagtggtc cgcagcacca ctggtcacgg caatgtgttt    1560
gctcggaaat gtgagcttcc catgcgaccg cccgcccaca tgctataccc gcgaaccttc    1620
cagagccctc gacatccttg aagagaacgt gaaccatgag gcctacgata ccctgctcaa    1680
tgccatattg cggtgcggat cgtctggcag aagcaaaaga agcgtcactg acgactttac    1740
cctgaccagc ccctacttgg gcacatgctc gtactgccac catactgaac cgtgcttcag    1800
ccctgttaag atcgagcagg tctgggacga agcggacgat aacaccatac gcatacagac    1860
ttccgcccag tttggatacg accaaagcgg agcagcaagc gcaaacaagt accgctacat    1920
gtcgcttgag caggatcaca ccgttaaaga aggcaccatg gatgacatca agattagcac    1980
ctcaggaccg tgtagaaggc ttagctacaa aggatacttt ctcctcgcaa aatgccctcc    2040
aggggacagc gtaacggtta gcatagtgag tagcaactca gcaacgtcat gtacactggc    2100
ccgcaagata aaaccaaaat tcgtgggacg ggaaaaatat gatctacctc ccgttcacgg    2160
taaaaaaatt ccttgcacag tgtacgaccg tctgaaagaa acaactgcag gctacatcac    2220
tatgcacagg ccgggaccgc acgcttatac atcctacctg aaagaatcat cagggaaagt    2280
ttacgcaaag ccgccatctg ggaagaacat tacgtatgag tgcaagtgcg gcgactacaa    2340
gaccggaacc gtttcgaccc gcaccgaaat cactggttgc accgccatca agcagtgcgt    2400
cgcctataag agcgaccaaa cgaagtgggt cttcaactca ccggacttga tcagacatga    2460
cgaccacacg gcccaaggga aattgcattt gcctttcaag ttgatcccga gtacctgcat    2520
ggtccctgtt gcccacgcgc cgaatgtaat acatggcttt aaacacatca gcctccaatt    2580
agatacagac cacttgacat tgctcaccac caggagacta ggggcaaaacc cggaaccaac    2640
cactgaatgg atcgtcggaa agacggtcag aaacttcacc gtcgaccgag atggcctgga    2700
atacatatgg ggaaatcatg agccagtgag ggtctatgcc caagagtcag caccaggaga    2760
ccctcacgga tggccacacg aaatagtaca gcattactac catcgccatc ctgtgtacac    2820
catcttagcc gtcgcatcag ctaccgtggc gatgatgatt ggcgtaactg ttgcagtgtt    2880
atgtgcctgt aaagcgcgcc gtgagtgcct gacgccatac gccctggccc caaacgccgt    2940
aatcccaact tcgctggcac tcttgtgctg cgttaggtcg gccaatgctg aaacgttcac    3000
cgagaccatg agttacttgt ggtcgaacag tcagccgttc ttctgggtcc agttgtgcat    3060
acctttggcc gctttcatcg ttctaatgcg ctgctgctcc tgctgcctgc ctttttagt    3120
ggttgccggc gcctacctgg cgaaggtaga cgcctacgaa catgcgacca ctgttccaaa    3180
tgtgccacag ataccgtata aggcacttgt tgaaagggca gggtatgccc cgctcaattt    3240
ggagatcact gtcatgtcct cggaggtttt gccttccacc aaccaagagt acattacctg    3300
caaattcacc actgtggtcc cctccccaaa aatcaaatgc tgcggctcct tggaatgtca    3360
gccgccgtt catgcagact ataccctgcaa ggtcttcgga ggggtctacc cctttatgtg    3420
gggaggagcg caatgttttt gcgacagtga aacagccag atgagtgagg cgtacgtcga    3480
actgtcagca gattgcgcgt ctgaccacgc gcaggcgatt aaggtgcaca ctgccgcgat    3540
gaaagtagga ctgcgtatag tgtacgggaa cactaccagt ttcctagatg tgtacgtgaa    3600
cggagtcaca ccaggaacgt ctaaagactt gaaagtcata gctggaccaa tttcagcatc    3660
gttacgcca ttcgatcata aggtcgttat ccatcgcggc ctggtgtaca actatgactt    3720
cccggaatat ggagcgatga aaccaggagc gtttggagac attcaagcta cctccttgac    3780
tagcaaggat ctcatcgcca gcacagacat taggctactc aagccttccg ccaagaacgt    3840
```

```
gcatgtcccg tacacgcagg ccgcatcagg atttgagatg tggaaaaaca actcaggccg    3900
cccactgcag gaaaccgcac ctttcgggtg taagattgca gtaaatccgc tccgagcggt    3960
ggactgttca tacgggaaca ttcccatttc tattgacatc ccgaacgctg cctttatcag    4020
gacatcagat gcaccactgg tctcaacagt caaatgtgaa gtcagtgagt gcacttattc    4080
agcagacttc ggcgggatgg ccaccctgca gtatgtatcc gaccgcgaag gtcaatgccc    4140
cgtacattcg cattcgagca cagcaactct ccaagagtcg acagtacatg tcctggagaa    4200
aggagcggtg acagtacact ttagcaccgc gagtccacag gcgaacttta tcgtatcgct    4260
gtgtgggaag aagacaacat gcaatgcaga atgtaaacca ccagctgacc atatcgtgag    4320
caccccgcac aaaaatgacc aagaatttca agccgccatc tcaaaaacat catggagttg    4380
gctgtttgcc cttttcggcg gcgcctcgtc gctattaatt ataggactta tgattttgc     4440 ttgcagcatg atgctgacta gcacacgaag atgaccgcta cgccccaatg atccgaccag    4500
caaaactcga tgtacttccg aggaactgat gtgcataatg catcaggctg gtacattaga    4560
tccccgctta ccgcgggcaa tatagcaaca ctaaaaactc gatgtacttc cgaggaagcg    4620
cagtgcataa tgctgcgcag tgttgccaca taaccactat attaaccatt tatctagcgg    4680
acgccaaaaa ctcaatgtat ttctgaggaa gcgtggtgca taatgccacg cagcgtctgc    4740
ataactttta ttatttcttt tattaatcaa caaaattttg ttttttaacat ttcaaaaaaa    4800 aaaaaaaaa aaaaaaaaaa aaaaaaaaa atttaaatta attaagcggc cgcctcgagg     4860
acgtcaggtg gcacttttcg gggaaatgtg cgcggaaccc ctatttgttt attttttctaa   4920 atacattcaa atatgtatcc gctcatgaga caataaccct gataaatgct tcaataatat    4980
tgaaaaagga gagtatgag tattcaacat ttccgtgtcg cccttattcc cttttttgcg     5040
gcattttgcc ttcctgtttt tgctcaccca gaaacgctgg tgaaagtaaa agatgctgaa    5100
gatcagttgg gtgcacgagt gggttacatc gaactggatc tcaacagcgg taagatcctt    5160
gagagttttc gccccgaaga acgttttcca atgatgagca cttttaaagt tctgctatgt    5220
ggcgcggtat tatcccgtat tgacgccggg caagagcaac tcggtcgccg catacactat    5280
tctcagaatg acttggttga gtactcacca gtcacagaaa agcatcttac ggatggcatg    5340
acagtaagag aattatgcag tgctgccata accatgagtg ataacactgc ggccaactta    5400
cttctgacaa cgatcggagg accgaaggag ctaaccgctt ttttgcacaa catgggggat    5460
catgtaactc gccttgatcg ttgggaaccg gagctgaatg aagccatacc aaacgacgag    5520
cgtgacacca cgatgcctgt agcaatggca acaacgttgc gcaaactatt aactggcgaa    5580
ctacttactc tagcttcccg gcaacaatta atagactgga tggaggcgga taaagttgca    5640
ggaccacttc tgcgctcggc ccttccggct ggctggttta ttgctgataa atctggagcc    5700
ggtgagcgtg ggtctcgcgg tatcattgca gcactggggc cagatggtaa gccctcccgt    5760
atcgtagtta tctacacgac ggggagtcag gcaactatgg atgaacgaaa tagacagatc    5820
gctgagatag gtgcctcact gattaagcat tggtaactgt cagaccaagt ttactcatat    5880
atactttaga ttgatttaaa acttcatttt taatttaaaa ggatctaggt gaagatcctt    5940
tttgataatc tcatgaccaa aatcccttaa cgtgagtttt cgttccactg agcgtcagac    6000
cccgtagaaa agatcaaagg atcttcttga gatccttttt ttctgcgcgt aatctgctgc    6060
ttgcaaacaa aaaaaccacc gctaccagcg gtggtttgtt tgccggatca agagctacca    6120
actctttttc cgaaggtaac tggcttcagc agagcgcaga taccaaatac tgtccttcta    6180
gtgtagccgt agttaggcca ccacttcaag aactctgtag caccgcctac atacctcgct    6240
```

```
ctgctaatcc tgttaccagt ggctgctgcc agtggcgata agtcgtgtct taccgggttg    6300
gactcaagac gatagttacc ggataaggcg cagcggtcgg gctgaacggg gggttcgtgc    6360
acacagccca gcttggagcg aacgacctac accgaactga gatacctaca gcgtgagcta    6420
tgagaaagcg ccacgcttcc cgaagggaga aaggcggaca ggtatccggt aagcggcagg    6480
gtcggaacag gagagcgcac gagggagctt ccaggggaaa acgcctggta tctttatagt    6540
cctgtcgggt ttcgccacct ctgacttgag cgtcgatttt tgtgatgctc gtcaggggg    6600 cggagcctat ggaaaaacgc cagcaacgcg gccttttta cggttcctggc cttttgctgg    6660 ccttttgctc acatgtggga ggctagagta catttaggtg acactataga a             6711

<210> SEQ ID NO 38
<211> LENGTH: 6711
<212> TYPE: DNA
<213> ORGANISM: Sindbis virus

<400> SEQUENCE: 38
attgacggcg tagtacacac tattgaatca aacagccgac caattgcact accatcacaa      60
tggagaagcc agtagtaaac gtagacgtag accccagag tccgtttgtc gtgcaactgc     120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaaagcgtgc aagattacaa acaagaactt gcatgagaag attaaggatc    420
tccggatccc ctgaaaaggc tgtttaagtt gggtaaaccg ctcccagccg acgacgagca    480
agacgaagac agaagacgcg ctctgctaga tgaaacaaag gcgtggttta gagtaggtat    540
aacaggcact ttagcagtgg ccgtgacgac ccggtatgag gtagacaata ttacacctgt    600
cctactggca ttgagaactt ttgcccagag caaaagagca ttccaagcca tcagagggga    660
aataaagcat ctctacggtg gtcctaaata gtcagcatag tacatttcat ctgactaata    720
ctacaacacc accaccatga atagaggatt cttaacatg ctcggccgcc gcccttccc     780 ggccccact gccatgtgga ggccgcggag aaggaggcag gcggccccga tgcctgcccg    840
caacgggctg gcttctcaaa tccagcaact gaccacagcc gtcagtgccc tagtcattgg    900
acaggcaact agacctcaac ccccacgtcc acgccagcca ccgcgccaga agaagcaggc    960
gcccaagcaa ccaccgaagc cgaagaaacc aaaaacgcag gagaagaaga agaagcaacc   1020
tgcaaaaccc aaacccggaa agagacagcg catggcactt aagttggagg ccgacagatt   1080
gttcgacgtc aagaacgagg acggagatgt catcgggcac gcactggcca tggaaggaaa   1140
ggtaatgaaa cctctgcacg tgaaaggaac catcgaccac cctgtgctat caaagctcaa   1200
atttaccaag tcgtcagcat acgacatgga gttcgcacag ttgccagtca acatgagaag   1260
tgaggcattc acctacacca gtgaacaccc cgaaggattc tataactggc accacggagc   1320
ggtgcagtat agtggaggta gatttaccat ccctcgcgga gtaggaggca gaggagacag   1380
cggtcgtccg atcatggata actccggtcg ggttgtcgcg atagtcctcg gtggagctga   1440
tgaaggaaca cgaactgccc tttcggtcgt cacctggaat agtaaaggga agacaattaa   1500 gacgacccg gaagggacag aagagtggtc cgcagcacca ctggtcacgg caatgtgttt   1560
gctcggaaat gtgagcttcc catgcgaccg cccgcccaca tgctatccc gcgaaccttc   1620 cagagccctc gacatccttg aagagaacgt gaaccatgag gcctacgata ccctgctcaa   1680
```

-continued

```
tgccatattg cggtgcggat cgtctggcag aagcaaaaga agcgtcactg acgactttac    1740
cctgaccagc ccctacttgg gcacatgctc gtactgccac catactgaac cgtgcttcag    1800
ccctgttaag atcgagcagg tctgggacga agcggacgat aacaccatac gcatacagac    1860
ttccgcccag tttggatacg accaaagcgg agcagcaagc gcaaacaagt accgctacat    1920
gtcgcttaag caggatcaca ccgttaaaga aggcaccatg gatgacatca agattagcac    1980
ctcaggaccg tgtagaaggc ttagctacaa aggatacttt ctcctcgcaa aatgccctcc    2040
aggggacagc gtaacggtta gcatagtgag tagcaactca gcaacgtcat gtacactggc    2100
ccgcaagata aaaccaaaat tcgtgggacg ggaaaaatat gatctacctc ccgttcacgg    2160
taaaaaaatt ccttgcacag tgtacgaccg tctgaaagaa caactgcag gctacatcac     2220
tatgcacagg ccgggaccgc acgcttatac atcctacctg aaagaatcat cagggaaagt    2280
ttacgcaaag ccgccatctg ggaagaacat tacgtatgag tgcaagtgcg gcgactacaa    2340
gaccggaacc gtttcgaccc gcaccgaaat cactggttgc accgccatca agcagtgcgt    2400
cgcctataag agcgaccaaa cgaagtgggt cttcaactca ccggacttga tcagacatga    2460
cgaccacacg gcccaaggga aattgcattt gcctttcaag ttgatcccga gtacctgcat    2520
ggtccctgtt gcccacgcgc cgaatgtaat acatggcttt aaacacatca gcctccaatt    2580
agatacagac cacttgacat tgctcaccac caggagacta ggggcaaacc cggaaccaac    2640
cactgaatgg atcgtcggaa agacggtcag aaacttcacc gtcgaccgag atggcctgga    2700
atacatatgg ggaaatcatg agccagtgag ggtctatgcc caagagtcag caccaggaga    2760
ccctcacgga tggccacacg aaatagtaca gcattactac catcgccatc ctgtgtacac    2820
catcttagcc gtcgcatcag ctaccgtggc gatgatgatt ggcgtaactg ttgcagtgtt    2880
atgtgcctgt aaagcgcgcc gtgagtgcct gacgccatac gccctggccc aaacgccgt    2940
aatcccaact tcgctggcac tcttgtgctg cgttaggtcg gccaatgctg aaacgttcac    3000
cgagaccatg agttacttgt ggtcgaacag tcagccgttc ttctgggtcc agttgtgcat    3060
accttTggcc gctttcatcg ttctaatgcg ctgctgctcc tgctgcctgc cttttttagt    3120
ggttgccggc gcctacctgg cgaaggtaga cgcctacgaa catgcgacca ctgttccaaa    3180
tgtgccacag ataccgtata aggcacttgt tgaaagggca gggtatgccc cgctcaattt    3240
ggagatcact gtcatgtcct cggaggtttt gccttccacc aaccaagagt acattacctg    3300
caaattcacc actgtggtcc cctccccaaa aatcaaatgc tgcggctcct tggaatgtca    3360
gccgccgtt catgcagact ataccctgcaa ggtcttcgga ggggtctacc cctttatgtg    3420
gggaggagcg caatgttttt gcgacagtga aacagccag atgagtgagg cgtacgtcga    3480
actgtcagca gattgcgcgt ctgaccacgc gcaggcgatt aaggtgcaca ctgccgcgat    3540
gaaagtagga ctgcgtatag tgtacgggaa cactaccagt ttcctagatg tgtacgtgaa    3600
cggagtcaca ccaggaacgt ctaaagactt gaaagtcata gctggaccaa tttcagcatc    3660
gtttacgcca ttcgatcata aggtcgttat ccatcgcggc ctggtgtaca actatgactt    3720
cccggaatat ggagcgatga aaccaggagc gtttggagac attcaagcta cctccttgac    3780
tagcaaggat ctcatcgcca gcacagacat taggctactc aagccttccg ccaagaacgt    3840
gcatgtcccg tacacgcagg ccgcatcagg atttgagatg tggaaaaaca actcaggccg    3900
cccactgcag gaaaccgcac ctttcgggtg taagattgca gtaaatccgc tccgagcggt    3960
ggactgttca tacgggaaca ttcccatttc tattgacatc ccgaacgctg cctttatcag    4020
gacatcagat gcaccactgg tctcaacagt caaatgtgaa gtcagtgagt gcacttattc    4080
```

```
agcagacttc ggcgggatgg ccaccctgca gtatgtatcc gaccgcgaag gtcaatgccc    4140
cgtacattcg cattcgagca cagcaactct ccaagagtcg acagtacatg tcctggagaa    4200
aggagcggtg acagtacact ttagcaccgc gagtccacag gcgaacttta tcgtatcgct    4260
gtgtgggaag aagacaacat gcaatgcaga atgtaaacca ccagctgacc atatcgtgag    4320
caccccgcac aaaaatgacc aagaatttca agccgccatc tcaaaaacat catggagttg    4380
gctgtttgcc cttttcggcg gcgcctcgtc gctattaatt ataggactta tgattttgc     4440
ttgcagcatg atgctgacta gcacacgaag atgaccgcta cgccccaatg atccgaccag    4500
caaaactcga tgtacttccg aggaactgat gtgcataatg catcaggctg gtacattaga    4560
tccccgctta ccgcgggcaa tatagcaaca ctaaaaactc gatgtacttc cgaggaagcg    4620
cagtgcataa tgctgcgcag tgttgccaca taaccactat attaaccatt tatctagcgg    4680
acgccaaaaa ctcaatgtat ttctgaggaa gcgtggtgca taatgccacg cagcgtctgc    4740
ataactttta ttatttcttt tattaatcaa caaaattttg ttttaacat ttcaaaaaaa     4800
aaaaaaaaa aaaaaaaaa aaaaaaaaa atttaaatta attaagcggc cgcctcgagg       4860
acgtcaggtg gcacttttcg gggaaatgtg cgcggaaccc ctatttgttt attttttctaa   4920
atacattcaa atatgtatcc gctcatgaga caataaccct gataaatgct tcaataatat    4980
tgaaaaagga agagtatgag tattcaacat ttccgtgtcg cccttattcc cttttttgcg    5040
gcattttgcc ttcctgtttt tgctcaccca gaaacgctgg tgaaagtaaa agatgctgaa    5100
gatcagttgg gtgcacgagt gggttacatc gaactggatc tcaacagcgg taagatcctt    5160
gagagttttc gccccgaaga acgttttcca atgatgagca cttttaaagt tctgctatgt    5220
ggcgcggtat tatcccgtat tgacgccggg caagagcaac tcggtcgccg catacactat    5280
tctcagaatg acttggttga gtactcacca gtcacagaaa agcatcttac ggatggcatg    5340
acagtaagag aattatgcag tgctgccata accatgagtg ataacactgc ggccaactta    5400
cttctgacaa cgatcggagg accgaaggag ctaaccgctt ttttgcacaa catgggggat    5460
catgtaactc gccttgatcg ttgggaaccg gagctgaatg aagccatacc aaacgacgag    5520
cgtgacacca cgatgcctgt agcaatggca acaacgttgc gcaaactatt aactggcgaa    5580
ctacttactc tagcttcccg gcaacaatta atagactgga tggaggcgga taaagttgca    5640
ggaccacttc tgcgctcggc ccttccggct ggctggttta ttgctgataa atctggagcc    5700
ggtgagcgtg ggtctcgcgg tatcattgca gcactggggc cagatggtaa gccctcccgt    5760
atcgtagtta tctacacgac ggggagtcag gcaactatgg atgaacgaaa tagacagatc    5820
gctgagatag gtgcctcact gattaagcat tggtaactgt cagaccaagt ttactcatat    5880
atactttaga ttgatttaaa acttcatttt taatttaaaa ggatctaggt gaagatcctt    5940
tttgataatc tcatgaccaa aatcccttaa cgtgagtttt cgttccactg agcgtcagac    6000
cccgtagaaa agatcaaagg atcttcttga gatcctttt ttctgcgcgt aatctgctgc     6060
ttgcaaacaa aaaaaccacc gctaccagcg gtggtttgtt tgccggatca agagctacca    6120
actctttttc cgaaggtaac tggcttcagc agagcgcaga taccaaatac tgtccttcta    6180
gtgtagccgt agttaggcca ccacttcaag aactctgtag caccgcctac atacctcgct    6240
ctgctaatcc tgttaccagt ggctgctgcc agtggcgata gtcgtgtct taccgggttg     6300
gactcaagac gatagttacc ggataaggcg cagcggtcgg gctgaacggg gggttcgtgc    6360
acacagccca gcttggagcg aacgacctac accgaactga gatacctaca gcgtgagcta    6420
tgagaaagcg ccacgcttcc cgaagggaga aaggcggaca ggtatccggt aagcggcagg    6480
```

```
gtcggaacag gagagcgcac gagggagctt ccagggggaa acgcctggta tctttatagt    6540
cctgtcgggt ttcgccacct ctgacttgag cgtcgatttt tgtgatgctc gtcagggggg    6600
cggagcctat ggaaaaacgc cagcaacgcg gccttttttac ggttcctggc cttttgctgg    6660 cctttttgctc acatgtggga ggctagagta catttaggtg acactataga a            6711

<210> SEQ ID NO 39
<211> LENGTH: 6711
<212> TYPE: DNA
<213> ORGANISM: Sindbis virus

<400> SEQUENCE: 39
attgacggcg tagtacacac tattgaatca aacagccgac caattgcact accatcacaa      60
tggagaagcc agtagtaaac gtagacgtag accccccagag tccgtttgtc gtgcaactgc    120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaaagcgtgc aagattacaa acaagaactt gcatgagaag attaaggatc    420
tccggatccc ctgaaaaggc tgtttaagtt gggtaaaccg ctcccagccg acgacgagca    480
agacgaagac agaagacgcg ctctgctaga tgaaacaaag gcgtggttta gagtaggtat    540
aacaggcact ttagcagtgg ccgtgacgac ccggtatgag gtagacaata ttacacctgt    600
cctactggca ttgagaactt tgcccagag caaaagagca ttccaagcca tcagagggga    660
aataaagcat ctctacggtg gtcctaaata gtcagcatag tacatttcat ctgactaata    720
ctacaacacc accaccatga atagaggatt ctttaacatg ctcggccgcc gccccttccc    780 ggccccact gccatgtgga ggccgcggag aaggaggcag gcggcccga tgcctgcccg    840 caacgggctg gcttctcaaa tccagcaact gaccacagcc gtcagtgccc tagtcattgg    900
acaggcaact agacctcaac ccccacgtcc acgccagcca ccgcgccaga gaagcaggc    960 gcccaagcaa ccaccgaagc cgaagaaacc aaaaacgcag gagaagaaga agaagcaacc   1020
tgcaaaaccc aaacccggaa agagacagcg catggcactt aagttggagg ccgacagatt   1080
gttcgacgtc aagaacgagg acggagatgt catcgggcac gcactggcca tggaaggaaa   1140
ggtaatgaaa cctctgcacg tgaaaggaac catcgaccac cctgtgctat caaagctcaa   1200
atttaccaag tcgtcagcat acgacatgga gttcgcacag ttgccagtca acatgagaag   1260
tgaggcattc acctacacca gtgaacaccc cgaaggattc tataactggc accacggagc   1320
ggtgcagtat agtggaggta gatttaccat ccctcgcgga gtaggaggca gaggagacag   1380
cggtcgtccg atcatggata actccggtcg ggttgtcgcg atagtcctcg gtggagctga   1440
tgaaggaaca cgaactgccc tttcggtcgt cacctggaat agtaaaggga agacaattaa   1500
gacgaccccg gaagggacag aagagtggtc cgcagcacca ctggtcacgg caatgtgttt   1560
gctcggaaat gtgagcttcc catgcgaccg cccgcccaca tgctataccc gcgaaccttc   1620
cagagccctc gacatccttg aagagaacgt gaaccatgag gcctacgata ccctgctcaa   1680
tgccatattg cggtgcggat cgtctggcag aagcaaaaga agcgtcatcg atgactttac   1740
cctgaccagc ccctacttgg gcacatgctc gtactgccac catactgaac cgtgcttcag   1800
ccctgttaag atcgagcagg tctgggacga agcggacgat aacaccatac gcatacagac   1860
ttccgcccag tttggatacg accaaagcgg agcagcaagc gcaaacaagt accgctacat   1920
```

```
gtcgcttaag caggatcaca ccgttaaaga aggcaccatg gatgacatca agattagcac   1980
ctcaggaccg tgtagaaggc ttagctacaa aggatacttt ctcctcgcaa aatgccctcc   2040
aggggacagc gtaacggtta gcatagtgag tagcaactca gcaacgtcat gtacactggc   2100
ccgcaagata aaaccaaaat tcgtgggacg ggaaaaatat gatctacctc ccgttcacgg   2160
taaaaaaatt ccttgcacag tgtacgaccg tctgaaagaa acaactgcag gctacatcac   2220
tatgcacagg ccgggcccgc acgcttatac atcctacctg gaagaatcat cagggaaagt   2280
ttacgcaaag ccgccatctg ggaagaacat tacgtatgag tgcaagtgcg gcgactacaa   2340
gaccggaacc gtttcgaccc gcaccgaaat cactggttgc accgccatca agcagtgcgt   2400
cgcctataag agcgaccaaa cgaagtgggt cttcaactca ccggacttga tccgacatga   2460
cgaccacacg gtccaaggga aattgcattt gcctttcaag ttgatcccga gtacctgcat   2520
ggtccctgtt gcccacgcgc cgaatgtaat acatggcttt aaacacatca gcctccaatt   2580
agatacagac cacttgacat tgctcaccac caggagacta ggggcaaacc cggaaccaac   2640
cactgaatgg atcgtcggaa agacggtcag aaacttcacc gtcgaccgag atggcctgga   2700
atacatatgg ggaaatcatg agccagtgag ggtctatgcc caagagtcag caccaggaga   2760
ccctcacgga tggccacacg aaatagtaca gcattactac catcgccatc ctgtgtacac   2820
catcttagcc gtcgcatcag ctaccgtggc gatgatgatt ggcgtaactg ttgcagtgtt   2880
atgtgcctgt aaagcgcgcc gtgagtgcct gacgccatac gccctggccc aaaacgccgt   2940
aatcccaact tcgctggcac tcttgtgctg cgttaggtcg gccaatgctg aaacgttcac   3000
cgagaccatg agttacttgt ggtcgaacag tcagccgttc ttctgggtcc agttgtgcat   3060
acctttggcc gctttcatcg ttctaatgcg ctgctgctcc tgctgcctgc ctttttttagt   3120 ggttgccggc gcctacctgg cgaaggtaga cgcctacgaa catgcgacca ctgttccaaa   3180
tgtgccacag ataccgtata aggcacttgt tgaaagggca gggtatgccc cgctcaattt   3240
ggagatcact gtcatgtcct cggaggtttt gcccttccacc aaccaagagt acattacctg   3300
caaattcacc actgtggtcc cctccccaaa aatcaaatgc tgcggctcct tggaatgtca   3360
gccggccgtt catgcagact ataccctgca ggtcttcgga ggggtctacc cctttatgtg   3420
gggaggagcg caatgttttt gcgacagtga aacagccag atgagtgagg cgtacgtcga   3480
actgtcagca gattgcgcgt ctgaccacgc gcaggcgatt aaggtgcaca ctgccgcgat   3540
gaaagtagga ctgcgtatag tgtacgggaa cactaccagt ttcctagatg tgtacgtgaa   3600
cggagtcaca ccaggaacgt ctaaagactt gaaagtcata gctggaccaa tttcagcatc   3660
gtttacgcca ttcgatcata aggtcgttat ccatcgcggc ctggtgtaca actatgactt   3720
cccggaatat ggagcgatga accaggagc gtttggagac attcaagcta cctccttgac   3780
tagcaaggat ctcatcgcca gcacagacat taggctactc aagccttccg ccaagaacgt   3840
gcatgtcccg tacacgcagg ccgcatcagg atttgagatg tggaaaaaca actcaggccg   3900
cccactgcag gaaaccgcac ctttcgggtg taagattgca gtaaatccgc tccgagcggt   3960
ggactgttca tacgggaaca ttcccattc tattgacatc ccgaacgctg cctttatcag   4020
gacatcagat gcaccactgg tctcaacagt caaatgtgaa gtcagtgagt gcacttattc   4080
agcagacttc ggcgggatgg ccaccctgca gtatgtatcc gaccgcgaag gtcaatgccc   4140
cgtacattcg cattcgagca cagcaactct ccaagagtcg acagtacatg tcctggagaa   4200
aggagcggtg acagtacact ttagcaccgc gagtccacag gcgaacttta tcgtatcgct   4260
gtgtgggaag aagacaacat gcaatgcaga atgtaaacca ccagctgacc atatcgtgag   4320
```

```
caccccgcac aaaaatgacc aagaatttca agccgccatc tcaaaaacat catggagttg    4380
gctgtttgcc cttttcggcg gcgcctcgtc gctattaatt ataggactta tgattttttgc   4440 ttgcagcatg atgctgacta gcacacgaag atgaccgcta cgccccaatg atccgaccag    4500
caaaactcga tgtacttccg aggaactgat gtgcataatg catcaggctg gtacattaga    4560
tccccgctta ccgcgggcaa tatagcaaca ctaaaaactc gatgtacttc cgaggaagcg    4620
cagtgcataa tgctgcgcag tgttgccaca taaccactat attaaccatt tatctagcgg    4680
acgccaaaaa ctcaatgtat ttctgaggaa gcgtggtgca taatgccacg cagcgtctgc    4740
ataactttta ttatttcttt tattaatcaa caaaattttg tttttaacat ttcaaaaaaa    4800
aaaaaaaaaa aaaaaaaaaa aaaaaaaaaa atttaaatta attaagcggc cgcctcgagg    4860
acgtcaggtg gcacttttcg gggaaatgtg cgcggaaccc ctatttgttt attttttctaa   4920 atacattcaa atatgtatcc gctcatgaga caataaccct gataaatgct tcaataatat    4980
tgaaaaagga gagtatgag tattcaacat ttccgtgtcg cccttattcc cttttttgcg     5040
gcattttgcc ttcctgtttt tgctcaccca gaaacgctgg tgaaagtaaa agatgctgaa    5100
gatcagttgg gtgcacgagt gggttacatc gaactggatc tcaacagcgg taagatcctt    5160
gagagttttc gccccgaaga acgttttcca atgatgagca cttttaaagt tctgctatgt    5220
ggcgcggtat tatcccgtat tgacgccggg caagagcaac tcggtcgccg catacactat    5280
tctcagaatg acttggttga gtactcacca gtcacagaaa agcatcttac ggatggcatg    5340
acagtaagag aattatgcag tgctgccata accatgagtg ataacactgc ggccaactta    5400
cttctgacaa cgatcggagg accgaaggag ctaaccgctt ttttgcacaa catgggggat    5460
catgtaactc gccttgatcg ttgggaaccg gagctgaatg aagccatacc aaacgacgag    5520
cgtgacacca cgatgcctgt agcaatggca acaacgttgc gcaaactatt aactggcgaa    5580
ctacttactc tagcttcccg gcaacaatta atagactgga tggaggcgga taaagttgca    5640
ggaccacttc tgcgctcggc ccttccggct ggctggttta ttgctgataa atctggagcc    5700
ggtgagcgtg ggtctcgcgg tatcattgca gcactggggc cagatggtaa gccctcccgt    5760
atcgtagtta tctacacgac ggggagtcag gcaactatgg atgaacgaaa tagacagatc    5820
gctgagatag gtgcctcact gattaagcat tggtaactgt cagaccaagt ttactcatat    5880
atactttaga ttgatttaaa acttcatttt taatttaaaa ggatctaggt gaagatcctt    5940
tttgataatc tcatgaccaa aatcccttaa cgtgagtttt cgttccactg agcgtcagac    6000
cccgtagaaa agatcaaagg atcttcttga gatcctttt tctgcgcgt aatctgctgc      6060 ttgcaaacaa aaaaccacc gctaccagcg gtggtttgtt tgccggatca agagctacca    6120
actctttttc cgaaggtaac tggcttcagc agagcgcaga taccaaatac tgtccttcta    6180
gtgtagccgt agttaggcca ccacttcaag aactctgtag caccgcctac atacctcgct    6240
ctgctaatcc tgttaccagt ggctgctgcc agtggcgata gtcgtgtct taccgggttg     6300 gactcaagac gatagttacc ggataaggcg cagcggtcgg gctgaacggg gggttcgtgc    6360
acacagccca gcttggagcg aacgacctac accgaactga gatacctaca gcgtgagcta    6420
tgagaaagcg ccacgcttcc cgaagggaga aaggcggaca ggtatccggt aagcggcagg    6480
gtcggaacag gagagcgcac gagggagctt ccagggggaa acgcctggta tctttatagt    6540
cctgtcgggt ttcgccacct ctgacttgag cgtcgatttt tgtgatgctc gtcagggggg    6600
cggagcctat ggaaaaacgc cagcaacgcg gcctttttac ggttcctggc cttttgctgg    6660
ccttttgctc acatgtggga ggctagagta catttaggtg acactataga a             6711
```

<210> SEQ ID NO 40
<211> LENGTH: 6711
<212> TYPE: DNA
<213> ORGANISM: Sindbis virus

<400> SEQUENCE: 40

```
attgacggcg tagtacacac tattgaatca aacagccgac caattgcact accatcacaa      60
tggagaagcc agtagtaaac gtagacgtag acccccagag tccgtttgtc gtgcaactgc     120
aaaaaagctt cccgcaattt gaggtagtag cacagcaggt cactccaaat gaccatgcta     180
atgccagagc attttcgcat ctggccagta aactaatcga gctggaggtt cctaccacag     240
cgacgatctt ggacataggc agcgcaccgg ctcgtagaat gttttccgag caccagtatc     300
attgtgtctg ccccatgcgt agtccagaag acccggaccg catgatgaaa tatgccagta     360
aactggcgga aaaagcgtgc aagattacaa acaagaactt gcatgagaag attaaggatc     420
tccggatccc ctgaaaaggc tgtttaagtt gggtaaaccg ctcccagccg acgacgagca     480
agacgaagac agaagacgcg ctctgctaga tgaaacaaag gcgtggttta gagtaggtat     540
aacaggcact ttagcagtgg ccgtgacgac ccggtatgag gtagacaata ttacacctgt     600
cctactggca ttgagaactt ttgcccagag caaaagagca ttccaagcca tcagagggga     660
aataaagcat ctctacggtg gtcctaaata gtcagcatag tacatttcat ctgactaata     720
ctacaacacc accaccatga atagaggatt ctttaacatg ctcggccgcc gccccttccc     780
ggcccccact gccatgtgga ggccgcggag aaggaggcag gcggccccga tgcctgcccg     840
caacgggctg gcttctcaaa tccagcaact gaccacagcc gtcagtgccc tagtcattgg     900
acaggcaact agacctcaac ccccacgtcc acgccagcca ccgcgccaga agaagcaggc     960
gcccaagcaa ccaccgaagc cgaagaaacc aaaaacgcag gagaagaaga agaagcaacc    1020
tgcaaaaccc aaacccggaa agagacagcg catggcactt aagttggagg ccgacagatt    1080
gttcgacgtc aagaacgagg acggagatgt catcgggcac gcactggcca tggaaggaaa    1140
ggtaatgaaa cctctgcacg tgaaaggaac catcgaccac cctgtgctat caaagctcaa    1200
atttaccaag tcgtcagcat acgacatgga gttcgcacag ttgccagtca acatgagaag    1260
tgaggcattc acctacacca gtgaacaccc cgaaggattc tataactggc accacggagc    1320
ggtgcagtat agtggaggta gatttaccat ccctcgcgga gtaggaggca gaggagacag    1380
cggtcgtccg atcatggata actccggtcg ggttgtcgcg atagtcctcg gtggagctga    1440
tgaaggaaca cgaactgccc tttcggtcgt cacctggaat agtaaaggga agacaattaa    1500
gacgaccccg gaagggacag aagagtggtc cgcagcacca ctggtcacgg caatgtgttt    1560
gctcggaaat gtgagcttcc catgcgaccg cccgcccaca tgctataccc gcgaaccttc    1620
cagagccctc gacatccttg aagagaacgt gaaccatgag gcctacgata ccctgctcaa    1680
tgccatattg cggtgcggat cgtctggcag aagcaaaaga agcgtcactg acgactttac    1740
cctgaccagc ccctacttgg gcacatgctc gtactgccac catactgaac cgtgcttcag    1800
ccctgttaag atcgagcagg tctgggacga agcggacgat aacaccatac gcatacagac    1860
ttccgcccag tttggatacg accaaagcgg agcagcaagc gcaaacaagt accgctacat    1920
gtcgcttaag caggatcaca ccgttaaaga aggcaccatg gatgacatca agattagcac    1980
ctcaggaccg tgtagaaggc ttagctacaa aggatacttt ctcctcgcaa aatgccctcc    2040
aggggacagc gtaacggtta gcatagtgag tagcaactca gcaacgtcat gtacactggc    2100
ccgcaagata aaaccaaaat tcgtgggacg ggaaaaatat gatctacctc ccgttcacgg    2160
```

```
taaaaaaatt ccttgcacag tgtacgaccg tctgaaagaa acaactgcag gctacatcac    2220
tatgcacagg ccgggaccgc acgcttatac atcctacctg aaagaatcat cagggaaagt    2280
ttacgcaaag ccgccatctg ggaagaacat tacgtatgag tgcaagtgcg gcgactacaa    2340
gaccggaacc gtttcgaccc gcaccgaaat cactggttgc accgccatca agcagtgcgt    2400
cgcctataag agcgaccaaa cgaagtgggt cttcaactca ccggacttga tccgacatga    2460
cgaccacacg gtccaaggga aattgcattt gcctttcaag ttgatcccga gtacctgcat    2520
ggtccctgtt gcccacgcgc cgaatgtaat acatggcttt aaacacatca gcctccaatt    2580
agatacagac cacttgacat tgctcaccac caggagacta ggggcaaacc cggaaccaac    2640
cactgaatgg atcgtcggaa agacggtcag aaacttcacc gtcgaccgag atggcctgga    2700
atacatatgg ggaaatcatg agccagtgag ggtctatgcc caagagtcag caccaggaga    2760
ccctcacgga tggccacacg aaatagtaca gcattactac catcgccatc ctgtgtacac    2820
catcttagcc gtcgcatcag ctaccgtggc gatgatgatt ggcgtaactg ttgcagtgtt    2880
atgtgcctgt aaagcgcgcc gtgagtgcct gacgccatac gccctggccc aaacgccgt     2940 aatcccaact tcgctggcac tcttgtgctg cgttaggtcg gccaatgctg aaacgttcac    3000
cgagaccatg agttacttgt ggtcgaacag tcagccgttc ttctgggtcc agttgtgcat    3060 accttttggcc gctttcatcg ttctaatgcg ctgctgctcc tgctgcctgc cttttttagt    3120
ggttgccggc gcctacctgg cgaaggtaga cgcctacgaa catgcgacca ctgttccaaa    3180
tgtgccacag ataccgtata aggcacttgt tgaaagggca gggtatgccc cgctcaattt    3240
ggagatcact gtcatgtcct cggaggtttt gccttccacc aaccaagagt acattacctg    3300
caaattcacc actgtggtcc cctccccaaa aatcaaatgc tgcggctcct tggaatgtca    3360
gccggccgtt catgcagact atacctgcaa ggtcttcgga ggggtctacc cctttatgtg    3420
gggaggagcg caatgttttt gcgacagtga aacagccag atgagtgagg cgtacgtcga    3480
actgtcagca gattgcgcgt ctgaccacgc gcaggcgatt aaggtgcaca ctgccgcgat    3540
gaaagtagga ctgcgtatag tgtacgggaa cactaccagt ttcctagatg tgtacgtgaa    3600
cggagtcaca ccaggaacgt ctaaagactt gaaagtcata gctggaccaa tttcagcatc    3660
gtttacgcca ttcgatcata aggtcgttat ccatcgcggc ctggtgtaca actatgactt    3720
cccggaatat ggagcgatga aaccaggagc gtttggagac attcaagcta cctccttgac    3780
tagcaaggat ctcatcgcca gcacagacat taggctactc aagccttccg ccaagaacgt    3840
gcatgtcccg tacacgcagg ccgcatcagg atttgagatg tggaaaaaca actcaggccg    3900
cccactgcag gaaaccgcac ctttcgggtg taagattgca gtaaatccgc tccgagcggt    3960
ggactgttca tacgggaaca ttcccatttc tattgacatc ccgaacgctg cctttatcag    4020
gacatcagat gcaccactgg tctcaacagt caaatgtgaa gtcagtgagt gcacttattc    4080
agcagacttc ggcgggatgg ccaccctgca gtatgtatcc gaccgcgaag gtcaatgccc    4140
cgtacattcg cattcgagca cagcaactct ccaagagtcg acagtacatg tcctggagaa    4200
aggagcggtg acagtacact ttagcaccgc gagtccacag gcgaacttta tcgtatcgct    4260
gtgtgggaag aagacaacat gcaatgcaga atgtaaacca ccagctgacc atatcgtgag    4320 cacccccgcac aaaatgacc aagaatttca agccgccatc tcaaaaacat catggagttg    4380
gctgtttgcc cttttcggcg gcgcctcgtc gctattaatt ataggactta tgattttttgc    4440 ttgcagcatg atgctgacta gcacacgaag atgaccgcta cgcccaatg atccgaccag    4500 caaaactcga tgtacttccg aggaactgat gtgcataatg catcaggctg gtacattaga    4560
```

```
tccccgctta ccgcgggcaa tatagcaaca ctaaaaactc gatgtacttc cgaggaagcg    4620
cagtgcataa tgctgcgcag tgttgccaca taaccactat attaaccatt tatctagcgg    4680
acgccaaaaa ctcaatgtat ttctgaggaa gcgtggtgca taatgccacg cagcgtctgc    4740
ataactttta ttatttcttt tattaatcaa caaaattttg tttttaacat ttcaaaaaaa    4800
aaaaaaaaaa aaaaaaaaaa aaaaaaaaa atttaaatta attaagcggc cgcctcgagg    4860
acgtcaggtg gcacttttcg gggaaatgtg cgcggaaccc ctatttgttt attttttctaa    4920 atacattcaa atatgtatcc gctcatgaga caataaccct gataaatgct tcaataatat    4980
tgaaaaagga gagtatgag tattcaacat ttccgtgtcg cccttattcc ctttttttgcg    5040 gcattttgcc ttcctgtttt tgctcaccca gaaacgctgg tgaaagtaaa agatgctgaa    5100
gatcagttgg gtgcacgagt gggttacatc gaactggatc tcaacagcgg taagatcctt    5160
gagagttttc gccccgaaga acgttttcca atgatgagca cttttaaagt tctgctatgt    5220
ggcgcggtat tatcccgtat tgacgccggg caagagcaac tcggtcgccg catacactat    5280
tctcagaatg acttggttga gtactcacca gtcacagaaa agcatcttac ggatggcatg    5340
acagtaagag aattatgcag tgctgccata accatgagtg ataacactgc ggccaactta    5400
cttctgacaa cgatcggagg accgaaggag ctaaccgctt ttttgcacaa catgggggat    5460
catgtaactc gccttgatcg ttgggaaccg gagctgaatg aagccatacc aaacgacgag    5520
cgtgacacca cgatgcctgt agcaatggca acaacgttgc gcaaactatt aactggcgaa    5580
ctacttactc tagcttcccg gcaacaatta atagactgga tggaggcgga taaagttgca    5640
ggaccacttc tgcgctcggc ccttccggct ggctggttta ttgctgataa atctggagcc    5700
ggtgagcgtg ggtctcgcgg tatcattgca gcactgggc cagatggtaa gccctcccgt    5760
atcgtagtta tctacacgac ggggagtcag gcaactatgg atgaacgaaa tagacagatc    5820
gctgagatag gtgcctcact gattaagcat tggtaactgt cagaccaagt ttactcatat    5880
atactttaga ttgatttaaa acttcatttt taatttaaaa ggatctaggt gaagatcctt    5940
tttgataatc tcatgaccaa aatcccttaa cgtgagtttt cgttccactg agcgtcagac    6000
cccgtagaaa agatcaaagg atcttcttga tcctttttt tctgcgcgt aatctgctgc    6060 ttgcaaacaa aaaaaccacc gctaccagcg gtggtttgtt tgccggatca agagctacca    6120
actctttttc cgaaggtaac tggcttcagc agagcgcaga taccaaatac tgtccttcta    6180
gtgtagccgt agttaggcca ccacttcaag aactctgtag caccgcctac atacctcgct    6240
ctgctaatcc tgttaccagt ggctgctgcc agtggcgata gtcgtgtct taccgggttg    6300 gactcaagac gatagttacc ggataaggcg cagcggtcgg gctgaacggg gggttcgtgc    6360
acacagccca gcttggagcg aacgacctac accgaactga gatacctaca gcgtgagcta    6420
tgagaaagcg ccacgcttcc cgaagggaga aaggcggaca ggtatccggt aagcggcagg    6480
gtcggaacag gagagcgcac gagggagctt ccagggggaa acgcctggta tctttatagt    6540
cctgtcgggt ttcgccacct ctgacttgag cgtcgatttt tgtgatgctc gtcagggggg    6600
cggagcctat ggaaaaacgc cagcaacgcg gcctttttac ggttcctggc cttttgctgg    6660
ccttttgctc acatgtggga ggctagagta catttaggtg acactataga a              6711
```

<210> SEQ ID NO 41
<211> LENGTH: 6746
<212> TYPE: DNA
<213> ORGANISM: Artificial Sequence
<220> FEATURE:
<223> OTHER INFORMATION: Description of Artificial Sequence: Synthetic polynucleotide

```
<400> SEQUENCE: 41
ggatatagtg gtgagtatcc ccgcctgtca tgcgggagac cggggttcgg ttccccgacg      60
gggagccaaa cagccgacca attgcactac catcacaatg gagaagccag tagtaaacgt     120
agacgtagac ccccagagtc cgtttgtcgt gcaactgcaa aaaagcttcc cgcaatttga     180
ggtagtagca cagcaggtca ctccaaatga ccatgctaat gccagagcat tttcgcatct     240
ggccagtaaa ctaatcgagc tggaggttcc taccacagcg acgatcttgg acataggcag     300
cgcaccggct cgtagaatgt tttccgagca ccagtatcat tgtgtctgcc ccatgcgtag     360
tccagaagac ccggaccgca tgatgaaata tgccagtaaa ctggcggaaa aagcgtgcaa     420
gattacaaac aagaacttgc atgagaagat taaggatctc cggatcccct gaaaaggctg     480
tttaagttgg gtaaaccgct cccagccgac gacgagcaag acgaagacag aagacgcgct     540
ctgctagatg aaacaaaggc gtggtttaga gtaggtataa caggcacttt agcagtggcc     600
gtgacgaccc ggtatgaggt agacaatatt acacctgtcc tactggcatt gagaactttt     660
gcccagagca aaagagcatt ccaagccatc agagggaaa taaagcatct ctacggtggt      720
cctaaatagt cagcatagta catttcatct gactaatact acaacaccac caccatgaat     780
agaggattct ttaacatgct cggccgccgc cccttcccgg cccccactgc catgtggagg     840
ccgcggagaa ggaggcaggc ggccccgatg cctgcccgca acgggctggc ttctcaaatc     900
cagcaactga ccacagccgt cagtgcccta gtcattggac aggcaactag acctcaaccc     960
ccacgtccac gccagccacc cgccagaag aagcaggcgc ccaagcaacc accgaagccg    1020
aagaaaccaa aaacgcagga gaagaagaag aagcaacctg caaaacccaa acccggaaag    1080
agacagcgca tggcacttaa gttggaggcc gacagattgt tcgacgtcaa gaacgaggac    1140
ggagatgtca tcgggcacgc actggccatg gaaggaaagg taatgaaacc tctgcacgtg    1200
aaaggaacca tcgaccaccc tgtgctatca agctcaaat ttaccaagtc gtcagcatac     1260
gacatggagt tcgcacagtt gccagtcaac atgagaagtg aggcattcac ctacaccagt    1320
gaacaccccg aaggattcta taactggcac cacgagcgg tgcagtatag tggaggtaga     1380
tttaccatcc ctcgcggagt aggaggcaga ggagacagcg gtcgtccgat catggataac    1440
tccggtcggg ttgtcgcgat agtcctcggt ggagctgatg aaggaacacg aactgccctt    1500
tcggtcgtca cctggaatag taaagggaag acaattaaga cgaccccgga agggacagaa    1560
gagtggtccg cagcaccact ggtcacggca atgtgtttgc tcggaaatgt gagcttccca    1620
tgcgaccgcc cgcccacatg ctatacccgc gaaccttcca gagccctcga catccttgaa    1680
gagaacgtga accatgaggc ctacgatacc ctgctcaatg ccatattgcg gtgcggatcg    1740
tctggcagaa gcaaaagaag cgtcatcgat gactttaccc tgaccagccc ctacttgggc    1800
acatgctcgt actgccacca tactgaaccg tgcttcagcc ctgttaagat cgagcaggtc    1860
tgggacgaag cggacgataa caccatacgc atacagactt ccgcccagtt tggatacgac    1920
caaagcggag cagcaagcgc aaacaagtac cgctacatgt cgcttaagca ggatcacacc    1980
gttaaagaag gcaccatgga tgacatcaag attagcacct caggaccgtg tagaaggctt    2040
agctacaaag gatactttct cctcgcaaaa tgccctccag gggacagcgt aacggttagc    2100
atagtgagta gcaactcagc aacgtcatgt acactggccc gcaagataaa ccaaaattc    2160 gtgggacggg aaaaatatga tctacctccc gttcacggta aaaaaattcc ttgcacagtg    2220
tacgaccgtc tgaaagaaac aactgcaggc tacatcacta tgcacaggcc gggcccgcac    2280
gcttatacat cctacctgga agaatcatca gggaaagttt acgcaaagcc gccatctggg    2340
```

```
aagaacatta cgtatgagtg caagtgcggc gactacaaga ccggaaccgt ttcgacccgc   2400
accgaaatca ctggttgcac cgccatcaag cagtgcgtcg cctataagag cgaccaaacg   2460
aagtgggtct tcaactcacc ggacttgatc cgacatgacg accacacggt ccaagggaaa   2520
ttgcatttgc ctttcaagtt gatcccgagt acctgcatgg tccctgttgc ccacgcgccg   2580
aatgtaatac atggctttaa acacatcagc ctccaattag atacagacca cttgacattg   2640
ctcaccacca ggagactagg ggcaaacccg gaaccaacca ctgaatggat cgtcggaaag   2700
acggtcagaa acttcaccgt cgaccgagat ggcctggaat acatatgggg aaatcatgag   2760
ccagtgaggg tctatgccca agagtcagca ccaggagacc ctcacggatg ccacacgaa    2820 atagtacagc attactacca tcgccatcct gtgtacacca tcttagccgt cgcatcagct   2880
accgtggcga tgatgattgg cgtaactgtt gcagtgttat gtgcctgtaa agcgcgccgt   2940
gagtgcctga cgccatacgc cctggcccca aacgccgtaa tcccaacttc gctggcactc   3000
ttgtgctgcg ttaggtcggc caatgctgaa acgttcaccg agaccatgag ttacttgtgg   3060
tcgaacagtc agccgttctt ctgggtccag ttgtgcatac cttggccgc tttcatcgtt    3120 ctaatgcgct gctgctcctg ctgcctgcct tttttagtgg ttgccggcgc ctacctggcg   3180
aaggtagacg cctacgaaca tgcgaccact gttccaaatg tgccacagat accgtataag   3240
gcacttgttg aaagggcagg gtatgccccg ctcaatttgg agatcactgt catgtcctcg   3300
gaggttttgc cttccaccaa ccaagagtac attacctgca aattcaccac tgtggtcccc   3360
tccccaaaaa tcaatgctg cggctccttg gaatgtcagc cggccgcgca tgcagggtat    3420
acctgcaagg tcttcggagg ggtctacccc tttatgtggg gaggagcgca atgttttgc    3480 gacagtgaga cagccagat gagtgaggcg tacgtcgaac tgtcagcaga ttgcgcgtct    3540
gaccacgcgc aggcgattaa ggtgcacact gccgcgatga agtaggact gcgtatagtg    3600 tacgggaaca ctaccagttt cctagatgtg tacgtgaacg gagtcacacc aggaacgtct   3660
aaagacttga aagtcatagc tggaccaatt tcagcatcgt ttacgccatt cgatcataag   3720
gtcgttatcc atcgcggcct ggtgtacaac tatgacttcc cggaatatgg agcgatgaaa   3780
ccaggagcgt ttggagacat tcaagctacc tccttgacta gcaaggatct catcgccagc   3840
acagacatta ggctactcaa gccttccgcc aagaacgtgc atgtcccgta cacgcaggcc   3900
tcttcaggat ttgagatgtg gaaaaacaac tcaggccgcc cactgcagga aaccgcacct   3960
ttcgggtgta agattgcagt aaatccgctc cgagcggtgg actgttcata cgggaacatt   4020
cccatttcta ttgacatccc gaacgctgcc tttatcagga catcagatgc accactggtc   4080
tcaacagtca aatgtgaagt cagtgagtgc acttattcag cagacttcgg cgggatggcc   4140
accctgcagt atgtatccga ccgcgaaggt caatgccccg tacattcgca ttcgagcaca   4200
gcaactctcc aagagtcgac agtacatgtc ctggagaaag gagcggtgac agtacacttt   4260
agcaccgcga gtccacaggc gaactttatc gtatcgctgt gtgggaagaa gacaacatgc   4320
aatgcagaat gtaaaccacc agctgaccat atcgtgagca ccccgcacaa aaatgaccaa   4380
gaatttcaag ccgccatctc aaaaacatca tggagttggc tgtttgccct tttcggcggc   4440
gcctcgtcgc tattaattat aggacttatg attttttgctt gcagcatgat gctgactagc   4500
acacgaagat gaccgctacg ccccaatgat ccgaccagca aaactcgatg tacttccgag   4560
gaactgatgt gcataatgca tcaggctggt acattagatc cccgcttacc gcgggcaata   4620
tagcaacact aaaaactcga tgtacttccg aggaagcgca gtgcataatg ctgcgcagtg   4680
ttgccacata accactatat taaccattta tctagcggac gccaaaaact caatgtattt   4740
```

```
ctgaggaagc gtggtgcata atgccacgca gcgtctgcat aacttttatt atttctttta    4800
ttaatcaaca aaattttgtt tttaacattt caaaaaaaaa aaaaaaaaaa aaaaaaaaaa    4860
aaaaaaaaat ttaaattaat taagcggccg cctcgaggac gtcaggtggc acttttcggg    4920
gaaatgtgcg cggaacccct atttgtttat ttttctaaat acattcaaat atgtatccgc    4980
tcatgagaca ataaccctga taaatgcttc aataatattg aaaaggaag agtatgagta    5040 ttcaacattt ccgtgtcgcc cttattccct tttttgcggc attttgcctt cctgtttttg    5100
ctcacccaga aacgctggtg aaagtaaaag atgctgaaga tcagttgggt gcacgagtgg    5160
gttacatcga actggatctc aacagcggta agatccttga gagttttcgc cccgaagaac    5220
gttttccaat gatgagcact tttaaagttc tgctatgtgg cgcggtatta tcccgtattg    5280
acgccgggca agagcaactc ggtcgccgca tacactattc tcagaatgac ttggttgagt    5340
actcaccagt cacagaaaag catcttacgg atggcatgac agtaagagaa ttatgcagtg    5400
ctgccataac catgagtgat aacactgcgg ccaacttact tctgacaacg atcggaggac    5460
cgaaggagct aaccgctttt ttgcacaaca tgggggatca tgtaactcgc cttgatcgtt    5520
gggaaccgga gctgaatgaa gccataccaa acgacgagcg tgacaccacg atgcctgtag    5580
caatggcaac aacgttgcgc aaactattaa ctggcgaact acttactcta gcttcccggc    5640
aacaattaat agactggatg gaggcggata agttgcagg accacttctg cgctcggccc    5700
ttccggctgg ctggtttatt gctgataaat ctggagccgg tgagcgtggg tctcgcggta    5760
tcattgcagc actggggcca gatggtaagc cctcccgtat cgtagttatc tacacgacgg    5820
ggagtcaggc aactatggat gaacgaaata gacagatcgc tgagataggt gcctcactga    5880
ttaagcattg gtaactgtca gaccaagttt actcatatat actttagatt gatttaaaac    5940 ttcatttta atttaaaagg atctaggtga agatccttt tgataatctc atgaccaaaa    6000
tcccttaacg tgagttttcg ttccactgag cgtcagaccc cgtagaaaag atcaaaggat    6060
cttcttgaga tccttttttt ctgcgcgtaa tctgctgctt gcaaacaaaa aaaccaccgc    6120
taccagcggt ggtttgtttg ccggatcaag agctaccaac tcttttccg aaggtaactg    6180 gcttcagcag agcgcagata ccaaatactg tccttctagt gtagccgtag ttaggccacc    6240
acttcaagaa ctctgtagca ccgcctacat acctcgctct gctaatcctg ttaccagtgg    6300
ctgctgccag tggcgataag tcgtgtctta ccgggttgga ctcaagacga tagttaccgg    6360
ataaggcgca gcggtcgggc tgaacggggg gttcgtgcac acagcccagc ttggagcgaa    6420
cgacctacac cgaactgaga tacctacagc gtgagctatg agaaagcgcc acgcttcccg    6480
aagggagaaa ggcggacagg tatccggtaa gcggcagggt cggaacagga gagcgcacga    6540
gggagcttcc agggggaaac gcctggtatc tttatagtcc tgtcgggttt cgccacctct    6600
gacttgagcg tcgatttttg tgatgctcgt caggggggcg gagcctatgg aaaaacgcca    6660
gcaacgcggc cttttacgg ttcctggcct tttgctggcc ttttgctcac atgtgggagc    6720
ctagggtaca tttaggtgac actata                                        6746
```

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

-continued tgatccgacc agcaaaactc                                              20

<210> SEQ ID NO 43
<211> LENGTH: 124
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtgggagcct agggtacatt taggtgacac tataggatat agtggtgagt atccccgcct    60
gtcatgcggg agaccggggt tcggttcccc gacggggagc aaacagccg accaattgca   120 ctac                                                              124

<210> SEQ ID NO 44
<211> LENGTH: 124
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gtagtgcaat tggtcggctg tttggctccc cgtcggggaa ccgaaccccg gtctcccgca    60
tgacaggcgg ggatactcac cactatatcc tatagtgtca cctaaatgta ccctaggctc   120
ccac                                                              124

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtgggagcct agggtac                                                 17

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtagtgcaat tggtcgg                                                 17

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gctcacatgt gggagcctag ggtacattta ggtgac                            36

<210> SEQ ID NO 48
<211> LENGTH: 36
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 48
gtcacctaaa tgtaccctag gctcccacat gtgagc                                   36

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtcagccggc cgcgcatgca gggtatacct gcaag                                    35

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cttgcaggta taccctgcat gcgcggccgg ctgac                                    35

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccgtacacgc aggcctcttc aggatttgag atgtgg                                   36

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccacatctca aatcctgaag aggcctgcgt gtacgg                                   36

<210> SEQ ID NO 53
<211> LENGTH: 463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ggatatagtg gtgagtatcc ccgcctgtca cgcgggagac cggggttcgg ttccccgacg         60
gggagccaaa cagccgacca attgcactac catcacaatg gagaagccag tagtaaacgt        120
agacgtagac ccccagagtc cgtttgtcgt gcaactgcaa aaagcttccc gcaatttgag        180
gtagtagcac agcaggtcac tccaaatgac catgctaatg ccagagcatt ttcgcatctg        240
gccagtaaac taatcgagct ggaggttcct accacagcga cgatcttgga cataggcagc        300
```

```
gcaccggctc gtagcatgtt ttccgagcac cagtatcatt gtgtctgccc catgcgtagt    360
ccagaagacc cggaccgcat gatgaaatat gccagtaaac tggcggaaaa agcgtgcaag    420
attacaaaca agaacttgca tgagaagatt aaggatctcc gga                      463
```

<210> SEQ ID NO 54
<211> LENGTH: 464
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
ggatatagtg gtgagtatcc ccgcctgtca tgcgggagac cggggttcgg ttccccgacg    60
gggagccaaa cagccgacca attgcactac catcacaatg gagaagccag tagtaaacgt    120
agacgtagac ccccagagtc cgtttgtcgt gcaactgcaa aaaagcttcc cgcaatttga    180
ggtagtagca cagcaggtca ctccaaatga ccatgctaat gccagagcat tttcgcatct    240
ggccagtaaa ctaatcgagc tggaggttcc taccacagcg acgatcttgg acataggcag    300
cgcaccggct cgtagaatgt tttccgagca ccagtatcat tgtgtctgcc ccatgcgtag    360
tccagaagac ccggaccgca tgatgaaata tgccagtaaa ctggcggaaa aagcgtgcaa    420
gattacaaac aagaacttgc atgagaagat taaggatctc cgga                     464
```

<210> SEQ ID NO 55
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

```
aaatatgcca gtaaactggc ggaaaaagcg tgcaagatta caaacaagaa cttgcatgag    60
aagattaagg atctccgga                                                 79
```

<210> SEQ ID NO 56
<211> LENGTH: 143
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
gatcctagga tatcaacagc tatgacatga ttacgaattt aatacgactc actataggat    60
atagtggtga gtatccccgc ctgtcatgcg ggagaccggg gttcggttcc ccgacgggga    120
gccaaacagc cgaccaattg cac                                            143
```

<210> SEQ ID NO 57
<211> LENGTH: 143
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
gtgcaattgg tcggctgttt ggctccccgt cggggaaccg aacccggtc tcccgcatga    60 caggcgggga tactcaccac tatatcctat agtgagtcgt attaaattcg taatcatgtc    120
```

```
<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcggccgcct cgaggacgtg atatcgcact tttcggggaa a                           41

<210> SEQ ID NO 59
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tttccccgaa aagtgcgata tcacgtcctc gaggcggccg c                           41

<210> SEQ ID NO 60
<211> LENGTH: 6771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
```

| | |
|---|---|
| ggatatagtg gtgagtatcc ccgcctgtca tgcgggagac cggggttcgg ttccccgacg | 60 |
| gggagccaaa cagccgacca attgcactac catcacaatg gagaagccag tagtaaacgt | 120 |
| agacgtagac ccccagagtc cgtttgtcgt gcaactgcaa aaaagcttcc cgcaatttga | 180 |
| ggtagtagca cagcaggtca ctccaaatga ccatgctaat gccagagcat tttcgcatct | 240 |
| ggccagtaaa ctaatcgagc tggaggttcc taccacagcg acgatcttgg acataggcag | 300 |
| cgcaccggct cgtagaatgt tttccgagca ccagtatcat tgtgtctgcc ccatgcgtag | 360 |
| tccagaagac ccggaccgca tgatgaaata tgccagtaaa ctggcggaaa agcgtgcaa | 420 |
| gattacaaac aagaacttgc atgagaagat taaggatctc cggatcccct gaaaaggctg | 480 |
| tttaagttgg gtaaaccgct cccagccgac gacgagcaag acgaagacag aagacgcgct | 540 |
| ctgctagatg aaacaaaggc gtggtttaga gtaggtataa caggcacttt agcagtggcc | 600 |
| gtgacgaccc ggtatgaggt agacaatatt acacctgtcc tactggcatt gagaactttt | 660 |
| gcccagagca aaagagcatt ccaagccatc agagggaaa taaagcatct ctacggtggt | 720 |
| cctaaatagt cagcatagta catttcatct gactaatact acaacaccac caccatgaat | 780 |
| agaggattct ttaacatgct cggccgccgc cccttcccgg ccccactgc catgtggagg | 840 |
| ccgcggagaa ggaggcaggc ggccccgatg cctgccgca acgggctggc ttctcaaatc | 900 |
| cagcaactga ccacagccgt cagtgcccta gtcattggac aggcaactag acctcaaccc | 960 |
| ccacgtccac gccagccacc gcgccagaag aagcaggcgc ccaagcaacc accgaagccg | 1020 |
| aagaaaccaa aaacgcagga gaagaagaag aagcaacctg caaaacccaa acccggaaag | 1080 |
| agacagcgcg tggcacttaa gttggaggcc gacagattgt tcgacgtcaa gaacgaggac | 1140 |
| ggagatgtca tcgggcacgc actggccatg gaaggaaagg taatgaaacc tctgcacgtg | 1200 |

```
aaaggaacca tcgaccaccc tgtgctatca aagctcaaat ttaccaagtc gtcagcatac    1260
gacatggagt tcgcacagtt gccagtcaac atgagaagtg aggcattcac ctacaccagt    1320
gaacaccccg aaggattcta taactggcac cacggagcgg tgcagtatag tggaggtaga    1380
tttaccatcc ctcgcggagt aggaggcaga ggagacagcg tcgtccgat catggataac     1440 tccggtcggg ttgtcgcgat agtcctcggt ggagctgatg aaggaacacg aactgccctt    1500
tcggtcgtca cctggaatag taaagggaag acaattaaga cgaccccgga agggacagaa    1560
gagtggtccg cagcaccact ggtcacggca atgtgtttgc tcggaaatgt gagcttccca    1620
tgcgaccgcc cgcccacatg ctatacccgc gaaccttcca gagccctcga catccttgaa    1680
gagaacgtga accatgaggc ctacgatacc ctgctcaatg ccatattgcg gtgcggatcg    1740
tctggcagaa gcaaaagaag cgtcatcgat gactttaccc tgaccagccc ctacttgggc    1800
acatgctcgt actgccacca tactgaaccg tgcttcagcc ctgttaagat cgagcaggtc    1860
tgggacgaag cggacgataa caccatacgc atacagactt ccgcccagtt tggatacgac    1920
caaagcggag cagcaagcgc aaacaagtac cgctacatgt cgcttaagca ggatcacacc    1980
gttaaagaag gcaccatgga tgacatcaag attagcacct caggaccgtg tagaaggctt    2040
agctacaaag gatactttct cctcgcaaaa tgccctccag gggacagcgt aacggttagc    2100
atagtgagta gcaactcagc aacgtcatgt acactggccc gcaagataaa accaaaattc    2160
gtgggacggg aaaaatatga tctacctccc gttcacggta aaaaaattcc ttgcacagtg    2220
tacgaccgtc tgaaagaaac aactgcaggc tacatcacta tgcacaggcc gggcccgcac    2280
gcttatacat cctacctgga agaatcatca gggaaagttt acgcaaagcc gccatctggg    2340
aagaacatta cgtatgagtg caagtgcggc gactacaaga ccggaaccgt ttcgacccgc    2400
accgaaatca ctggttgcac cgccatcaag cagtgcgtcg cctataagag cgaccaaacg    2460
aagtgggtct tcaactcacc ggacttgatc cgacatgacg accacacggt ccaagggaaa    2520
ttgcatttgc ctttcaagtt gatcccgagt acctgcatgg tccctgttgc ccacgcgccg    2580
aatgtaatac atggctttaa acacatcagc ctccaattag atacagacca cttgacattg    2640
ctcaccacca ggagactagg ggcaaacccg gaaccaacca ctgaatggat cgtcggaaag    2700
acggtcagaa acttcaccgt cgaccgagat ggcctggaat acatatgggg aaatcatgag    2760
ccagtgaggg tctatgccca agagtcagca ccaggagacc ctcacggatg ccacacgaa     2820 atagtacagc attactacca tcgccatcct gtgtacacca tcttagccgt cgcatcagct    2880
accgtggcga tgatgattgg cgtaactgtt gcagtgttat gtgcctgtaa agcgcgccgt    2940
gagtgcctga cgccatacgc cctggcccca aacgccgtaa tcccaacttc gctggcactc    3000
ttgtgctgcg ttaggtcggc caatgctgaa acgttcaccg agaccatgag ttacttgtgg    3060
tcgaacagtc agccgttctt ctgggtccag ttgtgcatac cttggccgc tttcatcgtt     3120 ctaatgcgct gctgctcctg ctgcctgcct ttttagtgg ttgccggcgc ctacctggcg     3180
aaggtagacg cctacgaaca tgcgaccact gttccaaatg tgccacagat accgtataag    3240
gcacttgttg aaagggcagg gtatgccccg ctcaatttgg agatcactgt catgtcctcg    3300
gaggttttgc cttccaccaa ccaagagtac attacctgca aattcaccac tgtggtcccc    3360
tccccaaaaa tcaaatgctg cggctccttg gaatgtcagc cggccgcgca tgcagggtat    3420
acctgcaagg tcttcggagg ggtctacccc tttatgtggg gaggagcgca atgttttttgc    3480 gacagtgaga acagccagat gagtgaggcg tacgtcgaac tgtcagcaga ttgcgcgtct    3540
gaccacgcgc aggcgattaa ggtgcacact gccgcgatga agtaggact gcgtatagtg      3600
```

```
tacgggaaca ctaccagttt cctagatgtg tacgtgaacg gagtcacacc aggaacgtct    3660
aaagacttga aagtcatagc tggaccaatt tcagcatcgt ttacgccatt cgatcataag    3720
gtcgttatcc atcgcggcct ggtgtacaac tatgacttcc cggaatatgg agcgatgaaa    3780
ccaggagcgt ttggagacat tcaagctacc tccttgacta gcaaggatct catcgccagc    3840
acagacatta ggctactcaa gccttccgcc aagaacgtgc atgtcccgta cacgcaggcc    3900
tcttcaggat ttgagatgtg gaaaaacaac tcaggccgcc cactgcagga aaccgcacct    3960
ttcgggtgta agattgcagt aaatccgctc cgagcggtgg actgttcata cgggaacatt    4020
cccatttcta ttgacatccc gaacgctgcc tttatcagga catcagatgc accactggtc    4080
tcaacagtca aatgtgaagt cagtgagtgc acttattcag cagacttcgg cgggatggcc    4140
accctgcagt atgtatccga ccgcgaaggt caatgcccg tacattcgca ttcgagcaca    4200
gcaactctcc aagagtcgac agtacatgtc ctggagaaag gagcggtgac agtacacttt    4260
agcaccgcga gtccacaggc gaactttatc gtatcgctgt gtgggaagaa gacaacatgc    4320
aatgcagaat gtaaaccacc agctgaccat atcgtgagca ccccgcacaa aaatgaccaa    4380
gaatttcaag ccgccatctc aaaaacatca tggagttggc tgtttgccct tttcggcggc    4440
gcctcgtcgc tattaattat aggacttatg attttttgctt gcagcatgat gctgactagc    4500
acacgaagat gaccgctacg ccccaatgat ccgaccagca aaactcgatg tacttccgag    4560
gaactgatgt gcataatgca tcaggctggt acattagatc cccgcttacc gcgggcaata    4620
tagcaacact aaaaactcga tgtacttccg aggaagcgca gtgcataatg ctgcgcagtg    4680
ttgccacata accactatat taaccattta tctagcggac gccaaaaact caatgtattt    4740
ctgaggaagc gtggtgcata atgccacgca gcgtctgcat aactttttatt atttcttttta    4800 ttaatcaaca aaattttgtt tttaacattt caaaaaaaaa aaaaaaaaaa aaaaaaaaaa    4860 aaaaaaatt taaattaatt aagcggccgc ctcgaggacg tgatatcgca cttttcgggg    4920
aaatgtgcgc ggaacccta tttgtttatt tttctaaata cattcaaata tgtatccgct    4980
catgagacaa taaccctgat aaatgcttca ataatattga aaaggaaga gtatgagtat    5040 tcaacatttc cgtgtcgccc ttattccctt ttttgcggca ttttgccttc ctgttttgc    5100 tcacccagaa acgctggtga agtaaaaga tgctgaagat cagttgggtg cacgagtggg    5160
ttacatcgaa ctggatctca acagcggtaa gatccttgag agttttcgcc ccgaagaacg    5220
ttttccaatg atgagcactt ttaaagttct gctatgtggc gcggtattat cccgtattga    5280
cgccgggcaa gagcaactcg gtcgccgcat acactattct cagaatgact tggttgagta    5340
ctcaccagtc acagaaaagc atcttacgga tggcatgaca gtaagagaat tatgcagtgc    5400
tgccataacc atgagtgata acactgcggc caacttactt ctgacaacga tcggaggacc    5460
gaaggagcta accgcttttt tgcacaacat ggggatcat gtaactcgcc ttgatcgttg    5520
ggaaccggag ctgaatgaag ccataccaaa cgacagcgt gacaccacga tgcctgtagc    5580
aatggcaaca acgttgcgca aactattaac tggcgaacta cttactctag cttcccggca    5640
acaattaata gactggatgg aggcggataa agttgcagga ccacttctgc gctcggccct    5700
tccggctggc tggtttattg ctgataaatc tggagccggt gagcgtgggt ctcgcggtat    5760
cattgcagca ctggggccag atggtaagcc ctcccgtatc gtagttatct acacgacggg    5820
gagtcaggca actatggatg aacgaaatag acagatcgct gagataggtg cctcactgat    5880
taagcattgg taactgtcag accaagttta ctcatatata ctttagattg atttaaaact    5940
tcatttttaa tttaaaagga tctaggtgaa gatcctttt gataatctca tgaccaaaat    6000
```

```
cccttaacgt gagttttcgt tccactgagc gtcagacccc gtagaaaaga tcaaaggatc    6060
ttcttgagat cctttttttc tgcgcgtaat ctgctgcttg caaacaaaaa aaccaccgct    6120
accagcggtg gtttgtttgc cggatcaaga gctaccaact cttttccga aggtaactgg     6180 cttcagcaga gcgcagatac caaatactgt ccttctagtg tagccgtagt taggccacca    6240
cttcaagaac tctgtagcac cgcctacata cctcgctctg ctaatcctgt taccagtggc    6300
tgctgccagt ggcgataagt cgtgtcttac cgggttggac tcaagacgat agttaccgga    6360
taaggcgcag cggtcgggct gaacggggggg ttcgtgcaca cagcccagct tggagcgaac    6420
gacctacacc gaactgagat acctacacg tgagctatga aaagcgcca cgcttcccga      6480 agggagaaag gcggacaggt atccggtaag cggcagggtc ggaacaggag agcgcacgag    6540
ggagcttcca gggggaaacg cctggtatct ttatagtcct gtcgggtttc gccacctctg    6600
acttgagcgt cgatttttgt gatgctcgtc aggggggcgg agcctatgga aaaacgccag    6660
caacgcggcc ttttacggt tcctggcctt ttgctggcct tttgctcaca tgtgggagcc     6720
taggatatca acagctatga catgattacg aatttaatac gactcactat a             6771

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
catgtgggag gcctgagtac ttaatacgac tcactatagg                           40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cctatagtga gtcgtattaa gtactcaggc ctcccacatg                           40

<210> SEQ ID NO 63
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cctcgaggac gtcaggtagg ccttttcggg gaaatgtgc                            39

<210> SEQ ID NO 64
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcacatttcc ccgaaaaggc ctacctgacg tcctcgagg                            39

<210> SEQ ID NO 65
```

```
<211> LENGTH: 13092
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
```

| | | | | | |
|---|---|---|---|---|---|
| attgacggcg | tagtacacac | tattgaatca | aacagccgac | caattgcact | accatcacaa    60 |
| tggagaagcc | agtagtaaac | gtagacgtag | accccccagag | tccgtttgtc | gtgcaactgc   120 |
| aaaaaagctt | cccgcaattt | gaggtagtag | cacagcaggt | cactccaaat | gaccatgcta   180 |
| atgccagagc | attttcgcat | ctggccagta | aactaatcga | gctggaggtt | cctaccacag   240 |
| cgacgatctt | ggacataggc | agcgcaccgg | ctcgtagaat | gttttccgag | caccagtatc   300 |
| attgtgtctg | ccccatgcgt | agtccagaag | acccggaccg | catgatgaaa | tatgccagta   360 |
| aactggcgga | aaaagcgtgc | aagattacaa | acaagaactt | gcatgagaag | attaaggatc   420 |
| tccggaccgt | acttgatacg | ccggatgctg | aaacaccatc | gctctgcttt | cacaacgatg   480 |
| ttacctgcaa | catgcgtgcc | gaatattccg | tcatgcagga | cgtgtatatc | aacgctcccg   540 |
| gaactatcta | tcatcaggct | atgaaaggcg | tgcggaccct | gtactggatt | ggcttcgaca   600 |
| ccacccagtt | catgttctcg | gctatggcag | gttcgtaccc | tgcgtacaac | accaactggg   660 |
| ccgacgagaa | agtccttgaa | gcgcgtaaca | tcggactttg | cagcacaaag | ctgagtgaag   720 |
| gtaggacagg | aaaattgtcg | ataatgagga | agaaggagtt | gaagcccggg | tcgcgggttt   780 |
| atttctccgt | aggatcgaca | ctttatccag | aacacagagc | cagcttgcag | agctggcatc   840 |
| ttccatcggt | gttccacttg | aatggaaagc | agtcgtacac | ttgccgctgt | gatacagtgg   900 |
| tgagttgcga | aggctacgta | gtgaagaaaa | tcaccatcag | tcccgggatc | acgggagaaa   960 |
| ccgtgggata | cgcggttaca | cacaatagcg | agggcttctt | gctatgcaaa | gttactgaca  1020 |
| cagtaaaagg | agaacgggta | tcgttccctg | tgtgcacgta | catcccggcc | accatatgcg  1080 |
| atcagatgac | tggtataatg | gccacggata | tatcacctga | cgatgcacaa | aaacttctgg  1140 |
| ttgggctcaa | ccagcgaatt | gtcattaacg | gtaggactaa | caggaacacc | aacaccatgc  1200 |
| aaaattaccct | tctgccgatc | atagcacaag | ggttcagcaa | atgggctaag | gagcgcaagg  1260 |
| atgatcttga | taacgagaaa | atgctgggta | ctagagaacg | caagcttacg | tatggctgct  1320 |
| tgtgggcgtt | tcgcactaag | aaagtacatt | cgttttatcg | cccacctgga | acgcagacca  1380 |
| tcgtaaaagt | cccagcctct | tttagcgctt | ttcccatgtc | gtccgtatgg | acgacctctt  1440 |
| tgcccatgtc | gctgaggcag | aaattgaaac | tggcattgca | accaaagaag | gaggaaaaac  1500 |
| tgctgcaggt | ctcggaggaa | ttagtcatgg | aggccaaggc | tgcttttgag | gatgctcagg  1560 |
| aggaagccag | agcggagaag | ctccgagaag | cacttccacc | attagtggca | gacaaaggca  1620 |
| tcgaggcagc | cgcagaagtt | gtctgcgaag | tggaggggct | ccaggcggac | atcggagcag  1680 |
| cattagttga | aacccccgcgc | ggtcacgtaa | ggataatacc | tcaagcaaat | gaccgtatga  1740 |
| tcggacagta | tatcgttgtc | tcgccaaact | ctgtgctgaa | gaatgccaaa | ctcgcaccag  1800 |
| cgcacccgct | agcagatcag | gttaagatca | taacacactc | cggaagatca | ggaaggtacg  1860 |
| cggtcgaacc | atacgacgct | aaagtactga | tgccagcagg | aggtgccgta | ccatggccag  1920 |
| aattcctagc | actgagtgag | agcgccacgt | tagtgtacaa | cgaaagagag | tttgtgaacc  1980 |
| gcaaactata | ccacattgcc | atgcatggcc | ccgccaagaa | tacagaagag | gagcagtaca  2040 |
| aggttacaaa | ggcagagctt | gcagaaacag | agtacgtgtt | tgacgtggac | aagaagcgtt  2100 |
| gcgttaagaa | ggaagaagcc | tcaggtctgg | tcctctcggg | agaactgacc | aaccctcct  2160 |

```
atcatgagct agctctggag ggactgaaga cccgacctgc ggtcccgtac aaggtcgaaa    2220
caataggagt gataggcaca ccggggtcgg gcaagtcagc tattatcaag tcaactgtca    2280
cggcacgaga tcttgttacc agcggaaaga aagaaaattg tcgcgaaatt gaggccgacg    2340
tgctaagact gaggggtatg cagattacgt cgaagacagt agattcggtt atgctcaacg    2400
gatgccacaa agccgtagaa gtgctgtacg ttgacgaagc gttcgcgtgc cacgcaggag    2460
cactacttgc cttgattgct atcgtcaggc cccgcaagaa ggtagtacta tgcggagacc    2520
ccatgcaatg cggattcttc aacatgatgc aactaaaggt acatttcaat caccctgaaa    2580
aagacatatg caccaagaca ttctacaagt atatctcccg gcgttgcaca cagccagtta    2640
cagctattgt atcgacactg cattacgatg gaaagatgaa aaccacgaac ccgtgcaaga    2700
agaacattga aatcgatatt acaggggcca caaagccgaa gccagggat atcatcctga    2760 catgtttccg cgggtgggtt aagcaattgc aaatcgacta tcccggacat gaagtaatga    2820
cagccgcggc ctcacaaggg ctaaccagaa aaggagtgta tgccgtccgg caaaaagtca    2880
atgaaaaccc actgtacgcg atcacatcag agcatgtgaa cgtgttgctc acccgcactg    2940
aggacaggct agtgtggaaa accttgcagg gcgacccatg gattaagcag ctcactaaca    3000
tacctaaagg aaactttcag gctactatag aggactggga agctgaacac aagggaataa    3060
ttgctgcaat aaacagcccc actccccgtg ccaatccgtt cagctgcaag accaacgttt    3120
gctgggcgaa agcattggaa ccgatactag ccacggccgg tatcgtactt accggttgcc    3180
agtggagcga actgttccca cagtttgcgg atgacaaacc acattcggcc atttacgcct    3240
tagacgtaat ttgcattaag ttttttcggca tggacttgac aagcggactg ttttctaaac    3300
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg cacacaact tgatttgcag acggggagaa    3480
ccagagttat ctctgcacag cataacctgg tcccggtgaa ccgcaatctt cctcacgcct    3540
tagtccccga gtacaaggag aagcaaccccg gccggtcga aaaattcttg aaccagttca    3600
aacaccactc agtacttgtg gtatcagagg aaaaaattga agctccccgt aagagaatcg    3660
aatggatcgc cccgattggc atagccggtg cagataagaa ctacaacctg gctttcgggt    3720
ttccgccgca ggcacggtac gacctggtgt tcatcaacat tggaactaaa tacagaaacc    3780
accactttca gcagtgcgaa gaccatgcgg cgaccttaaa aaccctttcg cgttcggccc    3840
tgaattgcct taacccagga ggcaccctcg tggtgaagtc ctatggctac gccgaccgca    3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcaccccg caccatctga ttgcgtgat tcgtccgtg tatgagggta    4080 caagagatgg agttggagcc gcgccgtcat accgcaccaa aagggagaat attgctgact    4140
gtcaagagga agcagttgtc aacgcagcca atcgctggg tagaccaggc gaaggagtct    4200
gccgtgccat ctataaacgt tggccgacca gttttaccga ttcagccacg gagacaggca    4260
ccgcaagaat gactgtgtgc ctaggaaaga aagtgatcca cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
acgcagccgg aaaagaccgc cttgaagtat cacttaactg cttgacaacc gcgctagaca    4500
gaactgacgc ggacgtaacc atctattgcc tggataagaa gtggaaggaa agaatcgacg    4560
```

```
cggcactcca acttaaggag tctgtaacag agctgaagga tgaagatatg gagatcgacg    4620
atgagttagt atggatccat ccagacagtt gcttgaaggg aagaaaggga ttcagtacta    4680
caaaaggaaa attgtattcg tacttcgaag gcaccaaatt ccatcaagca gcaaaagaca    4740
tggcggagat aaaggtcctg ttccctaatg accaggaaag taatgaacaa ctgtgtgcct    4800
acatattggg tgagaccatg gaagcaatcc gcgaaaagtg cccggtcgac cataacccgt    4860
cgtctagccc gcccaaaacg ttgccgtgcc tttgcatgta tgccatgacg ccagaaaggg    4920
tccacagact tagaagcaat aacgtcaaag aagttacagt atgctcctcc acccccttc     4980 ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggcccccg aagttgtagc gacaccgtca ccatctacag    5160
ctgataacac ctcgcttgat gtcacagaca tctcactgga tatggatgac agtagcgaag    5220
gctcactttt ttcgagcttt agcggatcgg acaactctat tactagtatg gacagttggt    5280
cgtcaggacc tagttcacta gagatagtag accgaaggca ggtggtggtg gctgacgttc    5340
atgccgtcca gagcctgcc cctattccac cgccaaggct aaagaagatg gcccgcctgg     5400
cagcggcaag aaaagagccc actccaccgg caagcaatag ctctgagtcc ctccacctct    5460
cttttggtgg ggtatccatg tccctcggat caatttttcga cggagagacg gcccgccagg   5520
cagcggtaca accoctggca acaggcccca cggatgtgcc tatgtctttc ggatcgtttt    5580
ccgacggaga gattgatgag ctgagccgca gagtaactga gtccgaaccc gtcctgtttg    5640
gatcatttga accgggcgaa gtgaactcaa ttatatcgtc ccgatcagcc gtatcttttc    5700
cactacgcaa gcagagacgt agacgcagga gcaggaggac tgaatactga ctaaccgggg    5760
taggtgggta catattttcg acggacacag gccctgggca cttgcaaaag aagtccgttc    5820
tgcagaacca gcttacagaa ccgaccttgg agcgcaatgt cctggaaaga attcatgccc    5880
cggtgctcga cacgtcgaaa gaggaacaac tcaaactcag gtaccagatg atgcccaccg    5940
aagccaacaa aagtaggtac cagtctcgta aagtagaaaa tcagaaagcc ataaccactg    6000
agcgactact gtcaggacta cgactgtata actctgccac agatcagcca gaatgctata    6060
agatcaccta tccgaaacca ttgtactcca gtagcgtacc ggcgaactac tccgatccac    6120
agttcgctgt agctgtctgt aacaactatc tgcatgagaa ctatccgaca gtagcatctt    6180
atcagattac tgacgagtac gatgcttact tggatatggt agacgggaca gtcgcctgcc    6240
tggatactgc aaccttctgc cccgctaagc ttagaagtta cccgaaaaaa catgagtata    6300
gagccccgaa tatccgcagt gcggttccat cagcgatgca gaacacgcta caaaatgtgc    6360
tcattgccgc aactaaaaga aattgcaacg tcacgcagat gcgtgaactg ccaacactgg    6420
actcagcgac attcaatgtc gaatgctttc gaaaatatgc atgtaatgac gagtattggg    6480
aggagttcgc tcggaagcca attaggatta ccactgagtt tgtcaccgca tatgtagcta    6540
gactgaaagg ccctaaggcc gccgcactat ttgcaaagac gtataatttg gtcccattgc    6600
aagaagtgcc tatggataga ttcgtcatgg acatgaaaag agacgtgaaa gttacaccag    6660
gcacgaaaca cacagaagaa agaccgaaag tacaagtgat acaagccgca gaaccctggg    6720
cgactgctta cttatgcggg attcaccggg aattagtgcg taggcttacg gccgtcttgc    6780
ttccaaacat tcacacgctt tttgacatgt cggcggagga ttttgatgca atcatagcag    6840
aacacttcaa gcaaggcgac ccggtactgg agacggatat cgcatcattc gacaaaagcc    6900
aagacgacgc tatggcgtta accggtctga tgatcttgga ggacctgggt gtggatcaac    6960
```

```
cactactcga cttgatcgag tgcgcctttg gagaaatatc atccacccat ctacctacgg  7020
gtactcgttt taaattcggg gcgatgatga aatccggaat gttcctcaca ctttttgtca  7080
acacagtttt gaatgtcgtt atcgccagca gagtactaga agagcggctt aaaacgtcca  7140
gatgtgcagc gttcattggc gacgacaaca tcatacatgg agtagtatct gacaaagaaa  7200
tggctgagag gtgcgccacc tggctcaaca tggaggttaa gatcatcgac gcagtcatcg  7260
gtgagagacc accttacttc tgcggcggat ttatcttgca agattcggtt acttccacag  7320
cgtgccgcgt ggcggacccc ctgaaaaggc tgtttaagtt gggtaaaccg ctcccagccg  7380
acgacgagca agacgaagac agaagacgcg ctctgctaga tgaaacaaag gcgtggttta  7440
gagtaggtat aacaggcact ttagcagtgg ccgtgacgac ccggtatgag gtagacaata  7500
ttacacctgt cctactggca ttgagaactt ttgcccagag caaaagagca ttccaagcca  7560
tcagagggga aataaagcat ctctacggtg gtcctaaata gtcagcatag tacatttcat  7620
ctgactaata ctacaacacc accacctcta gaccatggat cccgtcgttt tacaacgtcg  7680
tgactgggaa aaccctggcg ttacccaact taatcgcctt gcagcacatc cccctttcgc  7740
cagctggcgt aatagcgaag aggcccgcac cgatcgccct tcccaacagt tgcgcagcct  7800
gaatggcgaa tggcgctttg cctggttttcc ggcaccagaa gcggtgccgg aaagctggct  7860
ggagtgcgat cttcctgagg ccgatactgt cgtcgtcccc tcaaactggc agatgcacgg  7920
ttacgatgcg cccatctaca ccaacgtgac ctatcccatt acggtcaatc cgccgtttgt  7980
tcccacggag aatccgacgg gttgttactc gctcacattt aatgttgatg aaagctggct  8040
acaggaaggc cagacgcgaa ttattttttga tggcgttaac tcggcgtttc atctgtggtg  8100
caacgggcgc tgggtcggtt acggccagga cagtcgtttg ccgtctgaat ttgacctgag  8160
cgcatttttta cgcgccggag aaaaccgcct cgcggtgatg gtgctgcgct ggagtgacgg  8220
cagttatctg gaagatcagg atatgtgcg gatgagcggc attttccgtg acgtctcgtt  8280
gctgcataaa ccgactacac aaatcagcga tttccatgtt gccactcgct ttaatgatga  8340
tttcagccgc gctgtactgg aggctgaagt tcagatgtgc ggcgagttgc gtgactacct  8400
acgggtaaca gtttctttat ggcagggtga aacgcaggtc gccagcggca ccgcgccttt  8460
cggcggtgaa attatcgatg agcgtggtgg ttatgccgat cgcgtcacac tacgtctgaa  8520
cgtcgaaaac ccgaaactgt ggagcgccga atcccgaat ctctatcgtg cggtggttga  8580
actgcacacc gccgacggca cgctgattga agcagaagcc tgcgatgtcg gtttccgcga  8640
ggtgcggatt gaaaatggtc tgctgctgct gaacggcaag ccgttgctga ttcgaggcgt  8700
taaccgtcac gagcatcatc ctctgcatgg tcaggtcatg gatgagcaga cgatggtgca  8760
ggatatcctg ctgatgaagc agaacaactt taacgccgtg cgctgttcgc attatccgaa  8820
ccatccgctg tggtacacgc tgtgcgaccg ctacggcctg tatgtggtgg atgaagccaa  8880
tattgaaacc cacggcatgg tgccaatgaa tcgtctgacc gatgatccgc gctggctacc  8940
ggcgatgagc gaacgcgtaa cgcgaatggt gcagcgcgat cgtaatcacc cgagtgtgat  9000
catctggtcg ctggggaatg aatcaggcca cggcgctaat cacgacgcgc tgtatcgctg  9060
gatcaaatct gtcgatcctt cccgcccggt gcagtatgaa ggcggcggag ccgacaccac  9120
ggccaccgat attatttgcc cgatgtacgc gcgcgtggat aagaccagc ccttcccggc  9180
tgtgccgaaa tggtccatca aaaaatggct ttcgctacct ggagagacgc gcccgctgat  9240
cctttgcgaa tacgcccacg cgatgggtaa cagtcttggc ggtttcgcta atactggca  9300
ggcgtttcgt cagtatcccc gtttacaggg cggcttcgtc tgggactggg tggatcagtc  9360
```

```
gctgattaaa tatgatgaaa acggcaaccc gtggtcggct tacggcggtg attttggcga   9420
tacgccgaac gatcgccagt tctgtatgaa cggtctggtc tttgccgacc gcacgccgca   9480
tccagcgctg acggaagcaa aacaccagca gcagttttc cagttccgtt tatccgggca    9540
aaccatcgaa gtgaccagcg aatacctgtt ccgtcatagc gataacgagc tcctgcactg   9600
gatggtggcg ctggatggta agccgctggc aagcggtgaa gtgcctctgg atgtcgctcc   9660
acaaggtaaa cagttgattg aactgcctga actaccgcag ccggagagcg ccgggcaact   9720
ctggctcaca gtacgcgtag tgcaaccgaa cgcgaccgca tggtcagaag ccgggcacat   9780
cagcgcctgg cagcagtggc gtctggcgga aaacctcagt gtgacgctcc ccgccgcgtc   9840
ccacgccatc ccgcatctga ccaccagcga aatggatttt tgcatcgagc tgggtaataa   9900
gcgttggcaa tttaaccgcc agtcaggctt tctttcacag atgtggattg gcgataaaaa   9960
acaactgctg acgccgctgc gcgatcagtt cacccgtgca ccgctggata acgacattgg  10020
cgtaagtgaa gcgacccgca ttgaccctaa cgcctgggtc gaacgctgga aggcggcggg  10080
ccattaccag gccgaagcag cgttgttgca gtgcacggca gatacacttg ctgatgcggt  10140
gctgattacg accgctcacg cgtggcagca tcagggaaa accttattta tcagccggaa   10200
aacctaccgg attgatggta gtggtcaaat ggcgattacc gttgatgttg aagtggcgag  10260
cgatacaccg catccggcgc ggattggcct gaactgccag ctggcgcagg tagcagagcg  10320
ggtaaactgg ctcggattag ggccgcaaga aaactatccc gaccgcctta ctgccgcctg  10380
ttttgaccgc tgggatctgc cattgtcaga catgtatacc ccgtacgtct cccgagcga   10440 aaacggtctg cgctgcggga cgcgcgaatt gaattatggc ccacaccagt ggcgcggcga  10500
cttccagttc aacatcagcc gctacagtca acagcaactg atggaaacca gccatcgcca  10560
tctgctgcac gcggaagaag gcacatggct gaatatcgac ggtttccata tggggattgg  10620
tggcgacgac tcctggagcc cgtcagtatc ggcggaattc cagctgagcg ccggtcgcta  10680
ccattaccag ttggtctggt gtcaaaaata ataataaccg ggcagggggg atcctagacg  10740
ctacgcccca atgatccgac cagcaaaact cgatgtactt ccgaggaact gatgtgcata  10800
atgcaggaat tcgatatcaa gctagatctc acgtgagcat gcgtttaaac tgggcccaat  10860
gttccccaat gatccgacca gcaaaactcg atgtacttcc gaggaactga tgtgcataat  10920
gcatcaggct ggtacattag atccccgctt accgcgggca atatagcaac actaaaaact  10980
cgatgtactt ccgaggaagc gcagtgcata atgctgcgca gtgttgccac ataaccacta  11040
tattaaccat ttatctagcg gacgccaaaa actcaatgta tttctgagga agcgtggtgc  11100
ataatgccac gcagcgtctg cataactttt attatttctt ttattaatca acaaaatttt  11160 gttttaaca tttcaaaaaa aaaaaaaaaa aaaaaaaaa aaaaaaaaa aatttaaatt    11220 aattaagcgg ccgcctcgag gacgtcaggt aggcctttc ggggaaatgt gcgcggaacc    11280
cctatttgtt tattttcta aatacattca aatatgtatc cgctcatgag acaataaccc    11340
tgataaatgc ttcaataata ttgaaaaagg aagagtatga gtattcaaca tttccgtgtc  11400
gcccttattc ccttttttgc ggcattttgc cttcctgttt ttgctcaccc agaaacgctg   11460
gtgaaagtaa aagatgctga agatcagttg ggtgcacgag tgggttacat cgaactggat  11520
ctcaacagcg gtaagatcct tgagagtttt cgccccgaag aacgttttcc aatgatgagc  11580
acttttaaag ttctgctatg tggcgcggta ttatcccgta ttgacgccgg gcaagagcaa  11640
ctcggtcgcc gcatacacta ttctcagaat gacttggttg agtactcacc agtcacagaa  11700
aagcatctta cggatggcat gacagtaaga gaattatgca gtgctgccat aaccatgagt  11760
```

```
gataacactg cggccaactt acttctgaca acgatcggag gaccgaagga gctaaccgct    11820 ttttttgcaca acatgggga tcatgtaact cgccttgatc gttgggaacc ggagctgaat    11880
gaagccatac caaacgacga gcgtgacacc acgatgcctg tagcaatggc aacaacgttg    11940
cgcaaactat taactggcga actacttact ctagcttccc ggcaacaatt aatagactgg    12000
atggaggcgg ataaagttgc aggaccactt ctgcgctcgg cccttccggc tggctggttt    12060
attgctgata aatctggagc cggtgagcgt gggtctcgcg gtatcattgc agcactgggg    12120
ccagatggta agccctcccg tatcgtagtt atctacacga cggggagtca ggcaactatg    12180
gatgaacgaa atagacagat cgctgagata ggtgcctcac tgattaagca ttggtaactg    12240
tcagaccaag tttactcata tatactttag attgatttaa aacttcattt ttaatttaaa    12300
aggatctagg tgaagatcct ttttgataat ctcatgacca aaatccctta acgtgagttt    12360
tcgttccact gagcgtcaga ccccgtagaa aagatcaaag gatcttcttg agatcctttt    12420
tttctgcgcg taatctgctg cttgcaaaca aaaaaaccac cgctaccagc ggtggtttgt    12480
ttgccggatc aagagctacc aactcttttt ccgaaggtaa ctggcttcag cagagcgcag    12540
ataccaaata ctggtcttct agtgtagccg tagttaggcc accacttcaa gaactctgta    12600
gcaccgccta catacctcgc tctgctaatc ctgttaccag tggctgctgc cagtggcgat    12660
aagtcgtgtc ttaccgggtt ggactcaaga cgatagttac cggataaggc gcagcggtcg    12720
ggctgaacgg ggggttcgtg cacacagccc agcttggagc gaacgaccta caccgaactg    12780
agatacctac agcgtgagct atgagaaagc gccacgcttc ccgaagggag aaaggcggac    12840
aggtatccgg taagcggcag ggtcggaaca ggagagcgca cgagggagct tccaggggga    12900
aacgcctggt atctttatag tcctgtcggg tttcgccacc tctgacttga gcgtcgattt    12960
ttgtgatgct cgtcaggggg gcggagccta tggaaaaacg ccagcaacgc ggccttttta    13020
cggttcctgg ccttttgctg gccttttgct cacatgtggg aggcctgagt acttaatacg    13080
actcactata gg                                                       13092

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggctagagct catttaggtg aca                                           23

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggatctccgg atcccctgaa aagg                                          24

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Synthetic
```

```
                                  -continued
        primer

<400> SEQUENCE: 68
gtgaccagtg gactagtgga ccactcttc                                29

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggatctccgg atcccctgaa aaggctgt                                 28

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gatgaaagga tcctcgcgaa ctatttagga ccaccg                        36
```